United States Patent
Szlavik et al.

(10) Patent No.: US 10,322,131 B2
(45) Date of Patent: Jun. 18, 2019

(54) HYDROXYACID DERIVATIVES, A PROCESS FOR THEIR PREPARATION AND PHARMACEUTICAL COMPOSITIONS CONTAINING THEM

(71) Applicants: LES LABORATOIRES SERVIER, Suresnes (FR); VERNALIS (R&D) LTD, Winnersh (GB)

(72) Inventors: Zoltan Szlavik, Budapest (HU); Attila Paczal, Budapest (HU); Balazs Balint, Fot (HU); András Kotschy, Törökbálint (HU); Maïa Chanrion, Issy les Moulineaux (FR); Olivier Geneste, Rueil-Malmaison (FR); James Edward Paul Davidson, Great Shelford (GB); James Brooke Murray, Linton (GB); Szabolcs Sipos, Budapest (HU); Ágnes Proszenyák, Budapest (HU)

(73) Assignees: LES LABORATOIRES SERVIER, Suresnes (FR); VERNALIS (R&D) LTD, Winnersh Berkshire (GB)

( * ) Notice: Subject to any disclaimer, the term of this patent is extended or adjusted under 35 U.S.C. 154(b) by 0 days.

(21) Appl. No.: 15/738,601

(22) PCT Filed: Jun. 22, 2016

(86) PCT No.: PCT/EP2016/064417
§ 371 (c)(1),
(2) Date: Dec. 21, 2017

(87) PCT Pub. No.: WO2016/207216
PCT Pub. Date: Dec. 29, 2016

(65) Prior Publication Data
US 2018/0185369 A1    Jul. 5, 2018

(30) Foreign Application Priority Data
Jun. 23, 2015 (FR) .................... 15 55753

(51) Int. Cl.
*A61K 31/519* (2006.01)
*C07D 495/04* (2006.01)
*A61P 35/00* (2006.01)
*A61K 31/215* (2006.01)
*A61K 31/381* (2006.01)

(52) U.S. Cl.
CPC .......... *A61K 31/519* (2013.01); *A61K 31/215* (2013.01); *A61K 31/381* (2013.01); *A61P 35/00* (2018.01); *C07D 495/04* (2013.01)

(58) Field of Classification Search
None
See application file for complete search history.

(56) References Cited

U.S. PATENT DOCUMENTS

| | | | |
|---|---|---|---|
| 9,670,227 B2 * | 6/2017 | Kotschy | C07D 495/04 |
| 2015/0051189 A1 | 2/2015 | Le Diguarher et al. | |
| 2015/0175623 A1 * | 6/2015 | Kotschy | C07D 495/04 424/130.1 |
| 2017/0216293 A1 * | 8/2017 | Kotschy | C07D 495/04 |
| 2018/0170947 A1 * | 6/2018 | Szlavik | C07D 495/04 |
| 2018/0185369 A1 * | 7/2018 | Szl vik | C07D 495/04 |
| 2018/0258098 A1 * | 9/2018 | Balint | C07D 403/12 |
| 2019/0031675 A1 * | 1/2019 | Szlavik | C07D 495/04 |
| 2019/0031677 A1 * | 1/2019 | Paczal | C07D 495/04 |

FOREIGN PATENT DOCUMENTS

| | | |
|---|---|---|
| CN | 102464667 | 5/2012 |
| EP | 2886545 | 6/2015 |
| WO | WO2013072694 | 5/2013 |
| WO | WO2013110890 | 8/2013 |

OTHER PUBLICATIONS

A. Kotschy et al., 538 Nature (2016) (Year: 2016).*
J.D. Leverson et al., Cell Death and Disease (2015) (Year: 2015).*
J. Belmar et al., 145 Pharmacology & Therapeutics, 76-84 (2015) (Year: 2015).*
J.M. Michels et al., The International Journal of Biochemistry & Cell Biology, 267-271 (2005) (Year: 2005).*
Bruncko et al., 58 Journal of Medicinal Chemistry, 2180-2194 (2015) (Year: 2015).*
F.A. Abulwerdi et al., 57 Journal of Medicinal Chemistry, 4111-4133 (2015) (Year: 2015).*
International Search Report for PCT/EP2016/06417 dated Jul. 15, 2016.

* cited by examiner

*Primary Examiner* — Alexander R Pagano
(74) *Attorney, Agent, or Firm* — Hueschen and Sage

(57) ABSTRACT

Compounds of formula (I):

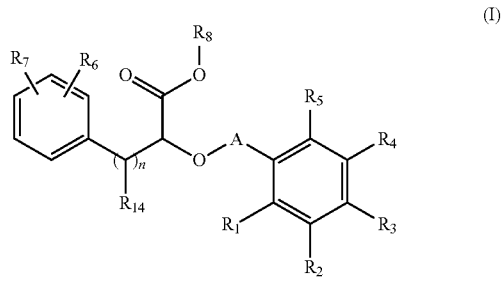

wherein $R_1$, $R_2$, $R_3$, $R_4$, $R_5$, $R_6$, $R_7$, $R_8$, $R_{14}$, A and n are as defined in the description.

31 Claims, No Drawings

HYDROXYACID DERIVATIVES, A PROCESS FOR THEIR PREPARATION AND PHARMACEUTICAL COMPOSITIONS CONTAINING THEM

The present invention relates to new hydroxyacid derivatives, to a process for their preparation and to pharmaceutical compositions containing them.

The compounds of the present invention are new and have very valuable pharmacological characteristics in the field of apoptosis and cancerology.

Apoptosis, or programmed cell death, is a physiological process that is crucial for embryonic development and maintenance of tissue homeostasis.

Apoptotic-type cell death involves morphological changes such as condensation of the nucleus, DNA fragmentation and also biochemical phenomena such as the activation of caspases which cause damage to key structural components of the cell, so inducing its disassembly and death. Regulation of the process of apoptosis is complex and involves the activation or repression of several intracellular signalling pathways (Cory S. et al., Nature Review Cancer 2002, 2, 647-656).

Deregulation of apoptosis is involved in certain pathologies. Increased apoptosis is associated with neurodegenerative diseases such as Parkinson's disease, Alzheimer's disease and ischaemia. Conversely, deficits in the implementation of apoptosis play a significant role in the development of cancers and their chemoresistance, in auto-immune diseases, inflammatory diseases and viral infections. Accordingly, absence of apoptosis is one of the phenotypic signatures of cancer (Hanahan D. et al., Cell 2000, 100, 57-70).

The anti-apoptotic proteins of the Bcl-2 family are associated with numerous pathologies. The involvement of proteins of the Bcl-2 family is described in numerous types of cancer, such as colon cancer, breast cancer, small-cell lung cancer, non-small-cell lung cancer, bladder cancer, ovarian cancer, prostate cancer, chronic lymphoid leukaemia, lymphoma, myeloma, acute myeloid leukemia, pancreatic cancer, etc. Overexpression of the anti-apoptotic proteins of the Bcl-2 family is involved in tumorigenesis, in resistance to chemotherapy and in the clinical prognosis of patients affected by cancer. Notably, Mcl-1, an anti-apoptotic Bcl-2 family member, is overexpressed in various types of cancer (Beroukhim R. et al., Nature 2010, 899-905). There is, therefore, a therapeutic need for compounds that inhibit the anti-apoptotic activity of the proteins of the Bcl-2 family.

In addition to being new, the compounds of the present invention have pro-apoptotic properties making it possible to use them in pathologies involving a defect in apoptosis, such as, for example, in the treatment of cancer and of immune and auto-immune diseases.

The present invention relates more especially to compounds of formula (I):

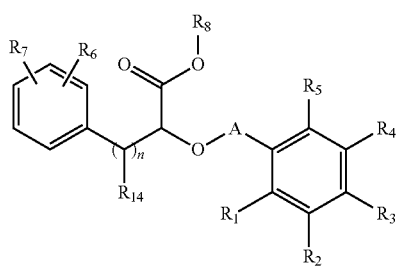

wherein:

A represents the group

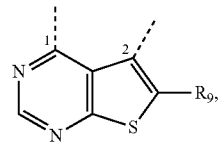

in which 1 is linked to the oxygen atom and 2 is linked to the phenyl ring, $R_1$ represents a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)alkoxy group, a —S—($C_1$-$C_6$)alkyl group, a linear or branched ($C_1$-$C_6$)polyhaloalkyl, a hydroxy group, a hydroxy($C_1$-$C_6$)alkyl group, a cyano group, —$NR_{12}R_{12}$', -$Cy_5$, or a halogen atom, $R_2$, $R_3$, $R_4$ and $R_5$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a hydroxy($C_1$-$C_6$)alkyl group, a linear or branched ($C_1$-$C_6$)alkoxy group, a —S—($C_1$-$C_6$)alkyl group, a cyano group, a nitro group, -alkyl($C_0$-$C_6$)—$NR_{10}R_{10}$', —O-alkyl($C_1$-$C_6$)—$NR_{10}R_{10}$', —O-alkyl($C_1$-$C_6$)—$R_{11}$, —C(O)—$OR_{10}$, —O—C(O)—$R_{10}$, —C(O)—$NR_{10}R_{10}$', —$NR_{10}$—C(O)—$R_{10}$', —$NR_{10}$—C(O)—$OR_{10}$', -alkyl($C_1$-$C_6$)—$NR_{10}$—C(O)—$R_{10}$', —$SO_2$—$NR_{10}R_{10}$', —$SO_2$-alkyl($C_1$-$C_6$), or the substituents of one of the pairs ($R_2$, $R_3$), ($R_3$, $R_4$), ($R_4$, $R_5$), when grafted onto two adjacent carbon atoms, form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by a group selected from a linear or branched ($C_1$-$C_6$)alkyl group, —$NR_{12}R_{12}$', -alkyl($C_0$-$C_6$)-$Cy_1$, or an oxo, $R_6$ represents —O-alkyl($C_1$-$C_6$)—$R_{11}$, $R_7$ represents a hydrogen atom, a halogen atom, a linear or branched ($C_1$-$C_6$)alkyl group, a linear or branched ($C_2$-$C_6$)alkenyl group, a linear or branched ($C_2$-$C_6$) alkynyl group, a linear or branched ($C_1$-$C_6$)polyhaloalkyl, a hydroxy group, a linear or branched ($C_1$-$C_6$) alkoxy group, a —S—($C_1$-$C_6$)alkyl group, a cyano group, a nitro group, -alkyl($C_0$-$C_6$)—$NR_{10}R_{10}$', —O-alkyl($C_1$-$C_6$)—$NR_{10}R_{10}$', —O-$Cy_1$, -alkyl($C_0$-$C_6$)-$Cy_1$, -alkenyl($C_2$-$C_6$)-$Cy_1$, -alkynyl($C_2$-$C_6$)-$Cy_1$, —O-alkyl($C_1$-$C_6$)—$R_{11}$, —C(O)—$OR_{10}$, —O—C(O)—$R_{10}$, —C(O)—$NR_{10}R_{10}$', —$NR_{10}$—C(O)—$R_{10}$', —$NR_{10}$—C(O)—$OR_{10}$', -alkyl($C_1$-$C_6$)—$NR_{10}$—C(O)—$R_{10}$', —$SO_2$—$NR_{10}R_{10}$', —$SO_2$-alkyl($C_1$-$C_6$), $R_8$ represents a hydrogen atom, a linear or branched ($C_1$-$C_8$)alkyl group, a —$CHR_aR_b$ group, an aryl group, a heteroaryl group, an arylalkyl($C_1$-$C_6$) group, or a heteroarylalkyl($C_1$-$C_6$) group, $R_9$ represents a linear or branched ($C_1$-$C_6$)alkyl group, a linear or branched ($C_2$-$C_6$)alkenyl group, a linear or branched ($C_2$-$C_6$)alkynyl group, -$Cy_3$, -alkyl($C_1$-$C_6$)-$Cy_3$, -alkenyl($C_2$-$C_6$)-$Cy_3$, -alkynyl($C_2$-$C_6$)-$Cy_3$, -$Cy_3$-$Cy_4$, -alkynyl($C_2$-$C_6$)—O-$Cy_3$, -$Cy_3$-alkyl($C_0$-$C_6$)—O- alkyl($C_0$-$C_6$)-$Cy_4$, a halogen atom, a cyano group, —C(O)—$R_{13}$, or —C(O)—$NR_{13}R_{13}'$, $R_{10}$ and $R_{10}'$ independently of one another represent a hydrogen atom, a linear or branched ($C_1$-$C_6$)alkyl group, -alkyl($C_0$-$C_6$)-$Cy_1$, or the substituents of the pair ($R_{10}$, $R_{10}'$) form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the nitrogen in question may be substituted by from 1 to 2 groups representing a hydrogen atom, or a linear or branched ($C_1$-$C_6$)alkyl group, and it being understood that one or more of the carbon atoms of the possible substituents, may be deuterated, $R_{11}$ represents -$Cy_5$-alkyl($C_0$-$C_6$)—O-alkyl($C_0$-$C_6$)-$Cy_6$, -$Cy_5$-alkyl($C_0$-$C_6$)-$Cy_6$, -$Cy_5$-alkyl($C_0$-$C_6$)—$NR_{12}$-alkyl($C_0$-$C_6$)-$Cy_6$, $R_{12}$, $R_{12}'$, $R_{13}$ and $R_{13}'$ independently of one another represent a hydrogen atom or an optionally substituted linear or branched ($C_1$-$C_6$)alkyl group, $R_{14}$ represents a hydrogen atom, a hydroxy group, or a hydroxy($C_1$-$C_6$)alkyl group, $R_a$ represents a hydrogen atom or a linear or branched ($C_1$-$C_6$)alkyl group, $R_b$ represents a —O—C(O)—O—$R_c$ group, a —O—C(O)—$NR_cR_c'$ group, or a —O—P(O)($OR_c$)$_2$ group, $R_c$ and $R_c'$ independently of one another represent a hydrogen atom, a linear or branched ($C_1$-$C_8$)alkyl group, a cycloalkyl group, a ($C_1$-$C_6$)alkoxy($C_1$-$C_6$) alkyl group, a ($C_1$-$C_6$)alkoxycarbonyl($C_1$-$C_6$)alkyl group, or the substituents of the pair ($R_c$, $R_c'$) form together with the nitrogen atom carrying them a non-aromatic ring composed of from 5 to 7 ring members, which may contain in addition to the nitrogen atom from 1 to 3 heteroatoms selected from oxygen and nitrogen, it being understood that the nitrogen in question may be substituted by a group representing a linear or branched ($C_1$-$C_6$)alkyl group, $Cy_1$, $Cy_2$, $Cy_3$, $Cy_4$ and $Cy_5$ independently of one another, represent a cycloalkyl group, a heterocycloalkyl group, an aryl group, or a heteroaryl group, $Cy_6$ represents

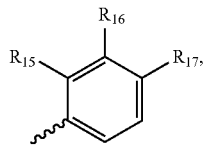

or $Cy_6$ represents a heteroaryl group which is substituted by a group selected from —O—P(O)($OR_{20}$)$_2$; —O—P(O)($O^-$)$_2$; —($CH_2$)$_p$—O—(CHR$_{18}$—CHR$_{19}$—O)$_q$—$R_{20}$; hydroxy; hydroxy($C_1$-$C_6$)alkyl; —($CH_2$)$_r$—Y—($CH_2$)$_s$-heterocycloalkyl; or —Y—($CH_2$)$_q$—$NR_{21}R_{21}'$, $R_{15}$ represents a hydrogen atom; a —($CH_2$)$_p$—O—(CHR$_{18}$—CHR$_{19}$—O)$_q$—$R_{20}$ group; a linear or branched ($C_1$-$C_6$)alkoxy($C_1$-$C_6$)alkyl group; a —Y—($CH_2$)$_q$—$NR_{21}R_{21}'$ group; or a —($CH_2$)$_r$—Y—($CH_2$)$_s$-heterocycloalkyl group, $R_{16}$ represents a hydrogen atom; a hydroxy group; a hydroxy($C_1$-$C_6$)alkyl group; a —($CH_2$)$_r$—Y—($CH_2$)$_s$-heterocycloalkyl group; a ($CH_2$)$_r$—Y—X—O—P(O)($OR_{20}$)$_2$ group; a —O—P(O)($O^-$)$_2$ group; a —($CH_2$)$_p$—O—(CHR$_{18}$—CHR$_{19}$—O)$_q$—$R_{20}$ group; a —($CH_2$)$_p$—O—C(O)—$NR_{22}R_{23}$ group; or a —Y—($CH_2$)$_q$—$NR_{21}R_{21}'$ group, $R_{17}$ represents a hydrogen atom; a —($CH_2$)$_p$—O—(CHR$_{18}$—CHR$_{19}$—O)$_q$—$R_{20}$ group; a —O—P(O)($OR_{20}$)$_2$ group; a —O—P(O)($O^-$)$_2$ group; a hydroxy group; a hydroxy($C_1$-$C_6$)alkyl group; a —($CH_2$)$_r$—Y—($CH_2$)$_s$-heterocycloalkyl group; a —Y—($CH_2$)$_q$—$NR_{21}R_{21}'$ group; or an aldonic acid, X represents a —($CH_2$)$_s$— group or a —C(O)— group, Y represents a bond or an oxygen atom, $R_{18}$ represents a hydrogen atom or a ($C_1$-$C_6$)alkoxy($C_1$-$C_6$)alkyl group, $R_{19}$ represents a hydrogen atom or a hydroxy($C_1$-$C_6$)alkyl group, $R_{20}$ represents a hydrogen atom or a linear or branched ($C_1$-$C_6$)alkyl group, $R_{21}$ and $R_{21}'$ independently of one another represent a hydrogen atom, a linear or branched ($C_1$-$C_6$)alkyl group, or a hydroxy($C_1$-$C_6$)alkyl group, or the substituents of the pair ($R_{21}$, $R_{21}'$) form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the resulting ring may be substituted by a group representing a hydrogen atom or a linear or branched ($C_1$-$C_6$) alkyl group, $R_{22}$ represents a ($C_1$-$C_6$)alkoxy($C_1$-$C_6$)alkyl group, a —($CH_2$)$_p$—$NR_{24}R_{24}'$ group, or a —($CH_2$)$_p$—O—(CHR$_{18}$—CHR$_{19}$—O)$_q$—$R_{20}$ group, $R_{23}$ represents a hydrogen atom or a ($C_1$-$C_6$)alkoxy($C_1$-$C_6$)alkyl group, or the substituents of the pair ($R_{22}$, $R_{23}$) form together with the nitrogen atom carrying them an aromatic or non-aromatic ring composed of from 5 to 18 ring members, which may contain in addition to the nitrogen atom from 1 to 5 heteroatoms selected from oxygen, sulphur and nitrogen, it being understood that the resulting ring may be substituted by a group representing a hydrogen atom, a linear or branched ($C_1$-$C_6$)alkyl group or a heterocycloalkyl group, $R_{24}$ and $R_{24}'$ independently of one another represent a hydrogen atom or a linear or branched ($C_1$-$C_6$)alkyl group, or the substituents of the pair ($R_{24}$, $R_{24}'$) form together with the nitrogen atom carrying them an aromatic or non-aromatic ring composed of from 5 to 7 ring members, which may contain in addition to the nitrogen atom from one to 3 heteroatoms selected from oxygen, sulphur and nitrogen, it being understood that the resulting ring may be substituted by a group representing a hydrogen atom or a linear or branched ($C_1$-$C_6$) alkyl group, n is an integer equal to 0 or 1, p is an integer equal to 0, 1 or 2, q is an integer equal to 1, 2, 3 or 4, r and s are independently an integer equal to 0 or 1, with the proviso that $R_{15}$, $R_{16}$ and $R_{17}$ cannot represent together a hydrogen atom and, when $R_1$ represents a methyl group, $R_{15}$ cannot represent a methoxyethoxy group, it being understood that:

"aryl" means a phenyl, naphthyl, biphenyl, indanyl or indenyl group,

"heteroaryl" means any mono- or bi-cyclic group composed of from 5 to 10 ring members, having at least one aromatic moiety and containing from 1 to 3 heteroatoms selected from oxygen, sulphur and nitrogen, "cycloalkyl" means any mono- or bi-cyclic non-aromatic carbocyclic group containing from 3 to 10 ring members, "heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, it being possible for the aryl, heteroaryl, cycloalkyl and heterocycloalkyl groups so defined and the alkyl, alkenyl, alkynyl, alkoxy groups, to be substituted by from 1 to 5 groups selected from optionally substituted linear or branched ($C_1$-$C_6$)alkyl, optionally substituted linear or branched ($C_2$-$C_6$)alkenyl group, optionally substituted linear or branched ($C_2$-$C_6$)alkynyl group, optionally substituted linear or branched ($C_1$-$C_6$)alkoxy, optionally substituted ($C_1$-$C_6$)alkyl-S—, hydroxy, oxo (or N-oxide where appropriate), nitro, cyano, —C(O)—OR', —O—C(O)—R', —C(O)—NR'R", —NR'R", —(C═NR')—OR", linear or branched ($C_1$-$C_6$)polyhaloalkyl, trifluoromethoxy, or halogen, it being understood that R' and R" independently of one another represent a hydrogen atom or an optionally substituted linear or branched ($C_1$-$C_6$) alkyl group, and it being understood that one or more of the carbon atoms of the preceding possible substituents, may be deuterated, their enantiomers, diastereoisomers and atropisomers, and addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Advantageously, at least one of the groups selected from $R_2$, $R_3$, $R_4$ and $R_5$ does not represent a hydrogen atom.

More especially, compounds of formula (I) to which preference is given are compounds wherein n is an integer equal to 1.

In another embodiment of the invention, an advantageous possibility consists of compounds of formula (I-a):

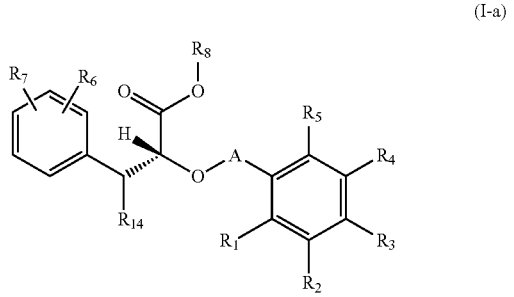

(I-a)

wherein $R_1$, $R_2$, $R_3$, $R_4$, $R_5$, $R_6$, $R_7$, $R_8$, $R_{14}$ and A are as defined for formula (I).

In the preferred compounds of the invention, $R_1$ represents a linear or branched ($C_1$-$C_6$)alkyl group or a halogen atom. More preferably, $R_1$ represents a methyl group, an ethyl group, a bromine atom or a chlorine atom.

Atropisomers are stereoisomers arising because of hindered rotation about a single bond, where energy differences due to steric strain or other contributors create a barrier to rotation that is high enough to allow for isolation of individual conformers. For compounds according to the invention, atropisomers are as follows:

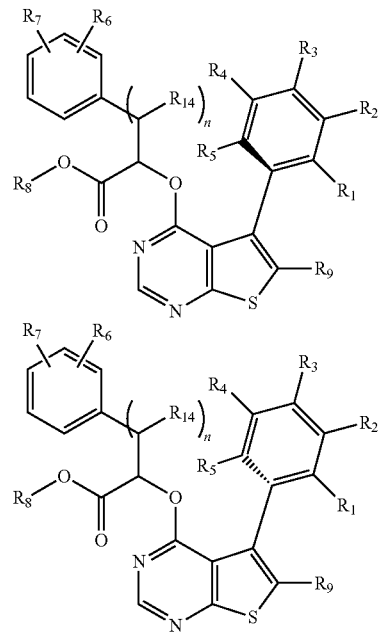

Preferred atropisomer is (5$S_a$).

Advantageously, $R_{14}$ represents a hydrogen atom, a hydroxy group, a hydroxymethyl group or a hydroxyethyl group. Preferably, $R_{14}$ represents a hydrogen atom.

Advantageously, $R_2$ represents a halogen atom, a hydroxy group, a linear or branched ($C_1$-$C_6$)alkoxy group. More preferably, $R_2$ represents a methoxy group, a hydroxy group, a fluorine atom, a bromine atom or a chlorine atom. Even more preferably, $R_2$ represents a chlorine atom.

$R_3$ advantageously represents a hydrogen atom, a hydroxy group, a linear or branched ($C_1$-$C_6$)alkoxy group or —O-alkyl($C_1$-$C_6$)—$NR_{10}R_{10}$'. Advantageously, $R_3$ represents —O-alkyl($C_1$-$C_6$)—$NR_{10}R_{10}$'.

In some preferred embodiment of the invention,

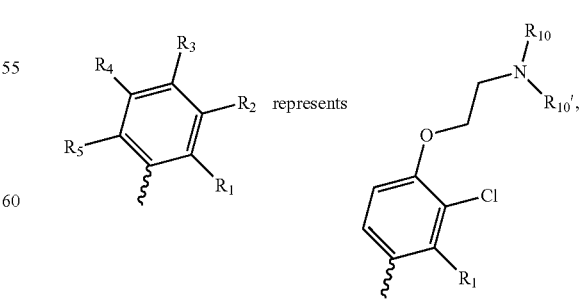

wherein $R_1$, $R_{10}$ and $R_{10}$' are as defined for formula (I).

In the preferred compounds of the invention,

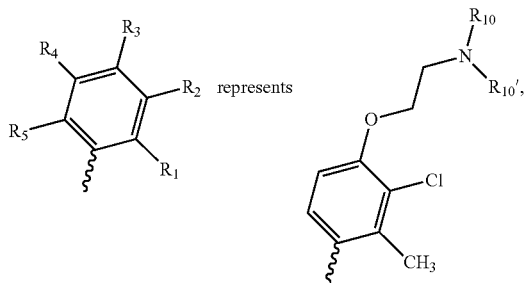

wherein $R_{10}$ and $R_{10}'$ are as defined for formula (I).

$R_4$ and $R_5$ preferably represent a hydrogen atom.

In an advantageous embodiment, the substituents of the pair ($R_1$, $R_5$) are identical and the substituents of the pair ($R_2$, $R_4$) are identical. In the preferred compounds of the invention, the substituents of the pair ($R_1$, $R_5$) are identical and represent a ($C_1$-$C_6$)alkyl group, preferably a methyl group, whereas the substituents of the pair ($R_2$, $R_4$) are identical and represent a halogen atom, preferably a chlorine atom, or a hydrogen atom.

In the preferred compounds of the invention,

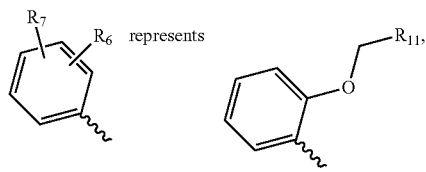

wherein $R_{11}$ is as defined for formula (I).

$R_7$ preferably represents a hydrogen atom.

Preferably, $R_8$ represents a hydrogen atom, a —$CHR_aR_b$ group, an optionally substituted linear or branched ($C_1$-$C_8$) alkyl group, or a heteroarylalkyl($C_1$-$C_6$) group. Preferably, $R_8$ represents a —$CHR_aR_b$ group in which $R_a$ represents a hydrogen atom or a methyl group and $R_b$ represents a —O—C(O)—O—($C_1$-$C_8$)alkyl group; a —O—C(O)—O-cycloalkyl group; a —O—C(O)—$NR_cR_c'$ group, in which $R_c$ and $R_c'$ independently of one another represent a hydrogen atom, a linear or branched ($C_1$-$C_8$)alkyl group, a ($C_1$-$C_6$)alkoxy($C_1$-$C_6$)alkyl group, a ($C_1$-$C_6$)alkoxycarbonyl($C_1$-$C_6$)alkyl group, or the substituents of the pair ($R_c$, $R_c'$) form together with the nitrogen atom carrying them a non-aromatic ring composed of from 5 to 7 ring members, which may contain in addition to the nitrogen atom from 1 to 3 heteroatoms selected from oxygen and nitrogen; or a —O—P(O)(OH)$_2$ group. Preferred $R_8$ groups are as follows: hydrogen; methyl; ethyl; (5-methyl-2-oxo-1,3-dioxol-4-yl)methyl; a —$CHR_aR_b$ group in which $R_a$ represents a methyl group and $R_b$ represents a —O—C(O)—O—$CH_2CH_3$ group or a —O—C(O)—N($CH_3$)$_2$ group. Even more preferably, $R_8$ represents hydrogen.

In the preferred compounds of the invention, $R_9$ represents a linear or branched ($C_1$-$C_6$)alkyl group, a linear or branched ($C_2$-$C_6$)alkenyl group, a linear or branched ($C_2$-$C_6$)alkynyl group, an aryl group or a heteroaryl group. Advantageously, $R_9$ represents a linear or branched ($C_2$-$C_6$) alkynyl group, an aryl group or a heteroaryl group. More preferably, $R_9$ represents a prop-1-yn-1-yl group, a but-1-yn-1-yl group, a phenyl group or a furan-2-yl group. In a more preferred embodiment, $R_9$ represents a 4-(benzyloxy)phenyl group, a 4-(pyridin-4-ylmethoxy)phenyl group, a 4-phenylbut-1-yn-1-yl group, a 4-fluorophenyl group or a 5-fluorofuran-2-yl group. Even more preferentially, $R_9$ represents a 4-fluorophenyl group.

In the preferred compounds of the invention, $R_{10}$ and $R_{10}'$ independently of one another represent a linear or branched ($C_1$-$C_6$)alkyl group, or the substituents of the pair ($R_{10}$, $R_{10}'$) form together with the nitrogen atom carrying them a non-aromatic ring composed of from 5 to 7 ring members, which may contain in addition to the nitrogen atom from 1 to 3 heteroatoms selected from oxygen, sulphur and nitrogen, it being understood that the nitrogen in question may be substituted by a group representing a hydrogen atom or a linear or branched ($C_1$-$C_6$)alkyl group. More preferably, $R_{10}$ and $R_{10}'$ represent a methyl group, or the substituents of the pair ($R_{10}$, $R_{10}'$) form together a 4-methyl-piperazinyl group or a 4-ethyl-piperazinyl group. In a more preferred embodiment, the substituents of the pair ($R_{10}$, $R_{10}'$) form together a 4-methyl-piperazinyl group. In another preferred embodiment, $R_{10}$ and $R_{10}'$ represent a methyl group.

Advantageously, $R_{11}$ represents -$Cy_5$-alkyl($C_0$-$C_6$)-$Cy_6$. More particularly, $R_{11}$ represents -$Cy_5$-$Cy_6$.

$Cy_5$ preferably represents a heteroaryl group, particularly, a pyrimidinyl group, a pyrazolyl group, a triazolyl group, a pyrazinyl group or a pyridinyl group. More preferably, $Cy_5$ represents a pyrimidin-4-yl group, a pyrazol-5-yl group, a triazol-5-yl group, a pyrazin-2-yl group or a pyridin-4-yl group. In the preferred compounds of the invention, $Cy_5$ represents a pyrimidin-4-yl group.

In another embodiment of the invention, $Cy_5$ represents a heteroaryl group which is substituted by an optionally substituted linear or branched ($C_1$-$C_6$)alkyl group, an optionally substituted linear or branched ($C_1$-$C_6$)alkoxy group, a —NR'R" group, or a linear or branched ($C_1$-$C_6$) polyhaloalkyl group, it being understood that R' and R" independently of one another represent a hydrogen atom or an optionally substituted linear or branched ($C_1$-$C_6$)alkyl group.

Preferably, $Cy_6$ represents

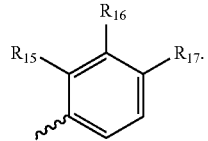

$Cy_6$ advantageously represents a 3-pyridinyl group, a 4-pyridinyl group, a pyridazin-4-yl group, a pyrazin-2-yl group, or a pyrimidin-4-yl group, it being understood that these heteroaryl groups are substituted by a group selected from —O—P(O)(O$R_{20}$)$_2$; —O—P(O)(O$^-$)$_2$; —(CH$_2$)$_p$—O—(CHR$_{18}$—CHR$_{19}$—O)$_q$—R$_{20}$; hydroxy($C_1$-$C_6$)alkyl; —(CH$_2$)$_r$—Y—(CH$_2$)$_s$-heterocycloalkyl; or —Y—(CH$_2$)$_q$—NR$_{21}$R$_{21}'$. More preferably, $Cy_6$ represents a 5-(hydroxymethyl)pyridin-3-yl group or a 2-(hydroxymethyl)pyrimidin-4-yl group.

Advantageously, $R_{16}$ and $R_{17}$ represent a hydrogen atom and $R_{15}$ represents a —(CH$_2$)$_p$—O—(CHR$_{18}$—CHR$_{19}$—O)$_q$—R$_{20}$ group; a linear or branched ($C_1$-$C_6$)alkoxy($C_1$-$C_6$) alkyl group; a —Y—(CH$_2$)$_q$—NR$_{21}$R$_{21}'$ group; or a —(CH$_2$)$_r$—Y—(CH$_2$)$_s$-heterocycloalkyl group, in which $R_{18}$, $R_{19}$, $R_{20}$, $R_{21}$, $R_{21}'$, Y, p, q, r and s are as defined for formula (I).

In the preferred compounds of the invention, $R_{15}$ and $R_{17}$ represent a hydrogen atom and $R_{16}$ represents a hydroxy group; a hydroxy($C_1$-$C_6$)alkyl group; a —$(CH_2)_r$—Y—$(CH_2)_s$-heterocycloalkyl group; a —O—P(O)($OR_{20})_2$ group; a —O—P(O)($O^-)_2$ group; a —$(CH_2)_p$—O—$(CHR_{18}$—$CHR_{19}$—O$)_q$—$R_{20}$ group; a —$(CH_2)_p$—O—C(O)—$NR_{22}R_{23}$ group; a $(CH_2)_r$Y—X—O—P(O)($OR_{20})_2$ group; or a —Y—$(CH_2)_q$—$NR_{21}R_{21}$' group, in which $R_{18}$, $R_{19}$, $R_{20}$, $R_{21}$, $R_{21}$', $R_{22}$, $R_{23}$, X, Y, p, q, r and s are as defined for formula (I).

In some preferred embodiment of the invention, $R_{15}$ and $R_{16}$ represent a hydrogen atom and $R_{17}$ represents a —$(CH_2)_p$—O—$(CHR_{18}$—$CHR_{19}$—O$)_q$—$R_{20}$ group; a —O—P(O)($OR_{20})_2$ group; a —O—P(O)($O^-)_2$ group; a hydroxy group; a hydroxy($C_1$-$C_6$)alkyl group; a —$(CH_2)_r$—Y—$(CH_2)_s$-heterocycloalkyl group; a —Y—$(CH_2)_q$—$NR_{21}R_{21}$' group; or an aldonic acid, in which $R_{18}$, $R_{19}$, $R_{20}$, $R_{21}$, $R_{21}$', Y, p, q, r and s are as defined for formula (I).

In a preferred embodiment of the invention, "heterocycloalkyl" as defined for $R_{15}$, $R_{16}$ and $R_{17}$ represents any mono- or bi-cyclic non-aromatic carbocyclic group containing from 3 to 10 ring members, and containing from 1 to 3 heteroatoms selected from oxygen, sulphur and nitrogen, it being understood that the resulting ring may be substituted by from 1 to 5 groups selected from linear or branched ($C_1$-$C_6$)alkyl, linear or branched ($C_1$-$C_6$)alkoxy, hydroxy, or hydroxy($C_1$-$C_6$)alkyl.

Advantageously, $R_{15}$ represents a —$(CH_2)_p$—O—$CH_2$—CH($CH_2OH$)—OH group; a —$(CH_2)_p$—O—$(CH_2$—$CH_2$—O$)_q$—H group; a —$(CH_2)_p$—O—$(CH_2$—$CH_2$—O$)_q$—$CH_3$ group; a methoxymethyl group; a (2,2-dimethyl-1,3-dioxolan-4-yl)methoxy group; a (2,2-dimethyl-1,3-dioxolan-4-yl)methoxymethyl group; or a —Y—$(CH_2)_q$—N($CH_2$—$CH_2$—OH$)_2$ group, in which Y, p and q are as defined for formula (I).

In the preferred compounds of the invention, $R_{16}$ represents a hydroxy group; a hydroxymethyl group; a (2,2-dimethyl-1,3-dioxolan-4-yl)methoxy group; a —O—P(O)(OH$)_2$ group; a —$(CH_2)_p$—O—$CH_2$—CH($CH_2OH$)—OH group; a —$(CH_2)_p$—O—$(CH_2$—$CH_2$—O$)_q$—H group; a —$(CH_2)_p$—O—$(CH_2$—$CH_2$—O$)_q$—$CH_3$ group, in which p and q are as defined for formula (I); a —O—CH($CH_2$—$OCH_3)_2$ group; a —$CH_2$—O—C(O)—$NR_{22}R_{23}$ group, in which $R_{22}$ is as defined for formula (I) and $R_{23}$ represents a hydrogen atom, or in which $R_{22}$ and $R_{23}$ represent a ($C_1$-$C_6$)alkoxy($C_1$-$C_6$)alkyl group, or in which the substituents of the pair ($R_{22}$, $R_{23}$) form together with the nitrogen atom carrying them a non-aromatic ring composed of from 5 to 18 ring members, which may contain in addition to the nitrogen atom from 1 to 5 heteroatoms selected from oxygen, sulphur and nitrogen, it being understood that the resulting ring may be substituted by a group representing a linear or branched ($C_1$-$C_6$)alkyl group or a heterocycloalkyl; a —O—$(CH_2)_2$—$NR_{21}R_{21}$' group; a —$CH_2$—$NR_{21}R_{21}$' group, in which $R_{21}$ and $R_{21}$' are as defined for formula (I); a $(CH_2)_r$—O—X—O—P(O)($OR_{20})_2$ group, in which X and r are as defined for formula (I), and s is integer equal to 1; or a —$(CH_2)_r$—Y—$(CH_2)_s$-heterocycloalkyl group, in which Y is a bond, r and s are integers equal to 0 and the heterocycloalkyl group represents an aldohexose of formula:

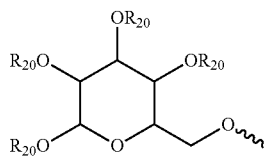

in which each $R_{20}$ is independent. More preferably, the heterocycloalkyl group represents an aldohexose of formula:

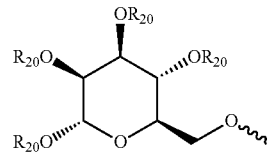

in which each $R_{20}$ is independent.

In some preferred embodiment of the invention, $R_{17}$ represents a hydroxy group; a hydroxymethyl group; a hydroxyethyl group; a —O—$(CH_2$—$CH_2$—O$)_q$—$CH_3$ group; a —O—$CH_2$—CH($CH_2OH$)—OH group; a —$(CH_2)_p$—O—$(CH_2$—$CH_2$—O$)_q$—H group; a —O—P(O)(OH$)_2$ group; a —O—P(O)($O^-)_2$ group; a —O—CH($CH_2$—$OCH_3)_2$ group; a —O—$(CH_2)_2$—$NR_{21}R_{21}$' group; a —$CH_2$—$NR_{21}R_{21}$' group, in which $R_{21}$ and $R_{21}$' are as defined for formula (I); a (2,2-dimethyl-1,3-dioxolan-4-yl)methoxy group; D-mannonic acid; or a —$(CH_2)_r$—Y—$(CH_2)_s$-heterocycloalkyl group in which Y is a bond, s is an integer equal to 0, r is as defined for formula (I) and the heterocycloalkyl group represents an aldohexose of formula:

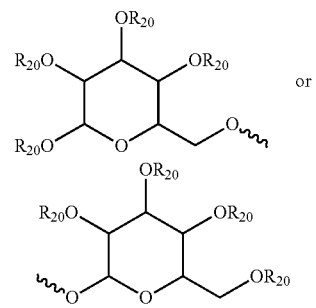

in which each $R_{20}$ is independent. More preferably, the heterocycloalkyl group represents an aldohexose of formula:

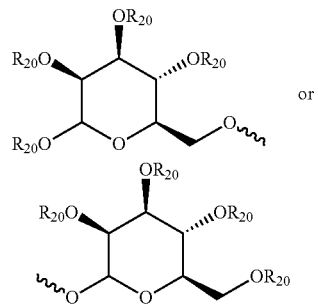

in which each $R_{20}$ is independent.

Among the preferred compounds of the invention there may be mentioned:
(2R)-2-{[(5$S_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-(2-{[2-(3-hydroxyphenyl)pyrimidin-4-yl]methoxy}phenyl)propanoic acid;
(2R)-2-{[(5$S_a$)-5-{3-chloro-2-methyl-4-[3-(4-methylpiperazin-1-yl)propoxy]phenyl}-6-(4-fluorophenyl)thieno

[2,3-d]pyrimidin-4-yl]oxy}-3-(2-{[2-(4-hydroxyphenyl)pyrimidin-4-yl]methoxy}phenyl)propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-[2-({2-[3-(hydroxymethyl)phenyl]pyrimidin-4-yl}methoxy)phenyl]propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-[2-({2-[4-(hydroxymethyl)phenyl]pyrimidin-4-yl}methoxy)phenyl]propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-{2-[(2-{2-[(2,2-dimethyl-1,3-dioxolan-4-yl)methoxy]phenyl}pyrimidin-4-yl)methoxy]phenyl}propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-{2-[(2-{2-[2-(2-methoxyethoxy)ethoxy]phenyl}pyrimidin-4-yl)methoxy]phenyl}propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-(2-{[2-(2-{2-[2-(2-methoxyethoxy)ethoxy]ethoxy}phenyl)pyrimidin-4-yl]methoxy}phenyl)propanoic acid;

(2R)-2-{[(5S$_a$-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-[2-({2-[2-(methoxymethyl)phenyl]pyrimidin-4-yl}methoxy)phenyl]propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-{2-[(2-{2-[(2-methoxyethoxy)methyl]phenyl}pyrimidin-4-yl)methoxy]phenyl}propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-{2-[(2-{2-[(2-hydroxyethoxy)methyl]phenyl}pyrimidin-4-yl)methoxy]phenyl}propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-(2-{[2-(2-{[(2,2-dimethyl-1,3-dioxolan-4-yl)methoxy]methyl}phenyl)pyrimidin-4-yl]methoxy}phenyl)propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-{2-[(2-{3-[(2-hydroxyethoxy)methyl]phenyl}pyrimidin-4-yl)methoxy]phenyl}propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-{2-[(2-{3-[(1,3-dimethoxypropan-2-yl)oxy]phenyl}pyrimidin-4-yl)methoxy]phenyl}propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-{2-[(2-{4-[(1,3-dimethoxypropan-2-yl)oxy]phenyl}pyrimidin-4-yl)methoxy]phenyl}propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-[2-({2-[4-(2,3-dihydroxypropoxy)phenyl]pyrimidin-4-yl}methoxy)phenyl]propanoic acid;

methyl 6-O-{3-[4-({2-[(2R)-2-carboxy-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}ethyl]phenoxy}methyl)pyrimidin-2-yl]phenyl}-α-D-mannopyranoside;

methyl 6-O-{3-[4-({2-[(2R)-2-carboxy-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}ethyl]phenoxy}methyl)pyrimidin-2-yl]phenyl}-2,3,4-tri-O-methyl-α-D-mannopyranoside;

methyl 6-O-{4-[4-({2-[(2R)-2-carboxy-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}ethyl]phenoxy}methyl)pyrimidin-2-yl]phenyl}-α-D-mannopyranoside;

methyl 6-O-{4-[4-({2-[(2R)-2-carboxy-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}ethyl]phenoxy}methyl)pyrimidin-2-yl]phenyl}-2,3,4-tri-O-methyl-α-D-mannopyranoside;

6-O-{4-[4-({2-[(2R)-2-carboxy-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}ethyl]phenoxy}methyl)pyrimidin-2-yl]phenyl}-D-mannopyranose;

6-O-{2-[4-({2-[(2R)-2-carboxy-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}ethyl]phenoxy}methyl)pyrimidin-2-yl]phenyl}-D-mannonic acid;

1,2-O-[(1R)-1-({4-[4-({2-[(2R)-2-carboxy-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}ethyl]phenoxy}methyl)pyrimidin-2-yl]benzyl}oxy)ethylidene]-β-D-mannopyranose;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-{2-[(2-{4-[(α-D-mannopyranosyloxy)methyl]phenyl}pyrimidin-4-yl)methoxy]phenyl}propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-[2-({2-[4-(2-hydroxyethyl)phenyl]pyrimidin-4-yl}methoxy)phenyl]propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-[2-({2-[2-(2,3-dihydroxypropoxy)phenyl]pyrimidin-4-yl}methoxy)phenyl]propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-[2-({2-[2-(2-hydroxyethoxy)phenyl]pyrimidin-4-yl}methoxy)phenyl]propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-{2-[(2-{2-[(2,3-dihydroxypropoxy)methyl]phenyl}pyrimidin-4-yl)methoxy]phenyl}propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-[2-({2-[3-(phosphonooxy)phenyl]pyrimidin-4-yl}methoxy)phenyl]propanoic acid;

4-[4-({2-[(2R)-2-carboxy-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]
oxy}ethyl]phenoxy}methyl)pyrimidin-2-yl]phenyl
phosphate;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-[2-({2-[3-(2-hydroxyethoxy)phenyl]pyrimidin-4-yl}methoxy)phenyl] propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-{2-[(2-{4-[2-(2-methoxyethoxy)ethoxy]phenyl}pyrimidin-4-yl)methoxy]phenyl}propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-{2-[(2-{4-[2-(2-hydroxyethoxy)ethoxy]phenyl}pyrimidin-4-yl)methoxy]phenyl}propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-(2-{[2-(4-{2-[2-(2-methoxyethoxy)ethoxy]ethoxy}phenyl)pyrimidin-4-yl]methoxy}phenyl)propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-{2-[(2-{4-[2-(dimethylamino)ethoxy]phenyl}pyrimidin-4-yl)methoxy]phenyl}propanoic acid;

(2R)-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}-3-{2-[(2-{3-[(2,2-dimethyl-1,3-dioxolan-4-yl)methoxy]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[3-(15-hydroxy-3-oxo-2,7,10,13-tetraoxa-4-azapentadec-1-yl)phenyl]pyrimidin-4-yl}methoxy)phenyl]propanoic acid;

(2R)-3-(2-{[2-(3-{[(1,4'-bipiperidin-1'-ylcarbonyl)oxy]methyl}phenyl)pyrimidin-4-yl]methoxy}phenyl)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3-{2-[2-(2-hydroxyethoxy)ethoxy]ethoxy}phenyl)pyrimidin-4-yl]methoxy}phenyl)propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[2-(2-hydroxyethoxy)ethoxy]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[2-(2-methoxyethoxy)ethoxy]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[({[2-(4-methylpiperazin-1-yl)ethyl]carbamoyl}oxy)methyl]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[({[2-(morpholin-4-yl)ethyl]carbamoyl}oxy)methyl]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[({[2-(dimethylamino)ethyl]carbamoyl}oxy)methyl]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[({[2-(pyrrolidin-1-yl)ethyl]carbamoyl}oxy)methyl]phenyl}pyrimidin-4-yl)methoxy]phenyl}propanoic acid;

(2R)-3-[2-({2-[3-({[bis(2-methoxyethyl)carbamoyl]oxy}methyl)phenyl]pyrimidin-4-yl}methoxy)phenyl]-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3-{[(1,4,7,10,13-pentaoxa-16-azacyclooctadecan-16-ylcarbonyl)oxy]methyl}phenyl)pyrimidin-4-yl]methoxy}phenyl)propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[3-(2,3-dihydroxypropoxy)phenyl]pyrimidin-4-yl}methoxy)phenyl]propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3-{2-[2-(2-methoxyethoxy)ethoxy]ethoxy}phenyl)pyrimidin-4-yl]methoxy}phenyl)propanoic acid;

(2R)-3-(2-{[2-(3-{2-[bis(2-hydroxyethyl)amino]ethoxy}phenyl)pyrimidin-4-yl]methoxy}phenyl)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid;

(2R)-2-{[(5S$_a$)-5-{2,3-dimethyl-4-[2-(4-methylpiperazin-1-yl)ethoxy]phenyl}-6-(4-fluorophenyl)thieno[2,3-d]pyrimidin-4-yl]oxy}-3-{2-[(2-{3-[({[2-(piperidin-1-yl)ethyl]carbamoyl}oxy)methyl]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[2-(morpholin-4-yl)ethoxy]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[2-(dimethylamino)ethoxy]phenyl}pyrimidin-4-yl)methoxy]phenyl}propanoic acid;

(2R)-3-(2-{[2-(4-{2-[bis(2-hydroxyethyl)amino]ethoxy}phenyl)pyrimidin-4-yl]methoxy}phenyl)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(4-{2-[2-(2-hydroxyethoxy)ethoxy]ethoxy}phenyl)pyrimidin-4-yl]methoxy}phenyl)propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{4-[(2,2-dimethyl-1,3-dioxolan-4-yl)methoxy]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{4-[2-(morpholin-4-yl)ethoxy]phenyl}pyrimidin-4-yl)methoxy]phenyl}propanoic acid;

4-[4-({2-[(2R)-2-carboxy-2-{[(5S$_a$)-5-{3-chloro-2-methyl-4-[3-(4-methylpiperazin-1-yl)propoxy]phenyl}-6-(4-fluorophenyl)thieno[2,3-d]pyrimidin-4-yl]oxy}ethyl]phenoxy}methyl)pyrimidin-2-yl]phenyl phosphate disodium salt;

1-[(ethoxycarbonyl)oxy]ethyl(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[(1,3-dimethoxypropan-2-yl)oxy]phenyl}pyrimidin-4-yl)methoxy]phenyl}propanoate;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[5-(hydroxymethyl)pyridin-3-yl]pyrimidin-4-yl}methoxy)phenyl]propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2'-(hydroxymethyl)-2,5'-bipyrimidin-4-yl]methoxy}phenyl)propanoic acid.

The invention relates also to a process for the preparation of compounds of formula (I), which process is characterised in that there is used as starting material the compound of formula (II):

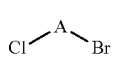
(II)

wherein A is as defined for formula (I) in which 1 is linked to the chlorine atom and 2 is linked to the bromine atom, which compound of formula (II) is subjected to coupling with a compound of formula (III):

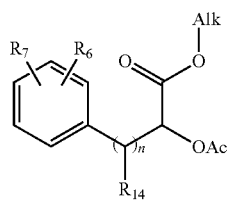
(III)

wherein R$_6$, R$_7$, R$_{14}$ and n are as defined for formula (I), and Alk represents a linear or branched (C$_1$-C$_6$)alkyl group,
to yield the compound of formula (IV):

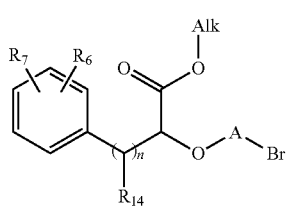
(IV)

wherein R$_6$, R$_7$, R$_{14}$, A and n are as defined for formula (I) and Alk is as defined before, compound of formula (IV) which is further subjected to coupling with compound of formula (V):

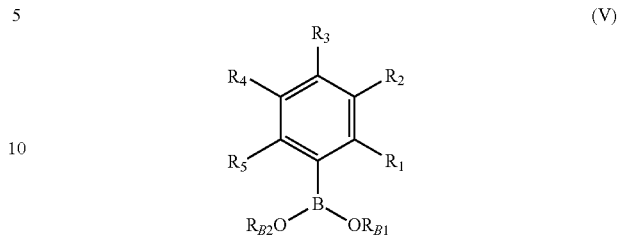
(V)

wherein R$_1$, R$_2$, R$_3$, R$_4$ and R$_5$ are as defined for formula (I), and R$_{B1}$ and R$_{B2}$ represent a hydrogen atom, a linear or branched (C$_1$-C$_6$) alkyl group, or R$_{B1}$ and R$_{B2}$ form with the oxygen carrying them an optionally methylated ring,
to yield the compound of formula (VI):

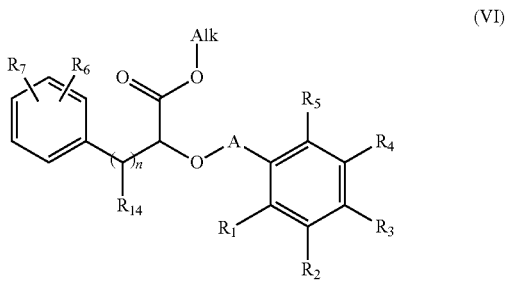
(VI)

wherein R$_1$, R$_2$, R$_3$, R$_4$, R$_5$, R$_6$, R$_7$, R$_{14}$, A and n are as defined for formula (I) and Alk is as defined before, the Alk-O—C(O)— ester function of which compound of formula (VI) is hydrolysed to yield the carboxylic acid, which may optionally be reacted with an alcohol of formula R$_8$'—OH or a chlorinated compound of formula R$_8$'—Cl wherein R$_8$' represents a linear or branched (C$_1$-C$_8$)alkyl group, a —CHR$_a$R$_b$ group, an aryl group, a heteroaryl group, an arylalkyl(C$_1$-C$_6$) group, or a heteroarylalkyl(C$_1$-C$_6$) group, R$_a$ and R$_b$ are as defined for formula (I), to yield the compound of formula (I), which may be purified according to a conventional separation technique, which is converted, if desired, into its addition salts with a pharmaceutically acceptable acid or base and which is optionally separated into its isomers according to a conventional separation technique, it being understood that at any moment considered appropriate during the course of the process described above, some groups (hydroxy, amino . . . ) of the starting reagents or of the synthesis intermediates can be protected, subsequently deprotected and functionalized, as required by the synthesis.

The compounds of formulae (II), (III), (V), R$_8$'—OH and R$_8$'—Cl are either commercially available or can be obtained by the person skilled in the art using conventional chemical reactions described in the literature.

Pharmacological study of the compounds of the invention has shown that they have pro-apoptotic properties. The ability to reactivate the apoptotic process in cancerous cells is of major therapeutic interest in the treatment of cancers and of immune and auto-immune diseases.

More especially, the compounds according to the invention will be useful in the treatment of chemo- or radio-resistant cancers.

Among the cancer treatments envisaged there may be mentioned, without implying any limitation, treatment of cancers of the bladder, brain, breast and uterus, chronic lymphoid leukaemias, cancer of the colon, oesophagus and liver, lymphoblastic leukaemias, acute myeloid leukaemias, lymphomas, melanomas, malignant haemopathies, myelomas, ovarian cancer, non-small-cell lung cancer, prostate cancer, pancreatic cancer and small-cell lung cancer.

The present invention relates also to pharmaceutical compositions comprising at least one compound of formula (I) in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration, especially tablets or drages, sublingual tablets, sachets, paquets, capsules, glossettes, lozenges, suppositories, creams, ointments, dermal gels, and drinkable or injectable ampoules.

The dosage varies according to the sex, age and weight of the patient, the administration route, the nature of the therapeutic indication, or of any associated treatments, and ranges from 0.01 mg to 1 g per 24 hours in one or more administrations.

Furthermore, the present invention relates also to the combination of a compound of formula (I) with an anticancer agent selected from genotoxic agents, mitotic poisons, anti-metabolites, proteasome inhibitors, kinase inhibitors and antibodies, and also to pharmaceutical compositions comprising that type of combination and their use in the manufacture of medicaments for use in the treatment of cancer.

Advantageously, the present invention relates to the combination of a compound of formula (I) with an EGFR inhibitor, and also to pharmaceutical compositions comprising that type of combination.

In another embodiment, the present invention relates to the combination of a compound of formula (I) with a mTOR/PI3K inhibitor, and also to pharmaceutical compositions comprising that type of combination.

In a preferred embodiment, the present invention relates to the combination of a compound of formula (I) with a MEK inhibitor, and also to pharmaceutical compositions comprising that type of combination.

Preferably, the present invention relates to the combination of a compound of formula (I) with a HER2 inhibitor, and also to pharmaceutical compositions comprising that type of combination.

Advantageously, the present invention relates to the combination of a compound of formula (I) with a RAF inhibitor, and also to pharmaceutical compositions comprising that type of combination.

In another embodiment, the present invention relates to the combination of a compound of formula (I) with a EGFR/HER2 inhibitor, and also to pharmaceutical compositions comprising that type of combination.

In a preferred embodiment, the present invention relates to the combination of a compound of formula (I) with a taxane, and also to pharmaceutical compositions comprising that type of combination.

In another embodiment, the present invention relates to the combination of a compound of formula (I) with a proteasome inhibitor, an immunomodulator or an alkylating agent, and also to pharmaceutical compositions comprising that type of combination.

The combination of a compound of formula (I) with an anticancer agent may be administered simultaneously or sequentially. The administration route is preferably the oral route, and the corresponding pharmaceutical compositions may allow the instantaneous or delayed release of the active ingredients. The compounds of the combination may moreover be administered in the form of two separate pharmaceutical compositions, each containing one of the active ingredients, or in the form of a single pharmaceutical composition, in which the active ingredients are in admixture.

The compounds of the invention may also be used in combination with radiotherapy in the treatment of cancer.

Finally, the compounds of the invention may be linked to monoclonal antibodies or fragments thereof or linked to scaffold proteins that can be related or not to monoclonal antibodies.

Antibody fragments must be understood as fragments of Fv, scFv, Fab, F(ab')2, F(ab'), scFv-Fc type or diabodies, which generally have the same specificity of binding as the antibody from which they are descended. According to the present invention, antibody fragments of the invention can be obtained starting from antibodies by methods such as digestion by enzymes, such as pepsin or papain, and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

Scaffold proteins that can be related or not to monoclonal antibodies are understood to mean a protein that contains or not an immunoglobulin fold and that yields a binding capacity similar to a monoclonal antibody. The man skilled in the art knows how to select the protein scaffold. More particularly, it is known that, to be selected, such a scaffold should display several features as follow (Skerra A., J. Mol. Recogn. 2000, 13, 167-187): phylogenetically good conservation, robust architecture with a well-known three-dimensional molecular organization (such as, for example, crystallography or NMR), small size, no or only a low degree of post-translational modifications, easy to produce, express and purify. Such a protein scaffold can be, but without limitation, a structure selected from the group consisting in fibronectin and preferentially the tenth fibronectin type III domain (FNfn10), lipocalin, anticalin (Skerra A., J. Biotechnol. 2001, 74(4):257-75), the protein Z derivative from the domain B of staphylococcal protein A, thioredoxin A or any protein with a repeated domain such as an "ankyrin repeat" (Kohl et al., PNAS 2003, 100(4), 1700-1705), "armadillo repeat", "leucine-rich repeat" or "tetratricopeptide repeat". There could also be mentioned a scaffold derivative from toxins (such as, for example, scorpion, insect, plant or mollusc toxins) or protein inhibitors of neuronal nitric oxide synthase (PIN).

The following Preparations and Examples illustrate the invention but do not limit it in any way.

General Procedures

All reagents obtained from commercial sources were used without further purification. Anhydrous solvents were obtained from commercial sources and used without further drying.

Flash chromatography was performed on ISCO Combi-Flash Rf 200i with pre-packed silica-gel cartridges (RediSep®R$_f$ Gold High Performance).

Thin layer chromatography was conducted with 5×10 cm plates coated with Merck Type 60 F254 silica-gel.

Microwave heating was performed in an Anton Parr MonoWave or CEM Discover® instrument.

Preparative HPLC purifications were performed on an Armen Spot Liquid Chromatography system with a Gemini-NX® 10 μM C18, 250 mm×50 mm i.d. column running at a flow rate of 118 mL min$^{-1}$ with UV diode array detection (210-400 nm) using 25 mM aqueous NH$_4$HCO$_3$ solution and MeCN as eluents unless specified otherwise.

Analytical LC-MS: The compounds of the present invention were characterized by high performance liquid chromatography-mass spectroscopy (HPLC-MS) on Agilent HP1200 with Agilent 6140 quadrupole LC/MS, operating in positive or negative ion electrospray ionisation mode. Molecular weight scan range is 100 to 1350. Parallel UV detection was done at 210 nm and 254 nm. Samples were supplied as a 1 mM solution in ACN, or in THF/H$_2$O (1:1) with 5 μL loop injection. LCMS analyses were performed on two instruments, one of which was operated with basic, and the other with acidic eluents. Basic LCMS: Gemini-NX, 3 μm, C18, 50 mm×3.00 mm i.d. column at 23° C., at a flow rate of 1 mL min$^{-1}$ using 5 mM ammonium bicarbonate (Solvent A) and acetonitrile (Solvent B) with a gradient starting from 100% Solvent A and finishing at 100% Solvent B over various/certain duration of time.

Acidic LCMS: ZORBAX Eclipse XDB-C18, 1.8 μm, 50 mm×4.6 mm i.d. column at 40° C., at a flow rate of 1 mL min$^{-1}$ using 0.02% v/v aqueous formic acid (Solvent A) and 0.02% v/v formic acid in acetonitrile (Solvent B) with a gradient starting from 100% Solvent A and finishing at 100% Solvent B over various/certain duration of time.

$^1$H-NMR measurements were performed on Bruker Avance III 500 MHz spectrometer and Bruker Avance III 400 MHz spectrometer, using DMSO-d$_6$ or CDCl$_3$ as solvent. $^1$H NMR data is in the form of delta values, given in part per million (ppm), using the residual peak of the solvent (2.50 ppm for DMSO-d$_6$ and 7.26 ppm for CDCl$_3$) as internal standard.

Splitting patterns are designated as: s (singlet), d (doublet), t (triplet), q (quartet), quint (quintet), m (multiplet), br s (broad singlet), dd (doublet of doublets), td (triplet of doublets), dt (doublet of triplets), ddd (doublet of doublet of doublets).

Combination gas chromatography and low resolution mass spectrometry were performed on Agilent 6850 gas chromatograph and Agilent 5975C mass spectrometer using 15 m×0.25 mm column with 0.25 μm HP-5MS coating and helium as carrier gas. Ion source: EI$^+$, 70 eV, 230° C., quadrupole: 150° C., interface: 300° C.

HRMS were determined on a Shimadzu IT-TOF, ion source temperature 200° C., ESI+/−, ionization voltage: (+−)4.5 kV. Mass resolution min. 10000.

Elementary analyses were performed on a Thermo Flash EA 1112 Elemental Analyzer.

LIST OF ABBREVIATIONS

| Abbreviation | Name |
|---|---|
| Ac | acetyl |
| AIBN | 2-[(1-cyano-1-methyl-ethyl)azo]-2-methyl-propanenitrile |
| AtaPhos | bis(di-tert-butyl(4-dimethylaminophenyl)phosphine)dichloropalladium(II) |
| DCM | methylene chloride |
| DIPA | diisopropylamine |
| DMF | dimethylformamide |
| DSC | N,N'-disuccinimidyl carbonate |
| eq. | equivalent |
| Et | ethyl |
| HMDS | hexamethyldisilazane |
| $^i$Pr | isopropyl |
| Me | methyl |
| MeCN | acetonitrile |
| NBS | N-bromosuccinimide |
| $^n$Bu | n-butyl |
| Ph | phenyl |
| PPh$_3$ | triphenylphosphine |
| r.t. | room temperature |
| $^t$Bu | tert-butyl |
| $^t$BuXPhos | 2-di(tert-butylphosphino)-2',4',6'-triisopropylbiphenyl |
| TEA | triethylamine |
| THF | tetrahydrofurane |

General Procedure I

Step A 1 eq. of Preparation 1, 2 eq. of the appropriate boronic acid derivative, 2 eq. cesium carbonate and 0.1 eq. bis(PPh$_3$) palladium(II) dichloride were placed in a flask. A mixture of 1,4-dioxane and water (4:1, 10 mL/mmol) was added and the resulting mixture was stirred at 60° C. under argon atmosphere until no further conversion was observed. The reaction mixture was diluted with brine and the pH was set to 6 with 2M aqueous HCl solution, and then extracted with DCM. The volatiles from the separated organic phase were evaporated under reduced pressure and the crude product was purified by flash chromatography using DCM and methanol as eluents.

Step B

The obtained intermediate was dissolved in dioxane-water 1:1 (10 mL/mmol) and 10 eq. LiOH×H$_2$O was added. The mixture was stirred at r.t. until no further conversion was observed. Then it was diluted with brine, neutralized with 2M aqueous HCl solution, extracted with DCM. The combined organic phases were dried over MgSO$_4$, filtered and the filtrate was concentrated under reduced pressure. The crude product was purified via preparative reversed phase chromatography using 5 mM aqueous NH$_4$HCO$_3$ solution and MeCN as eluents. The diastereoisomer eluting later was collected.

General Procedure II

Step A 1 eq. Preparation 2 or 1 eq. Preparation 3, 2 eq. of the appropriate alcohol (unless otherwise stated) and 2 eq. PPh$_3$ were dissolved in dry toluene (0.2M for the phenol). 2 eq. di-tert-butyl azodicarboxylate was added and the mixture was stirred at 60° C. under nitrogen until no further conversion was observed. The volatiles were evaporated under reduced pressure and the crude intermediate was purified via flash chromatography using ethyl acetate and methanol as eluents.

Step B

The obtained intermediate was dissolved in dioxane-water 1:1 (10 mL/mmol) and 10 eq. LiOH×H$_2$O was added. The mixture was stirred at r.t. until no further conversion was observed. Then it was diluted with brine, neutralized with 2M aqueous HCl solution, and extracted with DCM. The combined organic phases were dried over MgSO$_4$, filtered and the filtrate was concentrated under reduced pressure. The crude product was purified via preparative reversed phase chromatography using 5 mM aqueous NH$_4$HCO$_3$ solution and MeCN as eluents. The diastereoisomer eluting later was collected.

General Procedure III

Step A

To a solution of 1 eq. Preparation 5 in dry acetonitrile (15 mL/mmol) 1.5 eq. DSC and 3 eq. TEA was added and the mixture was stirred for one hour at r.t. To the resulting mixture 2 eq. of the appropriate amine was added and was further stirred for 1 hour at r.t. The reaction mixture was injected directly onto a flash silica column (160 g/mmol, conditioned with EtOAc) and chromatographied using EtOAc and MeOH (containing 1.2% NH$_3$) as eluents.

Step B

The product of Step A was dissolved in dioxane-water (1:1, 10 mL/mmol) and 10 eq. LiOH×H$_2$O was added. The mixture was stirred at r.t. until no further conversion was observed. Then it was neutralized with 2M HCl and directly injected onto an RP18 column and chromatographied using 5 mM aqueous NH$_4$HCO$_3$ solution and MeCN as eluents. The diastereomer eluting later was collected.

General Procedure IV

Step A 1 eq. of the appropriate phenol derivative, 2 eq. of the appropriate alcohol derivative, and 2 eq. PPh$_3$ were dissolved in dry toluene (0.2M for the phenol) under N$_2$ atmosphere then 2 eq. di-tert-butyl azodicarboxylate was added and the mixture was stirred at 60° C. until no further conversion was observed. The reaction mixture was concentrated under reduced pressure and the residue was purified via flash chromatography using heptane and EtOAc as eluents.

Step B 1 eq. of the phenol derivative obtained in Step A was dissolved in dry THF. The solution was cooled to −78° C. under argon and then 1.2 eq. "BuLi (1.6M in hexane) was added dropwise. After 15 minutes, 1.5 eq. 2-isopropoxy-4,4,5,5-tetramethyl-1,3,2-dioxaborolane was added dropwise. The cooling bath was removed and the mixture was slowly allowed to warm up to r.t. Then the mixture was quenched with NH$_4$Cl solution and extracted with EtOAc. The combined organic layers were concentrated under reduced pressure and the crude product was purified via flash chromatography using heptane and EtOAc as eluents.

General Procedure V 1 eq. Preparation 1, 3 eq. the appropriate boronic acid derivative, 4.5 eq. cesium carbonate and 0.15 eq. bis(PPh$_3$) palladium(II) dichloride in dioxane (30 mL/mmol) and water (15 mL/mmol) were stirred under N$_2$ atmosphere at 60° C. until no further conversion was observed. The reaction mixture was cooled to r.t., then 20 eq. LiOH×H$_2$O (832 mg/mmol) was added and the mixture was stirred until no further conversion was observed. The reaction mixture was diluted with brine, the pH was adjusted to 6 using 1M HCl, then the mixture was filtered and the precipitate was washed with dioxan. The volatiles of the filtrate were evaporated under reduced pressure and the residue was purified via preparative reversed phase chromatography using 25 mM aqueous NH$_4$HCO$_3$ solution and MeCN as eluents.

Preparation 1

Ethyl (2R)-2-[5-[3-chloro-2-methyl-4-[2-(4-methyl-piperazin-1-yl) ethoxy]phenyl]-6-(4-fluorophenyl) thieno[2,3-d]pyrimidin-4-yl]oxy-3-[2-[(2-chloro pyrimidin-4-yl)methoxy]phenyl]propanoate Step A: 6-Iodo-3H-thieno[2,3-d]pyrimidin-4-one A 2 L round bottomed flask equipped with mechanical stirrer, thermometer and reflux condenser was charged with the solution of 433 mL acetic acid, 13 mL sulfuric acid and 87 mL water. 69.3 g 3H-thieno[2,3-d]pyrimidin-4-one (0.46 mol), 51.9 g periodic acid (0.23 mol) and 104 g iodine (0.41 mol) were added to the stirred solution heated to 60° C. for 1 hour. The resulting suspension was cooled to r.t., filtered off, washed with a mixture of acetic acid and water (5:1) and then with diethyl ether. The resulting beige crystalline solid was air dried to give 6-iodo-3H-thieno[2,3-d]pyrimidin-4-one. $^1$H NMR (500 MHz, DMSO-d$_6$) δ 12.57 (br s, 1H), 8.09 (s, 1H), 7.65 (s, 1H) $^{13}$C NMR (125 MHz, DMSO-d$_6$) δ 168.3, 155.9, 146.1, 130.8, 126.7, 76.4

Step B: 4-Chloro-6-iodo-thieno[2,3-d]pyrimidine

A 1 L round bottomed flask equipped with mechanical stirrer, thermometer, reflux condenser and a CaCl$_2$-tube was charged with 113 mL phosphorous oxychloride and 35 mL N,N-dimethylaniline (0.29 mol). 75.54 g 6-iodo-3H-thieno [2,3-d]pyrimidin-4-one (from Step A) (0.27 mol) was added to the mixture in portions during 5 minutes. The reaction mixture was stirred at 105° C. for 1 hour. The resulting suspension was cooled to 10° C., filtered and washed with hexane. The crude product was added to ice water and stirred for 10 minutes, filtered off, washed with cold water, diethyl ether and air dried to give 4-chloro-6-iodo-thieno[2,3-d] pyrimidine as a beige crystalline solid. $^1$H NMR (500 MHz, DMSO-d$_6$) δ 8.89 (s, 1H), 7.98 (s, 1H) $^{13}$C NMR (125 MHz, DMSO-d$_6$) δ 172.3, 152.9, 151.9, 131.1, 128.9, 86.5

Step C: 5-Bromo-4-chloro-6-iodo-thieno[2,3-d]pyrimidine

A 2 L round bottomed flask equipped with mechanical stirrer, thermometer and a bubbler was charged with 600 mL MeCN. 84.9 g 4-chloro-6-iodo-thieno[2,3-d]pyrimidine (from Step B) (0.29 mol), 50.9 g NBS (0.29 mol) and 8.5 mL tetrafluoroboric acid diethyl ether complex were added. The reaction mixture was stirred at r.t. for 16 hours. Further 22.9 g (0.12 mol) NBS was added to the mixture in three portions. After cooling the suspension to 0° C. and stirring for further 1 hour the precipitate was filtered off, washed with acetonitrile and air dried to give 5-bromo-4-chloro-6-iodo-thieno [2,3-d]pyrimidine as beige crystalline solid. $^1$H NMR (400 MHz, DMSO-d$_6$) δ 8.88 (s, 1H) $^{13}$C NMR (100 MHz, DMSO-d$_6$) δ 171.3, 152.9, 152.3, 126.0, 112.4, 92.9

Step D: 5-Bromo-4-chloro-6-(4-fluorophenyl)thieno [2,3-d]pyrimidine 75.08 g 5-bromo-4-chloro-6-iodo-thieno[2,3-d]pyrimidine (from Step C) (200 mmol), 53.63 g 2-(4-fluorophenyl)-4,4,5,5-tetramethyl-1,3,2-dioxaborolane (240 mmol), 130 g cesium carbonate (400 mmol), 2.245 g Pd(OAc)$_2$ (10 mmol) and 8.50 g $^t$BuXPhos (20 mmol) were placed in a 2 L flask. 600 mL THF and 200 mL water were added, and then stirred overnight at 70° C. under argon atmosphere. THF was evaporated, and then the product was collected by filtration. Crude product was sonicated in 250 mL MeCN and filtered again. Then 5-bromo-4-chloro-6-(4-fluorophenyl)thieno[2, 3-d]pyrimidine was crystallized from EtOH/THF (2:1). $^1$H NMR (400 MHz, DMSO-d$_6$): 9.02 (s, 1H), 7.80-7.77 (m, 2H), 7.47-7.43 (m, 2H)

Step E: [2-(Bromomethyl)phenyl]acetate 60.07 g 2-methylphenyl acetate (400 mmol) and 106.8 g NBS (600 mmol) were placed in a 1 L flask. 500 mL cyclohexane was added, and then with intensive stirring 3.284 g AIBN (20 mmol) was added over 30 minutes. The mixture was stirred at 80° C. until no further conversion was observed, then cooled to r.t. The precipitate was filtered off and washed with cyclohexane. The mother liquor was concentrated under reduced pressure, and the crude product was used in Step B without further purification.

Step F: Ethyl 2-acetoxy-3-(2-hydroxyphenyl)propanoate 23.10 g anhydrous LiCl (545 mmol) and 65.36 g anhydrous $ZnCl_2$ (479.6 mmol) were placed in a 2 L flask, then dried at 160° C. under 0.1 mmHg for 1 hour. After cooling to r.t. under argon atmosphere, 26.49 g magnesium turnings (1090 mmol) and 1 L dry pre-cooled (0° C.) THF were added. The resulting mixture was immersed into an ice-bath, and then stirred for 30 minutes.

100 g [2-(bromomethyl)phenyl]acetate (from Step E) (~436 mmol) was dissolved in 120 mL dry THF and was added to the precooled inorganics over 15 minutes. After addition of the reagent the resulting mixture was stirred for 45 minutes while keeping the temperature between 0-5° C. To the mixture 64.82 mL ethyl 2-oxoacetate (654 mmol, 50% in toluene) was added over 5 minutes and the resulting mixture was stirred for another 15 minutes.

From the mixture the remaining inorganics were removed by filtration, and then 500 mL MeOH was added to the filtrate. This mixture was stirred until the intramolecular acetyl group migration from the phenolic oxygen to the alkyl oxygen was completed. To the mixture 30 mL acetic acid was added then the volatiles were evaporated under reduced pressure. To the residue 350 mL water was added and it was extracted with EtOAc. The combined organic layers were washed with saturated $NaHCO_3$ and with brine, and then dried over $MgSO_4$, filtered and evaporated under reduced pressure. To the residue 100 mL hexane was added and it was stirred for 30 minutes at 0° C. The formed white crystals were collected by filtration and washed with hexane yielding ethyl 2-acetoxy-3-(2-hydroxyphenyl)-(rac). $^1$H NMR (500 MHz, DMSO-$d_6$) δ 9.53 (s, 1H), 7.06 (t, 1H), 7.04 (d, 1H), 6.79 (d, 1H), 6.71 (t, 1H), 5.10 (dd, 1H), 4.05 (q, 2H), 3.06 (dd, 1H), 2.94 (dd, 1H), 2.00 (s, 3H), 1.09 (t, 3H)

Step G: Ethyl (2R)-2-acetoxy-3-(2-hydroxyphenyl) propanoate and ethyl (2S)-2-acetoxy-3-(2-hydroxyphenyl)propanoate Enantiomers of ethyl 2-acetoxy-3-(2-hydroxyphenyl)propanoate (from Step F) were separated via chiral chromatography. Column: OD; Eluents: heptane/EtOH; the enantiomer eluting earlier was collected as ethyl (2S)-2-acetoxy-3-(2-hydroxyphenyl) propanoate with 99.8% ee and the enantiomer eluting later was collected as ethyl (2R)-2-acetoxy-3-(2-hydroxyphenyl)propanoate with 99.9% ee.

Step H: (4-Bromo-2-chloro-phenoxy)-trimethyl-silane 20.8 g 4-bromo-2-chloro-phenol (100 mmol) was dissolved in 150 mL dry THF then 24.2 g HMDS (150 mmol) was added. The reaction mixture was stirred at 85° C. under argon atmosphere for 1.5 hours then concentrated under reduced pressure resulting in the product used without further purification. $^1$H NMR (200 MHz, $CDCl_3$): 7.49 (d, 1H), 7.23 (dd, 1H), 6.75 (d, 1H), 0.26 (s, 9H)

Step I: 4-Bromo-2-chloro-3-methyl-phenol 48 mL "BuLi solution in hexanes (2.5M, 120 mmol) was added dropwise to a solution of 12.1 g dry DIPA (120 mmol) in 250 mL dry THF at −78° C. under argon atmosphere. The mixture was stirred for 30 minutes at the same temperature then 28.0 g (4-bromo-2-chloro-phenoxy)-trimethyl-silane (from Step H) (100 mmol) was added dropwise. After 2.5 hours 21.3 g MeI (150 mmol) was added dropwise then the cooling bath was removed and the mixture was stirred overnight. The reaction was quenched with 100 mL $NH_4OH$ solution and 200 mL $NH_4Cl$ solution and extracted with EtOAc, dried over $Na_2SO_4$, filtered and concentrated under reduced pressure. The resulting dark mass was refluxed with pure hexane several times (150-150 mL aliquots) and decanted leaving a black tar behind. Combined organic phases were concentrated under reduced pressure affording 19.0 g 4-bromo-2-chloro-3-methyl-phenol, the crude product used without further purification. $^1$H NMR (200 MHz, $CDCl_3$): 7.32 (d, 1H), 6.76 (d, 1H), 5.62 (s, 1H), 2.49 (s, 3H)

Step J. (4-Bromo-2-chloro-3-methyl-phenoxy)-trimethyl-silane 20.8 g HMDS (129 mmol) was added to the solution of 19.0 g 4-bromo-2-chloro-3-methyl-phenol (from Step I) (86.0 mmol) in 150 mL dry THF. The mixture was stirred at 85° C. under argon balloon for 1.5 hours and then concentrated under reduced pressure. The obtained (4-bromo-2-chloro-3-methyl-phenoxy)-trimethyl-silane was used without further purification. $^1$H NMR (200 MHz, $CDCl_3$): 7.30 (d, 1H), 6.63 (d, 1H), 2.50 (s, 3H), 0.28 (s, 9H)

Step K: 2-Chloro-3-methyl-4-(4,4,5,5-tetramethyl-1,3,2-dioxaborolan-2-yl)phenol

A solution of 25.2 g (4-bromo-2-chloro-3-methyl-phenoxy)-trimethyl-silane (from Step J) (86.0 mmol) in 250 mL dry THF was cooled to −78° C. under argon and then 38 mL "BuLi in hexanes (2.5M, 94.6 mmol) was added dropwise. After 5 minutes, 19.2 g 2-isopropoxy-4,4,5,5-tetramethyl-1,3,2-dioxaborolane (103 mmol) was added dropwise. The cooling bath was removed and the mixture was slowly allowed to warm up to r.t. Then the mixture was added to 200 mL $NH_4Cl$ solution and extracted with EtOAc. Combined organic layers were concentrated under reduced pressure and passed through a pad of silica gel using hexane and EtOAc as eluents. The crude product was recrystallized from a mixture of EtOAc and hexane to obtain 2-chloro-3-methyl-4-(4,4,5,5-tetramethyl-1,3,2-dioxaborolan-2-yl) phenol. $^1$H NMR (500 MHz, DMSO-$d_6$): 10.40 (s, 1H), 7.42 (d, 1H), 6.80 (d, 1H), 2.49 (s, 3H), 1.27 (s, 12H)

Step L: 1-[2-[2-Chloro-3-methyl-4-(4,4,5,5-tetramethyl-1,3,2-dioxaborolan-2-yl)phenoxy]ethyl]-4-methyl-piperazine 10.0 g 2-chloro-3-methyl-4-(4,4,5,5-tetramethyl-1,3,2-dioxaborolan-2-yl)phenol (from Step K) (37.2 mmol), 8.7 g 2-(4-methylpiperazin-1-yl)ethanol (60.3 mmol) and 15.8 g $PPh_3$ (60.3 mmol) were dissolved in 100 mL dry toluene and then 27 mL diethyl azodicarboxylate (60.3 mmol, 40% solution in toluene) was added dropwise. The mixture was stirred at 50° C. under argon for 1.5 hours. The volatiles were evaporated under reduced pressure and 100 mL $Et_2O$ was added. The precipitated white crystals were filtered off and washed with $Et_2O$. The filtrate was concentrated under reduced pressure and purified via flash chromatography using CHCl$_3$ and MeOH as eluents. The resulting light brown oil was crystallized from hexane to give 1-[2-[2-chloro-3-methyl-4-(4,4,5,5-tetramethyl-1,3,2-dioxaborolan-2-yl)phenoxy]ethyl]-4-methyl-piperazine as an off-white solid. $^1$H NMR (500 MHz, DMSO-d$_6$): 7.56 (d, 1H), 6.99 (d, 1H), 4.15 (t, 2H), 2.72 (t, 2H), 2.51 (s, 3H), 2.50 (br s, 4H), 2.29 (br s, 4H), 2.13 (s, 3H), 1.29 (s, 12H)

Step M: Ethyl (2R)-2-acetoxy-3-[2-[(2-chloropyrimidin-4-yl)methoxy]phenyl]propanoate 9.06 g ethyl (2R)-2-acetoxy-3-(2-hydroxyphenyl)propanoate (from Step G, 36 mmol), 7.12 g 2-chloro-4-(chloromethyl)pyrimidine (44 mmol), 5.97 g K$_2$CO$_3$ (44 mmol) and 1.22 g KI (1.22 mmol) were placed in a 250 mL flask. 70 mL DMF was added and the mixture was stirred at r.t. under N$_2$ until no further conversion was observed. Then the reaction mixture was diluted with water and then it was extracted with EtOAc. The combined organic layers were dried over Na$_2$SO$_4$, filtered and concentrated under reduced pressure. The crude product was purified via flash chromatography using heptane and EtOAc as eluents to give ethyl (2R)-2-acetoxy-3-[2-[(2-chloropyrimidin-4-yl)methoxy]phenyl]propanoate. $^1$H NMR (500 MHz, DMSO-d$_6$) δ 8.86 (d, 1H), 7.69 (d, 1H), 7.25 (td, 1H), 7.23 (dd, 1H), 7.03 (d, 1H), 6.95 (td, 1H), 5.30 (d, 1H), 5.25 (d, 1H), 5.16-5.13 (m, 1H), 4.07 (qm, 2H), 3.28 (dd, 1H), 3.09 (dd, 1H), 2.00 (s, 3H), 1.09 (t, 3H)

Step N: Ethyl (2R)-3-[2-[(2-chloropyrimidin-4-yl)methoxy]phenyl]-2-hydroxy-propanoate 8.568 g ethyl (2R)-2-acetoxy-3-[2-[(2-chloropyrimidin-4-yl)methoxy]phenyl]propanoate (from Step M) (23 mmol) was dissolved in 100 mL ethanol, then 1.8 mL sodium ethoxide solution (1.0M in ethanol) was added and it was stirred until no further conversion was observed. The reaction mixture was diluted with water and it was extracted with ethyl acetate. The combined organics were dried over Na$_2$SO4, filtered and concentrated under reduced pressure. The crude product was purified via flash chromatography using heptane and EtOAc as eluents to give ethyl (2R)-3-[2-[(2-chloropyrimidin-4-yl)methoxy]phenyl]-2-hydroxy-propanoate. $^1$H NMR (500 MHz, DMSO-d$_6$) δ 8.84 (d, 1H), 7.70 (d, 1H), 7.20 (m, 1H), 7.19 (dm, 1H), 7.00 (dm, 1H), 6.91 (m, 1H), 5.52 (d, 1H), 5.27 (d, 1H), 5.24 (d, 1H), 4.06 (m, 1H), 4.04 (m, 1H), 3.13 (dd, 1H), 2.84 (dd, 1H), 1.11 (t, 3H)

Step O: Preparation 1

17.18 g 5-bromo-4-chloro-6-(4-fluorophenyl)thieno[2,3-d]pyrimidine (from Step D, 50 mmol) and 18.52 g ethyl (2R)-3-[2-[(2-chloropyrimidin-4-yl)methoxy]phenyl]-2-hydroxy-propanoate (from Step N, 55 mmol) were dissolved in 250 mL dry THF, then 48.87 g Cs$_2$CO$_3$ (150 mmol) was added and the mixture was stirred at 70° C. under N$_2$ until no further conversion was observed. Reaction mixture was cooled down to r.t., then 2.17 g 1-[2-[2-chloro-3-methyl-4-(4,4,5,5-tetramethyl-1,3,2-dioxaborolan-2-yl)phenoxy] ethyl]-4-methyl-piperazine (from Step L, 55 mmol), 560 mg AtaPhos (2.5 mmol) and 250 mL H$_2$O were added, and the mixture was stirred under nitrogen at 70° C. until no further conversion was observed. Then it was diluted with EtOAc and brine. After phase separation the aqueous phase was extracted with EtOAc. The organic layers were combined and dried over Na$_2$SO$_4$, filtered and concentrated under reduced pressure. The product was separated via flash chromatography using EtOAc and MeOH (containing 1.2% NH$_3$) as eluents. Preparation 1 was obtained as a mixture of the atropisomers. $^1$H NMR (500 MHz, DMSO-d$_6$) δ 8.87 (dd, 1H), 8.60 (s, 1H), 7.69 (dd, 1H), 7.35-7.26 (m, 2H), 7.22 (t, 2H), 7.20-7.10 (m, 2H), 7.02-6.91 (m, 1H), 6.87 (d, 1H), 6.72 (t, 1H), 6.15 (d, 1H), 5.47 (dd, 1H), 5.22 (s, 2H), 4.29-4.11 (m, 2H), 4.10-4.00 (m, 2H), 3.15-2.15 (br s, 8H), 3.13 (dd, 2H), 2.73-2.65 (m, 2H), 2.09 (s, 3H), 1.86 (s, 3H), 1.06 (t, 3H) (M+2H)$^{2+}$=416.1197

Preparation 2

Ethyl (2R)-2-[5-[3-chloro-2-methyl-4-[2-(4-methyl-piperazin-1-yl) ethoxy]phenyl]-6-(4-fluorophenyl) thieno[2,3-d]pyrimidin-4-yl]oxy-3-[2-[[2-(3-hydroxyphenyl)pyrimidin-4-yl]methoxy]phenyl] propanoate Using General Procedure I Step A and 3-(4,4,5,5-tetramethyl-1,3,2-dioxaborolan-2-yl)phenol as the appropriate boronic acid derivative, Preparation 2 was obtained as a mixture of the diastereoisomers. 1H NMR (500 MHz, DMSO-d6) δ 9.65 (br s, 1H), 8.95 (d, 1H), 8.58 (s, 1H), 7.88-7.80 (m, 2H), 7.57 (d, 1H), 7.33 (d, 1H), 7.32-7.27 (m, 2H), 7.3 (t, 1H), 7.24-7.14 (m, 4H), 7.05 (d, 1H), 6.94-6.90 (dm, 1H), 6.78-6.73 (tm, 1H), 6.30 (dd, 1H), 5.51 (dd, 1H), 5.30 (d, 1H), 5.24 (d, 1H), 4.26-4.00 (m, 4H), 3.17 (dd, 1H), 2.76 (br s, 2H), 2.58 (dd, 1H), 2.42 (br s, 3H), 3.00-2.30 (br s, 8H), 1.86 (s, 3H), 1.06 (t, 3H) (M+2H)$^{2+}$=445.1524

Preparation 3

Ethyl (2R)-2-[5-[3-chloro-2-methyl-4-[2-(4-methyl-piperazin-1-yl) ethoxy]phenyl]-6-(4-fluorophenyl) thieno[2,3-d]pyrimidin-4-yl]oxy-3-[2-[[2-(4-hydroxyphenyl pyrimidin-4-yl]methoxy]phenyl] propanoate Using General Procedure I Step A and 4-(4,4,5,5-tetramethyl-1,3,2-dioxaborolan-2-yl)phenol as the appropriate boronic acid derivative, Preparation 3 was obtained as a mixture of the diastereoisomers. $^1$H NMR (500 MHz, DMSO-d$_6$) δ 10.01 (s, 1H), 8.86 (d, 1H), 8.58 (s, 1H), 8.24 (d, 2H), 7.46 (d, 1H), 7.33 (d, 1H), 7.32-7.27 (m, 2H), 7.21 (t, 2H), 7.21-7.15 (m, 2H), 7.04 (d, 1H), 6.87 (d, 2H), 6.74 (t, 1H), 6.29 (d, 1H), 5.52 (dd, 1H), 5.26 (d, 1H), 5.20 (d, 1H), 4.19 (br s, 2H), 4.10-4.00 (m, 2H), 3.16 (dd, 1H), 3.03-2.41 (m, 13H), 2.56 (dd, 1H), 1.86 (s, 3H), 1.05 (t, 3H) (M+2H)$^{2+}$=445.1517

Preparation 4a:

2-[2-[(2,2-dimethyl-1,3-dioxolan-4-yl)methoxy]phenyl]-4,4,5,5-tetramethyl-1,3,2-dioxaborolane Using General Procedure IV, 2-iodophenol as the appropriate phenol and (2,2-dimethyl-1,3-dioxolan-4-yl)methanol as the appropriate alcohol, Preparation 4a was obtained. $^1$H NMR (500 MHz, DMSO-d$_6$) δ 7.50 (dd, 1H), 7.41 (tm, 1H), 6.98 (d, 1H), 6.93 (td, 1H), 4.37-4.31 (m, 1H), 4.08-4.02 (m, 2H), 4.03 (dd, 1H), 3.96 (dd, 1H), 1.36 (s, 3H), 1.30 (s, 3H), 1.27 (s, 12H)

Preparation 4b

2-[2-[2-(2-methoxyethoxy)ethoxy]phenyl]-4,4,5,5-tetramethyl-1,3,2-dioxaborolane Using General Procedure IV, 2-iodophenol as the appropriate phenol and 2-(2-methoxyethoxy)ethanol as the appropriate alcohol, Preparation 4b was obtained. $^1$H NMR (500 MHz, DMSO-$d_6$) δ 7.48 (dm, 1H), 7.42-7.37 (m, 1H), 6.94 (dm, 1H), 6.92-6.90 (m, 1H), 4.05-4.01 (m, 2H), 3.76-3.72 (m, 2H), 3.70-3.67 (m, 2H), 3.46-3.43 (m, 2H), 3.24 (s, 3H), 1.26 (s, 12H)

Preparation 4c

2-[2-[2-[2-(2-methoxyethoxy)ethoxy]ethoxy]phenyl]-4,4,5,5-tetramethyl-1,3,2-dioxaborolane Using General Procedure IV, 2-iodophenol as the appropriate phenol and 2-[2-(2-methoxyethoxy)ethoxy]ethanol as the appropriate alcohol, Preparation 4c was obtained. $^1$H NMR (500 MHz, DMSO-$d_6$) δ 7.48 (dm, 1H), 7.49-7.46 (m, 1H), 6.94 (dm, 1H), 6.93-6.89 (m, 1H), 4.04-4.01 (m, 2H), 3.75-3.72 (m, 2H), 3.71-3.39 (m, 8H), 3.22 (s, 3H), 1.26 (s, 12H)

Preparation 4d

2-[2-(2-methoxyethoxymethyl)phenyl]-4,4,5,5-tetramethyl-1,3,2-dioxaborolane

Step A: 1-bromo-2-(2-methoxyethoxymethyl)benzene

To 20 mL of 2-methoxyethanol (672 mmol, 20 eq) 4.03 g sodium hydride (100.8 mmol, 60% in oil, 3 eq.) was added in small portions at 0° C. After 30 minutes stirring, 8.40 g 1-bromo-2-(bromomethyl)benzene (33.6 mmol, 1 eq.) was added, then the reaction mixture was removed from the cooling bath and further was stirred at r.t. until no further conversion was observed. Reaction mixture was diluted with EtOAc and brine. After extraction the organic phase was washed with brine and dried over MgSO4, filtered and concentrated under reduced pressure. Crude product was purified by flash chromatography using heptane and EtOAc as eluents to obtain 1-bromo-2-(2-methoxyethoxymethyl)benzene. $^1$H NMR (400 MHz, DMSO-$d_6$) δ 7.60 (d, 1H), 7.49 (d, 1H), 7.39 (t, 1H), 7.24 (t, 1H), 4.52 (s, 2H), 3.63 (dd, 2H), 3.51 (dd, 2H), 3.27 (s, 3H)

Step B: Preparation 4d

Product from Step A was converted to the appropriate boronic ester using General Procedure IV Step B to obtain Preparation 4d. $^1$H NMR (400 MHz, DMSO-$d_6$) δ 7.80 (d, 1H), 7.50 (d, 1H), 7.43 (t, 1H), 7.28 (t, 1H), 4.85 (s, 2H), 3.66 (dd, 2H), 3.59 (dd, 2H), 3.41 (s, 3H), 1.36 (s, 12H)

Preparation 4e

4,4,5,5-tetramethyl-2-[2-(2-tetrahydropyran-2-yloxyethoxymethyl)phenyl]-1,3,2-dioxaborolane

Step A: 2-[2-[(2-iodophenyl)methoxy]ethoxy]tetrahydropyran

To a solution of 2.34 g (2-iodophenyl)methanol (10 mmol, 1 eq.) in 25 mL dry DMF 440 mg sodium hydride (11 mmol, 60% in oil, 1.1 eq.) was added in small portions at 0° C. After 30 minutes stirring, 2.5 g 2-(2-bromoethoxy)tetrahydropyran (12 mmol, 1.2 eq.) was added, then the reaction mixture was removed from the cooling bath and further was stirred at 50° C. until no further conversion was observed. Reaction mixture was diluted with EtOAc and brine. After extraction the organic phase was washed with brine and dried over MgSO4, filtered and concentrated under reduced pressure. Crude product was purified by flash chromatography using heptane and EtOAc as eluents to obtain 2-[2-[(2-iodophenyl)methoxy]ethoxy]tetrahydropyran. $^1$H NMR (400 MHz, CDCl$_3$) δ 7.83 (d, 1H), 7.50 (d, 1H), 7.36 (t, 1H), 6.99 (t, 1H), 4.70 (t, 1H), 4.59 (s, 2H), 3.98-3.88 (m, 2H), 3.79-3.76 (m, 2H), 3.73-3.68 (m, 1H), 3.56-3.51 (m, 1H), 1.94-1.83 (m, 1H), 1.80-1.73 (m, 1H), 1.70-1.52 (m, 4H)

Step B: Preparation 4e

To a solution of 1.0 g product from Step A (2.76 mmol, 1 eq.) in 15 mL dry THF 4.24 mL $^i$PrMgCl×LiCl (5.52 mmol, 1.3M in THF, 2 eq.) was added at 0° C. over 2 minutes. After 10 minutes stirring, 1.40 mL 2-isopropoxy-4,4,5,5-tetramethyl-1,3,2-dioxaborolane (6.9 mmol, 2.5 eq.) was added then it was stirred at 0° C. until no further conversion was observed. The reaction mixture was diluted with EtOAc and brine. After extraction the organic phase was washed with brine and dried over MgSO4, filtered and concentrated under reduced pressure. The crude product was purified by flash chromatography using heptane and EtOAc as eluents to obtain Preparation 4e. $^1$H NMR (400 MHz, CDCl$_3$) δ 7.80 (d, 1H), 7.53 (d, 1H), 7.44 (t, 1H), 7.28 (t, 1H), 4.87 (s, 1H), 4.68 (t, 2H), 3.94-3.87 (m, 2H), 3.76-3.64 (m, 3H), 3.54-3.49 (m, 1H), 1.93-1.82 (m, 1H), 1.78-1.71 (m, 1H), 1.69-1.52 (m, 4H)

Preparation 4f

2-[2-[(2,2-dimethyl-1,3-dioxolan-4-yl)methoxymethyl]phenyl]-4,4,5,5-tetramethyl-1,3,2-dioxaborolane

Step A: 4-[(2-bromophenyl)methoxymethyl]-2,2-dimethyl-1,3-dioxolane

To a solution of 1.3 mL (2,2-dimethyl-1,3-dioxolan-4-yl)methanol (11 mmol, 1.1 eq) in 25 mL dry DMF 440 mg sodium hydride (11 mmol, 60% in oil, 1.1 eq.) was added in small portions at 0° C. After 30 minutes stirring, 2.5 g 1-bromo-2-(bromomethyl)benzene (10 mmol, 1 eq.) was added, then the reaction mixture was removed from the cooling bath and was stirred at rt until no further conversion was observed. The reaction mixture was diluted with EtOAc and brine. After extraction the organic phase was washed with brine and dried over MgSO4, filtered and concentrated under reduced pressure. The crude product was purified by flash chromatography using heptane and EtOAc as eluents to obtain 4-[(2-bromophenyl)methoxymethyl]-2,2-dimethyl-1,3-dioxolane. $^1$H NMR (400 MHz, CDCl$_3$) δ 7.55 (d, 1H), 7.49 (d, 1H), 7.33 (t, 1H), 7.17 (t, 1H), 4.65 (dd, 2H), 4.36 (qui, 1H), 4.11 (dd, 1H), 3.82 (dd, 1H), 3.67 (dd, 1H), 3.59 (dd, 1H), 1.46 (s, 3H), 1.39 (s, 3H)

Step B: Preparation 4f

Product from Step A was converted to the appropriate boronic ester using General Procedure IV Step B to obtain Preparation 4f. $^1$H NMR (400 MHz, DMSO-$d_6$) δ 7.65 (d, 1H), 7.45 (t, 1H), 7.41 (d, 1H), 7.29 (t, 1H), 4.68 (dd, 2H), 4.20 (qui, 1H), 3.98 (dd, 1H), 3.62 (dd, 1H), 3.51-3.42 (m, 2H), 1.30 (s, 3H), 1.30 (s, 12H), 1.26 (s, 3H)

Preparation 4 g 4,4,5,5-tetramethyl-2-[3-(2-tetrahydropyran-2-yloxy-ethoxymethyl)phenyl]-1,3,2-dioxaborolane Step A: 2-[2-[(3-iodophenyl)methoxy]ethoxy]tetra-hydropyran To a solution of 2.34 g (3-iodophenyl)methanol (10 mmol, 1 eq.) in 25 mL dry DMF 440 mg sodium hydride (11 mmol, 60% in oil, 1.1 eq.) was added in small portions at 0° C. After 30 minutes stirring, 2.5 g 2-(2-bromoethoxy)tetra-hydropyran (12 mmol, 1.2 eq.) was added, then the reaction mixture was removed from the cooling bath and was stirred at 50° C. until no further conversion was observed. Reaction mixture was diluted with EtOAc and brine. After extraction the organic phase was washed with brine and dried over $MgSO_4$, filtered and concentrated under reduced pressure. The crude product was purified by flash chromatography using heptane and EtOAc as eluents to obtain 2-[2-[(3-iodophenyl)methoxy]ethoxy]tetrahydropyran. MS (EI, 70 eV) m/z (% relative intensity, [ion]): 85 (100), 217 (57), 233 (15), 278 (15), 362 (1)

Step B: Preparation 4 g

To a solution of 1.0 g product from Step A (2.76 mmol, 1 eq.) in 15 mL dry THF 4.24 mL $^i$PrMgCl×LiCl (5.52 mmol, 1.3M in THF, 2 eq.) was added at 0° C. over 2 minutes. After 10 minutes stirring, 1.40 mL 2-isopropoxy-4,4,5,5-tetramethyl-1,3,2-dioxaborolane (6.9 mmol, 2.5 eq.) was added then it was stirred at 0° C. until no further conversion was observed. The reaction mixture was diluted with EtOAc and brine. After extraction the organic phase was washed with brine and dried over $MgSO_4$, filtered and concentrated under reduced pressure. The crude product was purified by flash chromatography using heptane and EtOAc as eluents to obtain Preparation 4 g. $^1$H NMR (400 MHz, $CDCl_3$) δ 7.79 (s, 1H), 7.75 (d, 1H), 7.51 (d, 1H), 7.38 (t, 1H), 4.67 (t, 1H), 4.63 (d, 1H), 4.59 (d, 1H), 3.95-3.83 (m, 2H), 3.71-3.62 (m, 3H), 3.55-3.48 (m, 1H), 1.94-1.47 (m, 6H), 1.37 (s, 12H)

Preparation 4h

2-[3-[2-methoxy-1-(methoxymethyl)ethoxy]phenyl]-4,4,5,5-tetramethyl-1,3,2-dioxaborolane To the solution of 880 mg (4 mmol, 1 eq.) 3-(4,4,5,5-tetramethyl-1,3,2-dioxaborolan-2-yl) phenol and 1371 mg (5.0 mmol, 1.25 eq.) [2-methoxy-1-(methoxymethyl)ethyl] 4-methylbenzenesulfonate in 16 mL DMF, 1954 mg (6.0 mmol, 1.5 eq.) cesium carbonate was added and it was stirred at 75° C. for 16 hours, then at 85° C. for 8 hours. The reaction mixture was cooled to r.t. and it was concentrated under reduced pressure. To the residue 25 mL brine was added and it was extracted with 3×25 mL ethyl acetate. The combined organic layer was dried over $MgSO_4$ and concentrated under reduced pressure. The residue was purified by flash chromatography on silica gel using heptane and ethyl acetate as eluents to give Preparation 4h. HRMS calculated for $C_{17}H_{27}BO_5$: 322.1952; found 323.2025 (M+H)

Preparation 4i

2-[4-[2-methoxy-1-(methoxymethyl)ethoxy]phenyl]-4,4,5,5-tetra methyl-1,3,2-dioxaborolane To the solution of 880 mg (4 mmol, 1.0 eq.) 4-(4,4,5,5-tetramethyl-1,3,2-dioxaborolan-2-yl)phenol and 1371 mg (5.0 mmol, 1.25 eq.) [2-methoxy-1-(methoxymethyl)ethyl] 4-methylbenzenesulfonate in 16 mL DMF, 1954 mg (6.0 mmol, 1.5 eq.) cesium carbonate was added and it was stirred at 75° C. for 16 hours. The reaction mixture was cooled to r.t. and it was concentrated under reduced pressure. To the residue 25 mL brine was added and it was extracted with 3×25 mL ethyl acetate. The combined organic layer was dried over $MgSO_4$ and concentrated under reduced pressure. The residue was purified by flash chromatography on silica gel using heptane and ethyl acetate as eluents to give Preparation 4i. HRMS calculated for $C_{17}H_{27}BO_5$: 322.1952; found 323.2036 (M+H).

Preparation 4j

[(2R)-4,5-diacetoxy-6-methoxy-2-[[3-(4,4,5,5-tetramethyl-1,3,2-dioxaborolan-2-yl)phenoxy]methyl] tetrahydropyran-3-yl]acetate Step A: Methyl 2,3,4-tri-O-acetyl-α-D-mannopyranoside 2.25 g (4 mmol) methyl 2,3,4-tri-O-acetyl-6-triphenylmethyl-α-D-mannopyranoside was dissolved in 30 mL acetic acid at 85° C., then 15 mL water was added and it was stirred at 90° C. for 1 hour. It was cooled to r.t. then it was poured into ice cold brine. The mixture was filtered and the filtrate was extracted with dichloromethane. The combined organic layer was dried over $MgSO_4$, it was filtered and concentrated under reduced pressure. The residue was purified by flash chromatography on silica gel using heptane and ethyl acetate as eluents to give methyl 2,3,4-tri-O-acetyl-α-D-mannopyranoside. $^1$H NMR (500 MHz, DMSO-$d_6$): 5.11-5.03 (m, 3H), 4.85 (t, 1H), 4.73 (d, 1H), 3.65 (m, 1H), 3.48 (m, 1H), 3.42 (m, 1H), 3.33 (s, 3H), 2.11-1.91 (s, 9H)

Step B: Preparation 4j

Starting from methyl 2,3,4-tri-O-acetyl-α-D-mannopyranoside and 3-(4,4,5,5-tetramethyl-1,3,2-dioxaborolan-2-yl) phenol using General Procedure IV Step A, Preparation 4j was obtained. $^1$H NMR (500 MHz, DMSO-$d_6$): 7.31 (t, 1H), 7.26 (m, 1H), 7.15 (m, 1H), 7.06 (m, 1H), 5.25 (t, 1H), 5.12 (m, 1H), 5.11 (m, 1H), 4.79 (d, 1H), 4.13 (dd, 1H), 4.05 (dd, 1H), 3.99 (m, 1H), 3.36 (s, 3H), 2.15-1.92 (s, 9H), 1.29 (s, 12H)

Preparation 4k 4,4,5,5-tetramethyl-2-[3-[[(2S)-3,4,5,6-tetramethoxytetrahydropyran-2-yl]methoxy]phenyl]-1,3,2-dioxaborolane Step A: methyl-6-triphenylmethyl 2,3,4-tri-O-methyl-α-D-mannopyranoside To the solution of 8.08 g (18.51 mmol) methyl 6-triphenylmethyl-α-D-mannopyranoside in 150 mL DMF 2.89 g sodium hydride (60% in mineral oil, 72.2 mmol, 3.9 eq.) was added portionwise at 0° C. and it was stirred at this temperature for 30 minutes. Then 5.20 mL MeI (11.8 g, 83.3 mmol, 4.5 eq.) was added dropwise at 0° C. and it was stirred at r.t. for 16 hours. To the reaction mixture 10 mL MeOH was added and it was stirred for 15 minutes, then it was concentrated under reduce pressure. The residue was diluted with 200 mL water and extracted with DCM. The combined organic layer was dried over MgSO$_4$, it was filtered and concentrated under reduced pressure. The residue was purified by flash chromatography on silica gel using heptane and ethyl acetate as eluents to give methyl-6-triphenylmethyl 2,3,4-tri-O-methyl-α-D-mannopyranoside. $^1$H NMR (500 MHz, DMSO-d$_6$): 7.44-7.23 (m, 15H), 4.85 (d, 1H), 3.58 (dd, 1H), 3.48 (m, 1H), 3.39 (s, 3H), 3.36 (s, 3H), 3.33 (dd, 1H), 3.31 (s, 3H), 3.28 (t, 1H), 3.23 (dd, 1H), 3.11 (s, 3H), 3.1 (dd, 1H)

Step B: methyl 2,3,4-tri-O-methyl-α-D-mannopyranoside 1.914 g methyl-6-triphenylmethyl 2,3,4-tri-O-methyl-α-D-mannopyranoside (4.0 mmol) was dissolved in 30 mL acetic acid at 85° C., then 15 mL water was added and it was stirred at 90° C. for 1 hour. It was cooled to r.t. and it was poured into ice cold brine. The mixture was filtered and the filtrate was extracted with dichloromethane. The combined organic layer was dried over MgSO$_4$, it was filtered and concentrated under reduced pressure. The residue was purified by flash chromatography on silica gel using heptane and ethyl acetate as eluents to give methyl 2,3,4-tri-O-methyl-α-D-mannopyranoside. $^1$H NMR (500 MHz, DMSO-d$_6$): 4.72 (d, 1H), 4.63 (br s, 1H), 3.56 (dd, 1H), 3.54 (dd, 1H), 3.47 (dd, 1H), 3.36 (s, 3H), 3.34 (s, 3H), 3.32 (m, 1H), 3.32 (s, 3H), 3.26 (s, 3H), 3.24 (m, 1H), 3.22 (m, 1H)

Step C: Preparation 4k

Starting from methyl 2,3,4-tri-O-methyl-α-D-mannopyranoside and 3-(4,4,5,5-tetramethyl-1,3,2-dioxaborolan-2-yl)phenol using General Procedure IV Step A, Preparation 4k was obtained. $^1$H NMR (500 MHz, DMSO-d$_6$): 7.31 (dd, 1H), 7.25 (dm, 1H), 7.19 (m, 1H), 7.09 (dm, 1H), 4.77 (d, 1H), 4.14 (dd, 1H), 4.09 (dd, 1H), 3.60 (m, 1H), 3.59 (dd, 1H), 3.41 (t, 1H), 3.38 (dd, 1H), 3.37 (s, 3H), 3.36 (s, 3H), 3.34 (s, 3H), 3.33 (s, 3H), 1.29 (s, 12H)

Preparation 4l

[(2R)-4,5-diacetoxy-6-methoxy-2-[[4-(4,4,5,5-tetramethyl-1,3,2-dioxaborolan-2-yl)phenoxy]methyl] tetrahydropyran-3-yl]acetate Starting from methyl 2,3,4-tri-O-acetyl-α-D-mannopyranoside (from Preparation 4j Step A) and 4-(4,4,5,5-tetramethyl-1,3,2-dioxaborolan-2-yl)phenol using General Procedure IV Step A, Preparation 4l was obtained. $^1$H NMR (500 MHz, DMSO-d$_6$): 7.60 (m, 2H), 6.92 (m, 2H), 5.23 (t, 1H), 5.13 (dd, 1H), 5.11 (dd, 1H), 4.80 (d, 1H), 4.14 (dd, 1H), 4.06 (dd, 1H), 4.02 (m, 1H), 3.36 (s, 3H), 2.14-1.92 (s, 9H), 1.27 (s, 12H)

Preparation 4m 4,4,5,5-tetramethyl-2-[4-[[(2S)-3,4,5,6-tetramethoxytetrahydropyran-2-yl]methoxy]phenyl]-1,3,2-dioxaborolane Starting from methyl 2,3,4-tri-O-methyl-α-D-mannopyranoside (from Preparation 4j Step A) and 4-(4,4,5,5-tetramethyl-1,3,2-dioxaborolan-2-yl)phenol using General Procedure IV Step A, Preparation 4m was obtained. $^1$H NMR (500 MHz, DMSO-d$_6$): 7.61 (m, 2H), 6.96 (m, 2H), 4.77 (d, 1H), 4.16 (dd, 1H), 4.10 (dd, 1H), 3.61 (m, 1H), 3.60 (d, 1H), 3.38 (m, 2H), 3.37-3.28 (s, 12H), 1.27 (s, 12H)

Preparation 4n

[(2R)-4,5,6-triacetoxy-2-[[4-(4,4,5,5-tetramethyl-1,3,2-dioxaborolan-2-yl)phenoxy]methyl]tetrahydropyran-3-yl]acetate Step A: 1,2,3,4-tetra-O-acetyl-α/β-D-mannopyranose 2.36 g 1,2,3,4-tetra-O-acetyl-6-triphenylmethyl-α/β-D-mannopyranose (4.0 mmol) was dissolved in 30 mL acetic acid at 65° C., then 15 mL water was added and it was stirred at 65° C. for 1 hour. It was cooled to r.t. and it was poured into ice cold brine. The mixture was filtered and the filtrate was extracted with dichloromethane. The combined organic layer was dried over MgSO$_4$, it was filtered and concentrated under reduced pressure. The residue was purified by flash chromatography on silica gel using heptane and ethyl acetate as eluents to give 1,2,3,4-tetra-O-acetyl-α/β-D-mannopyranose. $^1$H NMR (500 MHz, DMSO-d$_6$): 6.06-5.97 (d, 1H), 5.20-5.06 (t, 1H), 5.31-5.18 (dd, 1H), 5.35-5.14 (dd, 1H), 4.89-4.87 (t, 1H), 3.84-3.74 (m, 1H), 3.52-3.34 (m, 2H), 2.20-1.90 (s, 12H)

Step B: Preparation 4n

Starting from 1,2,3,4-tetra-O-acetyl-α/β-D-mannopyranose and 4-(4,4,5,5-tetramethyl-1,3,2-dioxaborolan-2-yl)phenol using General Procedure IV Step A, Preparation 4n was obtained as the mixture of stereoisomers. $^1$H NMR (500 MHz, DMSO-d$_6$): 7.60 (m, 2H), 6.91 (m, 2H), 6.15-6.00 (d, 1H), 5.43-5.15 (m, 3H), 4.23-4.20 (m, 1H), 4.14-4.00 (m, 2H), 2.19-1.92 (s, 12H), 1.27 (s, 12H)

Preparation 4o

[(3R,4S,6S)-3,4,5-triacetoxy-6-[[4-(4,4,5,5-tetramethyl-1,3,2-dioxaborolan-2-yl)phenyl]methoxy]tetrahydropyran-2-yl]methyl acetate and Preparation 4p

[(2R,3aS,6R,7S)-6,7-diacetoxy-2-methyl-2-[[4-(4,4,5,5-tetramethyl-1,3,2-dioxaborolan-2-yl)phenyl]methoxy]-5,6,7,7a-tetrahydro-3aH[1,3]dioxolo[4,5-b]pyran-5-yl]methyl acetate Step A: 1-bromo-2,3,4,6-tetra-O-acetyl-α/β-D-mannopyranose 1 mL acetic anhydride was added to 30 mL HBr in acetic acid (33%) and it was stirred at r.t. for 16 hours. It was cooled to 0° C., and the solution of 7.50 g 1,2,3,4,6-penta-O-acetyl-α/β-D-mannopyranose (19.2 mmol) in 30 mL dichloromethane was added dropwise at 0° C. The reaction mixture was stirred at this temperature for 2 hours then at r.t. for 16 hours. The mixture was cooled to 0° C. and it was poured onto 100 mL ice-water. It was diluted with 120 mL DCM then the phases were separated. Organic layer was washed with ice cold water, saturated NaHCO$_3$ and water again. The organic layer was dried over MgSO$_4$, it was filtered and concentrated under reduced pressure to give 1-bromo-2,3,4,6-tetra-O-acetyl-α/β-D-mannopyranose. $^1$H NMR (500 MHz, DMSO-d$_6$): 6.77 (d, 1H), 5.50 (dd, 1H), 5.35 (dd, 1H), 5.23 (t, 1H), 4.17 (m, 1H), 4.25 (dd, 1H), 4.08 (dd, 1H), 2.13 (s, 3H), 2.06 (s, 3H), 2.03 (s, 3H), 1.96 (s, 3H)

Step B: Preparations 4o and 4p

To the solution of 819 mg [4-(4,4,5,5-tetramethyl-1,3,2-dioxaborolan-2-yl)phenyl]methanol (3.50 mmol, 1 eq.), 2015 mg 1-bromo-2,3,4,6-tetra-O-acetyl-α/β-D-mannopyranose (4.90 mmol, 1.4 eq.), 467 mg s-collidine (3.85 mmol, 1.1 eq.) in 100 mL DCM 1708 mg silver trifluoromethanesulfonate (6.65 mmol, 1.9 eq.) in 15 mL toluene was added dropwise at −78° C. and the mixture was stirred at this temperature for 10 minutes. The mixture was let to warm slowly to r.t. (3 hours), then it was stirred for 10 hours. The mixture was filtered through a Celite pad, the filtrate was concentrated. The residue was purified by flash chromatography on silica gel using heptane and ethyl acetate as eluents to give Preparation 4o as first eluted product $^1$H NMR (500 MHz, DMSO-d$_6$): 7.69 (m, 2H), 7.39 (m, 2H), 5.15-5.10 (m, 3H), 4.96 (d, 1H), 4.71 (d, 1H), 4.57 (d, 1H), 4.15 (dd, 1H), 4.04 (dd, 1H), 3.96 (m, 1H), 2.12-1.91 (s, 12H), 1.29 (s, 12H); and Preparation 4p as later eluted product. $^1$H NMR (500 MHz, DMSO-d$_6$): 7.63 (m, 2H), 7.31 (m, 2H), 5.68 (d, 1H), 5.32 (dd, 1H), 5.05 (t, 1H), 4.59 (d, 1h) 4.54 (dd, 1H), 4.53 (d, 1H), 4.12 (dd, 1H), 4.03 (dd, 1H), 3.94 (m, 1H), 2.01-1.97 (s, 9H), 1.70 (s, 3H), 1.29 (s, 12H)

Preparation 4q

[5-(4,4,5,5-tetramethyl-1,3,2-dioxaborolan-2-yl)pyrimidin-2-yl]methanol 113 mg (5-bromopyrimidin-2-yl)methanol (0.6 mmol) and 609 mg 4,4,5,5-tetramethyl-2-(4,4,5,5-tetramethyl-1,3,2-dioxaborolan-2-yl)-1,3,2-dioxaborolane (2.4 mmol) were dissolved in 6 mL dioxane, then 353 mg KOAc (3.6 mmol) and 66 mg PdCl$_2$×dppf (0.09 mmol) were added. The mixture was stirred under nitrogen at 60° C. for 2 hours. The resulting mixture was used without further manipulation. MS (M+H): 237.1

Preparation 5

Ethyl (2R)-2-[5-[3-chloro-2-methyl-4-[2-(4-methylpiperazin-1-yl) ethoxy]phenyl]-6-(4-fluorophenyl)thieno[2,3-d]pyrimidin-4-yl]oxy-3-[2-[[2-[3-(hydroxymethyl)phenyl]pyrimidin-4-yl]methoxy]phenyl]propanoate Using General Procedure I Step A and [3-(4,4,5,5-tetramethyl-1,3,2-dioxaborolan-2-yl)phenyl]methanol as the appropriate boronic ester, Preparation 5 was obtained as a mixture diastereoisomers. MS: [M+H]$^+$=903.2

Example 1

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3-hydroxyphenyl)pyrimidin-4-yl]methoxy}phenyl)propanoic acid Starting from Preparation 2 using General procedure I Step B, Example 1 was obtained. HRMS calculated for C$_{46}$H$_{42}$ClFN$_6$O$_6$S: 860.2559; found 431.1349 (M+2)$^{2+}$.

Example 2

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(4-hydroxyphenyl)pyrimidin-4-yl]methoxy}phenyl)propanoic acid Starting from Preparation 3 using General procedure I Step B, Example 2 was obtained. HRMS calculated for C$_{46}$H$_{42}$ClFN$_6$O$_6$S: 860.2559; found 431.1371 (M+2H)$^{2+}$.

Example 3

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[3-(hydroxymethyl)phenyl]pyrimidin-4-yl}methoxy)phenyl]propanoic acid Starting from Preparation 1 and [3-(4,4,5,5-tetramethyl-1,3,2-dioxaborolan-2-yl)phenyl]methanol using General procedure I, Example 3 was obtained. HRMS calculated for C$_{47}$H$_{44}$ClFN$_6$O$_6$S: 874.2715; found 438.141 (M+2H)$^{2+}$.

Example 4

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[4-(hydroxymethyl)phenyl]pyrimidin-4-yl}methoxy)phenyl]propanoic acid Starting from Preparation 1 and [4-(4,4,5,5-tetramethyl-1,3,2-dioxaborolan-2-yl)phenyl]methanol using General procedure I, Example 4 was obtained. HRMS calculated for C$_{47}$H$_{44}$ClFN$_6$O$_6$S: 874.2715; found 438.1449 (M+2H)$^{2+}$.

Example 5

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{2-[(2,2-dimethyl-1,3-dioxolan-4-yl)methoxyl]phenyl}pyrimidin-4-yl)methoxy]phenyl}propanoic acid Starting from Preparation 1 and Preparation 4a using General procedure 1, Example 5 was obtained. HRMS calculated for C$_{52}$H$_{52}$ClFN$_6$O$_8$S: 974.324; found 488.1698 (M+2H)$^{2+}$.

Example 6

(2R)-2-{[(5S$_a$)-5-{3-chloro-2-methyl-4-[2-(4-methylpiperazin-1-yl)ethoxy]phenyl}-6-(4-fluoropnhenyl)thieno[2,3-d]pyrimidin-4-yl]oxy}-3-{2-[(2-{2-[2-(2-methoxyethoxy)ethoxy]phenyl}pyrimidin-4-yl)methoxy]phenyl}propanoic acid Starting from Preparation 1 and Preparation 4b using General procedure I, Example 6 was obtained. HRMS calculated for C$_{51}$H$_{52}$ClFN$_6$O$_8$S: 962.324; found 482.1695 (M+2H)$^{2+}$.

Example 7

(2R)-2-{[(5S$_a$)-5-{3-chloro-2-methyl-4-[2-(4-methylpiperazin-1-yl)ethoxy]phenyl}-6-(4-flurophenyl) thieno[2,3-d]pyrimidin-4-yl]oxy}-3-(2-{[2-(2-{2-[2-(2-methoxyethoxy)ethoxy]ethoxy}phenyl)pyrimidin-4-yl]methoxy}phenyl)propanoic acid Starting from Preparation 1 and Preparation 4c using General procedure I, Example 7 was obtained. HRMS calculated for $C_{53}H_{56}ClFN_6O_9S$: 1006.3502; found 504.1828 (M+2H)$^{2+}$.

Example 8

(2R)-2-{[(5S$_a$)-5-{3-chloro-2-methyl-4-[2-(4-methylpiperazin-1-yl)ethoxy]phenyl}-6-(4-flurophenyl) thieno[2,3-d]pyrimidin-4-yl]oxy}-3-[2-({2-[2-(methoxymethyl)phenyl]pyrimidin-4-yl}methoxy) phenyl]propanoic acid Starting from Preparation 1 and [2-(methoxymethyl)phenyl]-4,4,5,5-tetramethyl-1,3,2-dioxaborolane using General procedure I, Example 8 was obtained. HRMS calculated for $C_{48}H_{46}ClFN_6O_7S$; 888.2872; found 445.1518 (M+2H)$^{2+}$.

Example 9

(2R)-2-{[(5S$_a$)-5-{3-chloro-2-methyl-4-[2-(4-methylpiperazin-1-yl)ethoxy]phenyl}-6-(4-fluorophenyl) thieno[2,3-d]pyrimidin-4-yl]oxy}-3-{2-[(2-{2-[(2-methoxyethoxy)methyl]phenyl}pyrimidin-4-yl) methoxy]phenyl}propanoic acid Starting from Preparation 1 and Preparation 4d using General procedure 1, Example 9 was obtained. HRMS calculated for $C_{50}H_{50}ClFN_6O_7S$: 932.3134; found 467.164 (M+2H)$^{2+}$.

Example 10

(2R)-2-{[(5S$_a$)-5-{3-chloro-2-methyl-4-[2-(4-methylpiperazin-1-yl)ethoxy]phenyl}-6-(4-fluorophenyl) thieno[2,3-d]pyrimidin-4-yl]oxy}-3-{2-[(2-{2-[(2-hydroxyethoxy)methyl]phenyl}pyrimidin-4-yl) methoxy]phenyl}propanoic acid Starting from Preparation 1 and Preparation 4e using General procedure I, after completion of the reaction in Step B the pH was set to 1 with 2M aqueous HCl solution and it was stirred until no further conversion was observed. Then it was neutralized with 10% aqueous $K_2CO_3$ solution, diluted with brine, extracted with DCM. The combined organic phases were dried over $MgSO_4$, filtered and the filtrate was concentrated under reduced pressure. The crude product was purified via preparative reversed phase chromatography using 5 mM aqueous $NH_4HCO_3$ solution and MeCN as eluents. The diastereoisomer eluting later was collected to obtain Example 10. HRMS calculated for $C_{49}H_{48}N_6O_7FSCl$; 918.2978; found 460.1572 (M+2H)$^{2+}$.

Example 11

(2R)-2-{[(5S$_a$)-5-{3-chloro-2-methyl-4-[2-(4-methylpiperazin-1-yl)ethoxy]phenyl}-6-(4-fluorophenyl) thieno[2,3-d]pyrimidin-4-yl]oxy}-3-(2-{[2-(2-{[(2,2-dimethyl-1,3-dioxolan-4-yl)methoxy] methyl}phenyl)pyrimidin-4-yl]methoxy}phenyl) propanoic acid Starting from Preparation 1. and Preparation 4f using General procedure I Example 11 was obtained. HRMS calculated for $C_{53}H_{54}ClFN_6O_8S$: 988.3397; found 495.1762 (M+2H)$^{2+}$.

Example 12

(2R)-2-{[(5S$_a$)-5-{3-chloro-2-methyl-4-[2-(4-methylpiperazin-1-yl(ethoxy]phenyl}-6-(4-fluorophenyl) thieno[2,3-d]pyrimidin-4-yl]oxy}-3-{2-[(2-{3-[(2-hydroxyethoxy)methyl]phenyl}pyrimidin-4-yl) methoxy]phenyl}propanoic acid Starting from Preparation 1 and Preparation 4g using using General procedure I, after completion of the reaction in Step B the pH was set to 1 with 2M aqueous HCl solution and it was stirred until no further conversion was observed. Then it was neutralized with 10% aqueous $K_2CO_3$ solution, diluted with brine, extracted with DCM. The combined organic phases were dried over $MgSO_4$, filtered and the filtrate was concentrated under reduced pressure. The crude product was purified via preparative reversed phase chromatography using 5 mM aqueous $NH_4HCO_3$ solution and MeCN as eluents. The diastereoisomer eluting later was collected to obtain Example 12. HRMS calculated for $C_{49}H_{48}ClFN_6O_7S$: 918.2978; found 460.1556 (M+2H)$^{2+}$.

Example 13

(2R)-2-{[(5S$_a$)-5-{3-chloro-2-methyl-4-[2-(4-methylpiperazin-1-yl)ethoxy]phenyl}-6-(4fluorophenyl) thieno[2,3-d]pyrimidin-4-yl]oxy}-3-{2-[(2-{3-[(1,3-dimethoxypropan-2-yl)oxy]phenyl}pyrimidin-4-yl) methoxy]phenyl}propanoic acid Starting from Preparation 1 and Preparation 4h using General procedure I, Example 13 was obtained. HRMS calculated for $C_{51}H_{52}ClFN_6O_8S$: 962.324; found 482.1694 (M+2H)$^{2+}$.

Example 14

(2R)-2-{[(5S$_a$)-5-{3-chloro-2-methyl-4-[2-(4-methylpiperazin-1-yl)ethoxy]phenyl}-6-(4-fluorophenyl) thieno[2,3-d]pyrimidin-4-yl]oxy}-3-{(2-[(2-{4-[(1,3-dimethoxypropan-2-yl)oxy]phenyl}pyrimidin-4-yl) methoxy]phenyl}propanoic acid Starting from Preparation 1 and Preparation 4i using General procedure I, Example 14 was obtained. HRMS calculated for $C_{51}H_{52}ClFN_6O_8S$; 962.324; found 482.1678 (M+2 H)$^{2+}$.

Example 15

(2R)-2-{[(5S$_a$)-5-{3-chloro-2-methyl-4-[2-(4-methylpiperazin-1-yl)ethoxy]phenyl}-6-(4-fluorophehenyl)thieno[2,3-d]pyrimidin-4-yl]oxy}-3-[2-({2-[4-(2,3-dihydroxypropoxy)phenyl]pyrimidin-4-yl}methoxy)phenyl]propanoic acid Starting from Preparation 3 and (2,2-dimethyl-1,3-dioxolan-4-yl)methanol using General procedure II after completion of the reaction in Step B the pH was set to 1 with 2M aqueous HCl solution and it was stirred until no further conversion was observed. Then it was neutralized with 10% aqueous $K_2CO_3$ solution, diluted with brine, extracted with DCM. The combined organic phases were dried over $MgSO_4$, filtered and the filtrate was concentrated under reduced pressure. The crude product was purified via preparative reversed phase chromatography using 5 aqueous $NH_4HCO_3$ solution and MeCN as eluents. The diastereoisomer eluting later was collected to obtain Example 15. HRMS calculated for $C_{49}H_{48}N_6O_8FSCl$: 934.2927; found 468.1531 $(M+2H)^{2+}$.

Example 16 methyl 6-O-{3-[4-({2-[(2R)-2-carboxy-2-{[(5S$_a$)-5-{3-chloro-2-methyl-4-[2-(4-methylpiperazin-1-yl)ethoxy]phenyl}-6-(4-flurophenyl)thieno[2,3-d]pyrimidin-4-yl]oxy}ethyl]phenoxy}methyl)pyrimidin-2-yl]phenyl}-α-D-mannopyranoside Starting from Preparation 1 and Preparation 4j using General procedure V, Example 16 was obtained. HRMS calculated for $C_{53}H_{54}ClFN_6O_{11}S$; 1036.3243; found 5191696 $(M+2H)^{2+}$.

Example 17 methyl 6-O-{3-[4-({2-[(2R)-2-carboxy-2-{[(5S$_a$)-5-{3-chloro-2-methyl-4-[2-(4methylpiperazin-1-yl)ethoxy]phenyl}-6-(4-fluorophenyl)thieno[2,3-d]pyrimidin-4-yl]oxy}ethyl]phenoxy}methyl)pyrimidin-2-yl]phenyl}-2,3,4-tri-O-methyl-α-D-mannopyranoside Starting from Preparation .1 and Preparation 4k using General procedure I, Example 17 was obtained. HRMS calculated for $C_{56}H_{60}ClFN_6O_{11}S$: 1078.3713; found 540.1936 $(M+2H)^{2+}$.

Example 18 methyl 6-O-{4-[4-({2-[(2R)-2-carboxy-2-{[(5S$_a$)-5-{3-chloro-2-methyl-4-[2-(4-methylpiperazin-1-yl)ethoxy]phenyl}-6-(4-flurophenyl)thieno[2,3-d]pyrimidin-4-yl]oxy}ethyl]phenoxy}methyl)pyrimidin-2-yl]phenyl}-α-D-mannopyranoside Starting from Preparation 1 and Preparation 4l using General procedure V, Example 18 was obtained. HRMS calculated for $C_{53}H_{54}ClFN_6O_{11}S$: 1036.3243; found 519.1714 $(M+2H)^{2+}$.

Example 19 methyl 6-O-{4-[4-({2-[(2R)-2-carboxy-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}ethyl]phenoxy}methyl)pyrimidin-2-yl]phenyl}-2,3,4-tri-O-methyl-α-D-mannopyranoside Starting from Preparation 1 and Preparation 4m using General procedure I, Example 19 was obtained. HRMS calculated for $C_{56}H_{60}ClFN_6O_{11}S$: 1078.3713; found 540.1925 $(M+2H)^{2+}$.

Example 20

6-O-{4-[4-({2-[(2R)-2-carboxy-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}ethyl]phenoxy}methyl)pyrimidin-2-yl]phenyl}-D-mannopyranose and Example 21

6-O-{2-[4-({2-[(2R)-2-carboxy-2-{[(5S$_a$)-5-{3-chloro-2-methyl-4-[2-(4-methylpiperazin-1-ethoxy]phenyl}-6-(4-fluorophenyl)thieno[2,3-d]pyrimidin-4-yl]oxy}ethyl]phenoxy}methyl)pyrimidin-2-yl]phenyl}-D-mannoanic acid Starting from Preparation 1 and Preparation 4n using General procedure V, Example 20 was obtained as the earlier eluting compound. HRMS calculated for $C_{52}H_{52}ClFN_6O_{11}S$: 1022.3087; found 512.1611 $(M+2H)^{2+}$. Example 21 was obtained as the later eluting compound. HRMS calculated for $C_{52}H_{52}ClFN_6O_{12}S$: 1038.3036; found 520.1604 $(M+2H)^{2+}$.

Example 22

1,2-O-[(1R)-1-({4-[4-({2-[(2R)-2-carboxy-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}ethyl]phenoxy}methyl)pyrimidin-2-yl]benzyl}oxy)ethylidene]-β-D-mannopyranose Starting from Preparation 1 and Preparation 4o using General procedure V. Example 22 was obtained. HRMS calculated for $C_{55}H_{56}ClFN_6O_{12}S$: 1078.335; found 1079.343 $(M+H)^+$.

Example 23

(2R)-2-{[(5S$_a$)-5-{3-chloro-2-methyl-4-[2-(4-methylpiperazin-1-yl)ethoxy]phenyl}-6-(4-flurophenyl)thieno[2,3-d]pyrimidin-4-yl]oxy}-3-{2-[(2-{4-[(α-D-mannopyranosyloxy)methyl]phenyl}pyrimidin-4-yl)methoxy]phenyl}propanoic acid Starting from Preparation 1 and Preparation 4p using General procedure V, Example 23 was obtained. HRMS calculated for $C_{53}H_{54}ClFN_6O_{11}S$: 1036.3243; found 519.1682 $(M+2H)^{2+}$.

Example 24

(2R)-2-{[(5S$_a$)-5-{3-chloro-methyl-4-[2-(4methyl-piperazin-1-yl)ethoxy]phenyl}-6-(4-fluorophenyl)thieno[2,3-d]pyrimidin-4-yl]oxy}-3-[2-({2-[4-(2-hydroxyethyl)phenyl]pyrimidin-4-yl}methoxy)phenyl]propanoic acid Starting from Preparation 1 and [4-(2-hydroxyethyl)phenyl]boronic acid using General procedure I, Example 24 was obtained. HRMS calculated for $C_{48}H_{46}N_6O_6FSCl$: 888.2872; found 445.1512 $(M+2H)^{2+}$.

Example 25

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[2-(2,3-dihydroxypropoxy)phenyl]pyrimidin-4-}methoxy)phenyl]propanoic acid Starting from Preparation 1 and Preparation 4a using General procedure I after completion of the reaction in Step B the pH was set to 1 with 2M aqueous HCl solution and it was stirred until no further conversion was observed. Then it was neutralized with 10% aqueous $K_2CO_3$ solution, diluted with brine, extracted with DCM. The combined organic phases were dried over $MgSO_4$, filtered and the filtrate was concentrated under reduced pressure. The crude product was purified via preparative reversed phase chromatography using 5 mM aqueous $NH_4HCO_3$ solution and MeCN as eluents. The diastereoisomer eluting later was collected to obtain Example 25. HRMS calculated for $C_{49}H_{48}ClFN_6O_8S$: 934.2927; found 468.1536 $(M+2H)^{2+}$.

Example 26

(2R)-2-{[(5S$_a$)-5-{3-chloro-2-methyl-4-[2-(4methylpiperazin-1-yl)ethoxy]phenyl}-6-(4-fluorophenyl)thieno[2,3-d]pyrimidin-4-yl]oxy}-3-[2-({2-[2-(2-hydroxyethoxy)phenyl]pyrimidin-4-yl}methoxy)phenyl]propanoic acid Step A: Ethyl (2R)-2-hydroxy-3-[2-[[2-[2-(2-methoxyethoxy)phenyl]pyrimidin-4-yl]methoxy]phenyl]propanoate A solution of 1.01 g ethyl (2R)-3-[2-[(2-chloropyrimidin-4-yl)methoxy]phenyl]-2-hydroxy-propanoate (from Preparation 1 Step E) (3 mmol, 1 eq.), 1.17 g [2-(2-methoxyethoxy)phenyl]boronic acid (6 mmol, 2 eq.), 2.93 g cesium carbonate (9 mmol, 3 eq.) and 210 mg Pd(PPh$_3$)$_2$Cl$_2$ in 30 mL dioxane/H$_2$O (1:1) were stirred at 70° C. until no further conversion was observed. The reaction mixture was diluted with EtOAc and brine. After extraction the organic phase was washed with brine and dried over MgSO$_4$, filtered and concentrated under reduced pressure. The crude product was purified by flash chromatography using heptane and EtOAc as eluents to obtain ethyl (2R)-2-hydroxy-3-[2-[[2-[2-(2-methoxyethoxy)phenyl]pyrimidin-4-yl]methoxy]phenyl]propanoate as colorless oil. $^1$H NMR (400 MHz, DMSO-d$_6$) δ 8.92 (d, 1H), 7.60 (dd, 1H), 7.59 (d, 1H), 7.45 (dd, 1H), 7.24-7.15 (m, 3H), 7.08 (t, 1H), 7.02 (d, 1H), 6.91 (t, 1H), 5.55 (d, 1H), 5.27 (d, 1H), 5.23 (d, 1H), 4.40-4.32 m, 1H), 4.17-4.11 (m, 2H), 4.06 (q, 2H), 3.62-3.60 (m, 2H), 3.22 (s, 3H), 3.17 (dd, 1H), 2.88 (dd, 1H), 1.18 (t, 3H)

Step B: Ethyl (2R)-2-[5-bromo-6-(4-fluorophenyl)thieno[2,3-d]pyrimidin-4-yl]oxy-3-[2-[[2-[2-(2-methoxyethoxy)phenyl]pyrimidin-4-yl]methoxy]phenyl]propanoate A suspension of 995 mg product obtained in Step A (2.2 mmol, 1.1 eq.), 687 mg 5-bromo-4-chloro-6-(4-fluorophenyl)thieno[2,3-d]pyrimidine (from Preparation 1 Step D) (2 mmol, 1 eq.) and 1.95 g cesium carbonate (6 mmol, 3 eq.) in 10 mL dry THF were stirred at 70° C. until no further conversion was observed. The reaction mixture was diluted with EtOAc and brine. After extraction the organic phase was washed with brine and dried over MgSO$_4$, filtered and concentrated under reduced pressure. The crude product was purified by flash chromatography using heptane and EtOAc as eluents to obtain ethyl (2R)-2-[5-bromo-6-(4-fluorophenyl)thieno[2,3-d]pyrimidin-4-yl]oxy-3-[2-[[2-[2-(2-methoxyethoxy)phenyl]pyrimidin-4-yl]methoxy]phenyl]propanoate. $^1$H NMR (400 MHz, DMSO-d$_6$) δ 8.90 (d, 1H), 8.62 (s, 1H), 7.77-7.72 (m, 2H), 7.61 (d, 1H), 7.55 (dd, 1H), 7.49 (dd, 1H), 7.45-7.38 (m, 3H), 7.25 (dd, 1H), 7.15 (d, 1H), 7.09-7.01 (m, 2H), 6.94 (t, 1H), 5.79 (dd, 1H), 5.31 (d, 1H), 5.25 (d, 1H), 4.17 (q, 2H), 4.15-4.10 (m, 2H), 3.64-3.56 (m, 3H), 3.33 (dd, 1H), 3.21 (s, 3H), 1.14 (t, 3H)

Step C: Ethyl (2R)-2-[5-bromo-6-(4-fluorophenyl)thieno[2,3-d]pyrimidin-4-yl]oxy-3-[2-[[2-[2-(2-hydroxyethoxy)phenyl]pyrimidin-4-yl]methoxy]phenyl]propanoate To the solution of 760 mg product obtained in Step B (1 mmol, 1 eq.) in 10 mL dry DCM, 1 mL BBr$_3$ (1 mmol, 1M in DCM, 1 eq.) was added dropwise at r.t., then the mixture was stirred until no further conversion was observed. The reaction mixture was diluted with EtOAc and brine. After extraction the organic phase was washed with brine and dried over MgSO$_4$, filtered and concentrated under reduced pressure. The crude product was purified by flash chromatography using heptane and EtOAc as eluents to obtain ethyl (2R)-2-[5-bromo-6-(4-fluorophenyl)thieno[2,3-d]pyrimidin-4-yl]oxy-3-[2-[[2-[2-(2-hydroxyethoxy)phenyl]pyrimidin-4-yl]methoxy]phenyl]propanoate. $^1$H NMR (400 MHz, CDCl$_3$) δ 8.99 (d, 1H), 8.53 (s, 1H), 7.92 (dd, 1H), 7.79 (d, 1H), 7.69-7.62 (m, 2H), 7.54-7.45 (m, 2H), 7.27-7.12 (m, 5H), 6.98 (7, 1H), 6.94 (d, 1H), 5.87 (dd, 1H), 5.34 (d, 1H), 5.29 (d, 1H), 4.41 (t, 2H), 4.29 (q, 2H), 3.94 (t, 2H), 3.72 (dd, 1H), 3.42 (dd, 1H), 1.28 (t, 3H)

Step D: Ethyl (2R)-2-[5-[3-chloro-2-methyl-4-[2-(4-methylpiperazin-1-yl)ethoxy]phenyl]-6-(4-fluorophenyl)thieno[2,3-d]pyrimidin-4-yl]oxy-3-[2-[[2-[2-(2-hydroxyethoxy)phenyl]pyrimidin-4-yl]methoxy]phenyl]propanoate To a solution of 200 mg of product Step C (0.27 mmol, 1 eq.) in 4 mL dioxane/H$_2$O (1:1), 127 mg 1-[2-[2-chloro-3-methyl-4-(4,4,5,5-tetramethyl-1,3,2-dioxaborolan-2-yl)phenoxy]ethyl]-4-methyl-piperazine (from Preparation 1 Step L) (0.32 mmol, 1.2 eq.), 3.1 mg Pd(OAc)$_2$ (0.05 eq.), 11 mg AtaPhos (0.1 eq.) and 262 mg cesium carbonate (0.8 mmol, 3 eq.) were stirred at 70° C. until no further conversion was observed. Reaction mixture was diluted with EtOAc and brine. After extraction the organic phase was washed with brine and dried over MgSO$_4$, filtered and concentrated under reduced pressure. Crude product was purified by flash chromatography using EtOAc/MeOH (containing 1.2% NH$_3$) as eluents to obtain ethyl (2R)-2-[5-[3-chloro-2-methyl-4-[2-(4-methylpiperazin-1-yl)ethoxy]phenyl]-6-(4-fluorophenyl)thieno[2,3-d]pyrimidin-4-yl]oxy-3-[2-[[2-[2-(2-hydroxyethoxy)phenyl]pyrimidin-4-yl]methoxy]phenyl]propanoate. MS: $[M+H]^+$=933.2

Step E: Example 26

To a solution of 120 mg product of Step D (0.13 mmol) in 4 mL dioxane/H$_2$O (1:1) 100 mg LiOH×H$_2$O (2.6 mmol, 20 eq.) was added and it was stirred at r.t. until no further conversion was observed. Then it was neutralized with 2M HCl and then directly was injected to an RP18 column using 5 mM aqueous $NH_4HCO_3$ solution and MeCN as eluents. The diastereoisomer eluting later was collected to obtain Example 26. HRMS calculated for $C_{48}H_{46}ClFN_6O_7S$: 904.2821; found 453.1496 $(M+2H)^{2+}$.

Example 27

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{2-[(2,3-dihydroxypropoxy)methyl]phenyl}pyrimidin-4-yl)methoxy]phenyl}propanoic acid

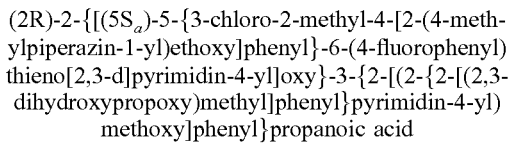

Starting from Preparation 1 and Preparation 4f using General Procedure I, after completion of the reaction in Step B the pH was set to 1 with 2M aqueous HCl solution and it was stirred until no further conversion was observed. Then it was neutralized with 10% aqueous $K_2CO_3$ solution, diluted with brine, extracted with DCM. The combined organic phases were dried over $MgSO_4$, filtered and the filtrate was concentrated under reduced pressure. The crude product was purified via preparative reversed phase chromatography using 5 mM aqueous $NH_4HCO_3$ solution and MeCN as eluents. The diastereoisomer eluting later was collected to obtain Example 27. HRMS calculated for $C_{50}H_{50}ClFN_6O_8S$: 948.3083; found 475.1621 $(M+2H)^{2+}$.

Example 28

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[3-(phosphonooxy)phenyl]pyrimidin-4-yl}methoxy)phenyl]propanoic acid

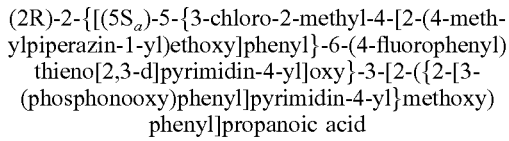

To a THF solution of 444 mg Preparation 2 (0.5 mmol, 1 eq.) and 210 µL, TEA (1.5 mmol, 3 eq.) in 5 mL dry THF, 140 µL, (1.5 mmol, 3 eq.) $POCl_3$ was added dropwise at r.t. After 15 minutes stirring, 5 mL sodium hydroxide (10 mmol, 2M in water) was added, and then it was stirred at 50° C. until no further conversion was observed. The reaction mixture was injected directly to a preconditioned (EtOAc/MeOH [containing 1.2% $NH_3$]—80/20) 220 g flash silica gel column using EtOAc/MeOH (containing 1.2% $NH_3$) as eluents with gradient method giving the desired product as a mixture of the diastereoisomers. The diastereoisomers were separated via preparative reversed phase chromatography using 50 mM aqueous $NH_4HCO_3$ solution and MeOH as eluents. The diastereoisomer eluting later was collected as Example 28. HRMS calculated for $C_{46}H_{43}N_6O_9FPSCl$: 940.2222; found 471.1194 $(M+2H)^{2+}$.

Example 29

4-[4-({2-[(2R)-2-carboxy-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}ethyl]phenoxy}methyl)pyrimidin-2-yl]phenyl phosphate

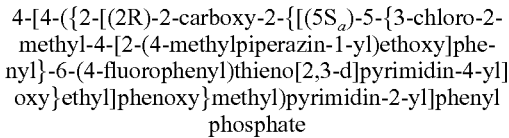

To a THF solution of 444 mg ethyl Preparation 3 (0.5 mmol, 1 eq.) and 210 µL, TEA (1.5 mmol, 3 eq.) in 5 mL dry THF, 140 µL, (1.5 mmol, 3 eq.) $POCl_3$ was added dropwise at r.t. After 15 minutes stirring, 5 mL sodium hydroxide (10 mmol, 2M in water) was added, and then it was stirred at 50° C. until no further conversion was observed. The reaction mixture was injected directly to a preconditioned (EtOAc/MeOH [containing 1.2% $NH_3$]—80/20) 220 g flash silica gel column using EtOAc/MeOH (containing 1.2% $NH_3$) as eluents with gradient method giving the desired product as a mixture of the diastereoisomers. The diastereoisomer eluting later was collected as Example 29 after lyophylisation. HRMS calculated for $C_{46}H_{43}N_6O_9FPSCl$: 940.2222; found 471.1188 $(M+2H)^{2+}$.

Example 30

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[3-(2-hydroxyethoxy)phenyl]pyrimidin-4-yl-}methoxy)phenyl]propanoic acid

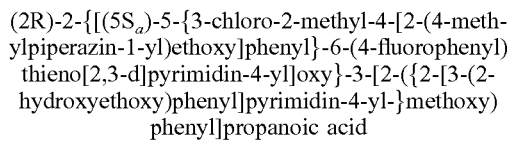

Step A: Ethyl (2R)-2-[5-[3-chloro-2-methyl-4-[2-(4-methylpiperazin-1-yl)ethoxy]phenyl]-6-(4-fluorophenyl)thieno[2,3-d]pyrimidin-4-yl]oxy-3-[2-[[2-[3-[2-(p-tolylsulfonyloxy) ethoxy]phenyl]pyrimidin-4-yl]methoxy]phenyl]propanoate To a DMF solution of 178 mg Preparation 2 (0.2 mmol), 195 mg cesium carbonate (0.6 mmol) and 222 mg 2-(p-tolylsulfonyloxy)ethyl 4-methylbenzenesulfonate (0.6 mmol) were added and the mixture was stirred at 60° C. until no further conversion was observed. The reaction mixture was diluted with EtOAc and brine. After extraction the organic phase was washed with brine and dried over $MgSO_4$, filtered and concentrated under reduced pressure. The crude product was purified by flash chromatography using EtOAc and MeOH (containing 1.2% $NH_3$) as eluents to obtain ethyl (2R)-2-[5-[3-chloro-2-methyl-4-[2-(4-methylpiperazin-1-yl)ethoxy]phenyl]-6-(4-fluorophenyl)thieno[2,3-d]pyrimidin-4-yl]oxy-3-[2-[[2-[3-[2-(p-tolylsulfonyloxy)ethoxy]phenyl]pyrimidin-4-yl]methoxy]phenyl]propanoate. MS: $[M+H]^+=1087.2$ Step B: Example 30

To a solution of 120 mg product Step A (0.11 mmol) in 4 mL dioxane/$H_2O$ (1:1), 92 mg LiOH×$H_2O$ (2.2 mmol) was added and it was stirred at 60° C. until no further conversion was observed. Then it was neutralized with 2M HCl and then was injected directly to an RP18 column using using 5 mM aqueous $NH_4HCO_3$ solution and MeCN as eluents. The diastereoisomer eluting later was collected to obtain Example 30. HRMS calculated for $C_{48}H_{46}ClFN_6O_7S$: 904.2821; found 453.1475 $(M+2H)^{2+}$.

Example 31

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{4-[2-(2-methoxyethoxy)ethoxy]phenyl}pyrimidin-4-yl)methoxy]phenyl}propanoic acid

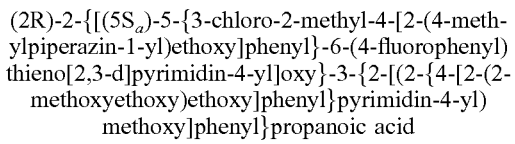

Starting from Preparation 3 and 2-(2-methoxyethoxy)ethanol using General procedure II, Example 31 was obtained. HRMS calculated for $C_{51}H_{52}N_6O_8FSCl$: 962.324; found 482.1703 $(M+H)^{2+}$

Example 32

(2R)-2-{[(5S$_a$)-5-{3-chloro-2-methyl-4-[2-(4-methylpiperazin-1-yl)ethoxy]phenyl}-6-(4-fluorophenl)thieno[2,3d]-pyrimidin-4-yl]oxy}-3-{2-[(2-{4-[2-(2-hydroxyethoxy)ethoxy]phenyl}pyrimidin-4-yl)methoxy]phenyl}propanoic acid Starting from Preparation 3 and 10 eq. of 2-(2-hydroxyethoxy)ethanol using General procedure II, Example 32 was obtained. HRMS calculated for C$_{50}$H$_{50}$N$_6$O$_8$FSCl: 948.3083; found 475.1613 (M+2H)$^{2+}$.

Example 33

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(4-{2-[2-(2-methoxyethoxy)ethoxy]ethoxy}phenyl)pyrimidin-4-yl]methoxy}phenyl)propanoic acid Starting from Preparation 3 and 2-[2-(2-methoxyethoxy)ethoxy]ethanol using general procedure II, Example 33 was obtained. HRMS calculated for C$_{53}$H$_{56}$N$_6$O$_9$FSCl: 1006.3502; found 504.183 (M+2H)$^{2+}$.

Example 34

(2R)-2-{[(5S$_a$)-5-{3-chloro-2-methyl-4-[2-(4-methylpiperazin-1-yl)ethoxy]phenyl}-6-(4-flurophenyl)thieno[2,3-d]pyrimidin-4-yl]oxy}-3-{2-[(2-{4-[2-(dimethylamino)ethoxy]phenyl}pyrimidin-4-yl)methoxy]phenyl}propanoic acid Starting from Preparation 3 and 2-(dimethylamino)ethanol using General procedure II, Example 34 was obtained. HRMS calculated for C$_{50}$H$_{51}$N$_7$O$_6$FSCl: 931.3294; found 466.6709 (M+2H)$^{2+}$

Example 35

(2R) -2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[(2,2-dimethyl-1,3-dioxolan-4-yl)methoxy]phenyl}pyrimidin-4-yl)methoxy]phenyl}propanoic acid Starting from Preparation 2 and (2,2-dimethyl-1,3-dioxolan-4-yl)methanol using General procedure II, Example 35 was obtained. HRMS calculated for C$_{52}$H$_{52}$N$_6$O$_8$FSCl: 974.324; found 488.1677 (M+2H)$^{2+}$.

Example 36

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[3-(15-hydroxy-3-oxo-2,7,10,13-tetraoxa-4-azapentadec-1-yl)phenyl]pyrimidin-4-yl}methoxy)phenyl]propanoic acid Starting from Preparation 5 and 2-[2-[2-(2-aminoethoxy)ethoxy]ethanol as the appropriate amine using General procedure III, Example 36 was obtained. HRMS calculated for C$_{56}$H$_{61}$ClFN$_7$O$_{11}$S: 1093.3822; found 547.7006 (M+2H)$^{2+}$.

Example 37

(2R)-3-(2-{[2-(3-{[(1,4'-bipiperidin-1'-ylcarbonyl)oxy]methyl}phenyl)pyrimidin-4-yl]methoxy}phenyl)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid Starting from Preparation 5 and 1-(4-piperidyl)piperidine as the appropriate amine using General procedure III, Example 37 was obtained. HRMS calculated for C$_{58}$H$_{62}$ClFN$_8$O$_7$S: 1068.4135; found 1069.419 (M+H)$^+$.

Example 38

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3-{2-[2-(2-hydroxyethoxy)ethoxy]ethoxy}phenyl)pyrimidin-4-yl]methoxy}phenyl)propanoic acid Starting from Preparation 2 and 10 eq. of 2-[2-(2-hydroxyethoxy)ethoxy]ethanol using General procedure II, Example 38 was obtained. HRMS calculated for C$_{52}$H$_{54}$ClFN$_6$O$_9$S: 992.3345; found 497.1748 (M+2H)$^{2+}$.

Example 39

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[2-(2-hydroxy ethoxy)ethoxy]phenyl}pyrimidin-4-yl)methoxy]phenyl}propanoic acid Starting from Preparation 2 and 10 eq. of 2-(2-hydroxyethoxy)ethanol using General procedure II, Example 39 was obtained. HRMS calculated for C$_{50}$H$_{50}$ClFN$_6$O$_8$S: 948.3083; found 475.1604 (M+2H)$^{2+}$.

Example 40

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[2-(2-methoxy ethoxy)ethoxy]phenyl}pyrimidin-4-yl)methoxy]phenyl}propanoic acid Starting from Preparation 2 and 2-(2-methoxyethoxy)ethanol using General procedure II, Example 40 was obtained. HRMS calculated for C$_{51}$H$_{52}$ClFN$_6$O$_8$S: 962.324; found 482.1675 (M+2H)$^{2+}$

Example 41

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[({[2-(4-methylpiperazin-1-yl)ethyl]carbamoyl}oxy)methyl]phenyl}pyrimidin-4-yl)methoxy]phenyl}propanoic acid Starting from Preparation 5 and 2-(4-methylpiperazin-1-yl)ethanamine as the appropriate amine using General procedure III, Example 41 was obtained. HRMS calculated for C$_{55}$H$_{59}$ClFN$_9$O$_7$S: 1043.3931; found 522.7052 (M+2H)$^{2+}$.

Example 42

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[({[2-(morpholin-4-yl)ethyl]carbamoyl}oxy)methyl]phenyl}pyrimidin-4-yl)methoxy]phenyl}propanoic acid Starting from Preparation 5 and 2-morpholinoethanamine as the appropriate amine using General procedure III, Example 42 was obtained. HRMS calculated for $C_{54}H_{56}ClFN_8O_8S$: 1030.3615; found 516.1871 (M+2H)$^{2+}$.

Example 43

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[({[2-(dimethylamino)ethyl]carbamoyl}oxy)methyl]phenyl}pyrimidin-4-yl)methoxy]phenyl}propanoic acid Starting from Preparation 5 and N',N'-dimethylethane-1,2-diamine as the appropriate amine using General procedure III, Example 43 was obtained. HRMS calculated for $C_{52}H_{54}ClFN_8O_7S$: 988.3509; found 989.3586 (M+H)$^+$.

Example 44

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[({[2-(pyrrolidin-1-yl)ethyl]carbamoyl}oxy)methyl]phenyl}pyrimidin-4-yl)methoxy]phenyl}propanoic acid Starting from Preparation 5 and 2-pyrrolidin-1-ylethanamine as the appropriate amine using General procedure III, Example 44 was obtained. HRMS calculated for $C_{54}H_{56}ClFN_8O_7S$: 1014.3665; found 508.1916 (M+2H)$^{2+}$.

Example 45

(2R)-3-[2-({2-[3-({[bis(2-methoxyethyl)carbamoyl]oxy}methyl)phenyl]pyrimidin-4-yl}methoxy)phenyl]-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid Starting from Preparation 5 and 2-methoxy-N-(2-methoxyethyl)ethanamine as the appropriate amine using General procedure III, Example 45 was obtained. HRMS calculated for $C_{54}H_{57}N_7O_9FSCl$: 1033.3611; found 517.6883 (M+2H)$^{2+}$.

Example 46

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3-{[(1,4,7,10,13-pentaoxa-16-azacyclooctadecan-16-ylcarbonyl)oxy]methyl}phenyl)pyrimidin-4-yl]methoxy}phenyl)propanoic acid Starting from Preparation 5 and 1,4,7,10,13-pentaoxa-16-azacyclooctadecane as the appropriate amine using General procedure III, Example 46 was obtained. HRMS calculated for $C_{60}H_{67}N_7O_{12}FSCl$: 1163.4241; found 582.7187 (M+2H)$^{2+}$.

Example 47

(2R)-2-{[(5S$_a$)-5-{3-chloro-2-methyl-4-[2-(4-methylpiperazin-1-yl) ethoxy]phenyl}-6-(4-fluorophenyl)thieno[2,3-d]pyrimidin-4-yl]oxy}-3-[2-({2-[3-(2,3-dihydroxypropoxy)phenyl]pyrimidin-4-yl}methoxy)phenyl]propanoic acid Starting from Preparation 2 and (2,2-dimethyl-1,3-dioxolan-4-yl)methanol using General procedure II, after completion of the reaction in Step B the pH was set to 1 with 2M aqueous HCl solution and it was stirred until no further conversion was observed. Then it was neutralized with 10% aqueous $K_2CO_3$ solution, diluted with brine, extracted with DCM. The combined organic phases were dried over $MgSO_4$, filtered and the filtrate was concentrated under reduced pressure. The crude product was purified via preparative reversed phase chromatography using 5 mM aqueous $NH_4HCO_3$ solution and MeCN as eluents. The diastereoisomer eluting later was collected to obtain Example 47. HRMS calculated for $C_{49}H_{48}N_6O_8FSCl$: 934.2927; found 468.1538 (M+2H)$^{2+}$.

Example 48

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3-{2-[2-(2-methoxyethoxy)ethoxy]ethoxy}phenyl)pyrimidin-4-yl]methoxy}phenyl)propanoic acid Starting from Preparation 2 and 2-[2-(2-methoxyethoxy)ethoxy]ethanol using General procedure II, Example 48 was obtained. HRMS calculated for $C_{53}H_{56}N_6O_9FSCl$: 1006.3502; found 504.1829 (M+2H)$^{2+}$.

Example 49

(2R)-3-(2-{[2-(3-{2-[bis(2-hydroxyethyl)amino]ethoxy}phenyl)pyrimidin-4-yl]methoxy}phenyl)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid Starting from Preparation 2 and 10 eq. of 2-[bis(2-hydroxyethyl)amino]ethanol using General procedure II, Example 49 was obtained. HRMS calculated for $C_{52}H_{55}N_7O_8FSCl$: 991.3505; found 496.6833 (M+2H)$^{2+}$.

Example 50

(2R)-2-{[(5S$_a$)-5-{2,3-dimethyl-4-[2-(4-methylpiperazin-1-yl)ethoxy]phenyl}-6-(4-fluorophenyl)thieno[2,3-d]pyrimidin-4-yl]oxy}-3-{2-[(2-{3-[({[2-(piperidin-1-yl)ethyl]carbamoyl}oxy)methyl]phenyl}pyrimidin-4-yl)methoxy]phenyl}propanoic acid Starting from Preparation 5 and N-(2-aminoethyl)piperidine as the appropriate amine using General procedure III, Example 50 was obtained. HRMS calculated for $C_{55}H_{58}ClFN_8O_7S$: 1028.3822; found 1029.3893 (M+H)$^+$.

Example 51

(2R)-2-{[(5S$_a$)-5-{3-chloro-2-methyl-4-[2-(4-meth-ylpiperazin-1-yl)ethoxy]phenyl}-6-(4-fluorophenyl)thieno[2,3-d]pyrimidin-4-yl]oxy}-3-{2-[(2-{3-[2-(morpholin-4-yl)ethoxy]phenyl}pyrimidin-4-yl)methoxy]phenyl}propanoic acid Starting from Preparation 2 and N-(2-hydroxyethyl)morpholine using General procedure II, Example 51 was obtained. HRMS calculated for C$_{52}$H$_{53}$ClFN$_7$O$_7$S: 973.3400; found 487.6785 (M+2H)$^{2+}$.

Example 52

(2R)-2-{[(5S$_a$)-5-{3-chloro-2-methyl-4-[2-(4-meth-ylpiperazin-1-yl)ethoxy]phenyl}-6-(4-fluorophenyl)thieno[2,3-d]pyrimidin-4-yl]oxy}-3-{2-[(2-{3-[2-(dimethyl amino)ethoxy]phenyl}pyrimidin-4-yl)methoxy]phenyl}propanoic acid Starting from Preparation 2 and 2-dimethylaminoethanol using General procedure II, Example 52 was obtained. HRMS calculated for C$_{50}$H$_{51}$ClFN$_7$O$_6$S: 931.3294; found 466.6722 (M+2H)$^{2+}$

Example 53

(2R)-3-(2-{[2-(4-{2-[bis(2-hydroxyethyl)amino]ethoxy}phenyl)pyrimidin-4-yl]methoxy}phenyl)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid Starting from Preparation 3 and 2-[bis(2-hydroxyethyl)amino]ethanol using General procedure II, Example 53 was obtained. HRMS calculated for C$_{52}$H$_{55}$N$_7$O$_8$FSCl: 991.3505; found 496.6822 (M+2H)$^{2+}$.

Example 54

(2R)-2-{[(5S$_a$)-5-{3-chloro-2-methyl-4-[2-(4-meth-ylpiperazin-1-yl)ethoxy]phenyl}-6-(4-fluorophenyl)thieno[2,3-d]pyrimidin-4-yl]oxy}-3-(2-{[2-(4-{2-[2-(2-hydroxyethoxy)ethoxy]ethoxy}phenyl)pyrimidin-4-yl]methoxy}phenyl)propanoic acid Starting from Preparation 3 and 10 eq. of triethyleneglycol using General procedure II, Example 54 was obtained. HRMS calculated for C$_{52}$H$_{54}$N$_6$O$_9$FSCl: 992.3345; found 497.1743 (M+2H)$^{2+}$

Example 55

(2R)-2-{[(5S$_a$)-5-{3-chloro-2-methyl-4-[2-(4-meth-ylpiperazin-1-yl)ethoxy]phenyl}-6-(4-fluorophenyl)thieno[2,3-d]pyrimidin-4-yl]oxy}-3-{2-[(2-{4-[(2,2-dimethyl-1,3-dioxolan-4-yl)methoxy]phenyl}pyrimidin-4-yl)methoxy]phenyl}propanoic acid Starting from Preparation 3 and (2,2-dimethyl-1,3-dioxolan-4-yl)methanol using General procedure II, Example 55 was obtained. HRMS calculated for C$_{52}$H$_{52}$N$_6$O$_8$FSCl: 974.3240; found 488.1689 (M+2H)$^{2+}$.

Example 56

(2R)-2-{[(5S$_a$)-5-{3-chloro-2-methyl-4-[2-(4-meth-ylpiperazin-1-yl)ethoxy]phenyl}-6-(4-fluorophenyl)thieno[2,3-d]pyrimidin-4-yl]oxy}-3-{2-[(2-{4-[2-(morpholin-4-yl)ethoxy]phenyl}pyrimidin-4-yl)methoxy]phenyl}propanoic acid Starting from Preparation 3 and N-(2-hydroxyethyl)morpholine using General procedure II, Example 56 was obtained. HRMS calculated for C$_{52}$H$_{53}$N$_7$O$_7$FSCl: 973.3400; found 487.6775 (M+2H)$^{2+}$.

Example 57

4-[4-({2-[(2R)-2-carboxy-2-{[(5S$_a$)-5-{3-chloro-2-methyl-4-[2-(4-methylpiperazin-1 yl)ethoxy]phe-nyl}-6-(4-fluorophehnyl)thieno[2,3-d]pyrimidin-4-yl]oxy}ethyl]phenoxy}methyl)pyrimidin-2-yl]phenyl phosphate disodium salt To a THF solution of 444 mg Preparation 3 (0.5 mmol, 1 eq.) and 210 µL TEA (1.5 mmol, 3 eq.) in 5 mL dry THF, 140 µL POCl$_3$ (1.5 mmol, 3 eq.) was added dropwise at r.t. After 15 minutes stirring, 5 mL sodium hydroxide (10 mmol, 2M in water) was added, and then it was stirred at 50° C. until no further conversion was observed. Then the pH was adjusted to 6 with TFA, and then this reaction mixture directly was injected to an RP18 column using 50 mM aqueous NH$_4$HCO$_3$ solution and MeOH as eluents. The diastereoisomer eluting later was collected. After liophilisation the remaining white solid was suspended in 5 mL dioxan/saturated NH$_4$HCO$_3$ (1:1). After 1 hour stirring at r.t., reaction mixture directly was injected to an RP18 column using water and MeCN as eluents giving Example 57. HRMS calculated for C$_{46}$H$_{43}$N$_6$O$_9$FPSCl: 940.2222; found 469.1054 (M−2H)$^{2-}$.

Example 58

(2R)-3-(2-{[2-(2-{2-[bis(2-hydroxyethyl)amino]ethoxy}phenyl)pyrimidin-4-yl]methoxy}phenyl)-2-{((5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid

Example 59

(2R)-3-(2-{[2-(4-{[bis(2-hydroxyethyl)amino]methyl}phenyl)pyrimidin-4-yl]methoxy}phenyl)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid

Example 60

(2R)-3-(2-{[2-(3-{[bis(2-hydroxyethyl)amino]methyl}phenyl)pyrimidin-4-yl]methoxy}phenyl)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid

Example 61

(2R)-3-(2-{[2-(2-{[bis(2-hydroxyethyl)amino]methyl}phenyl)pyrimidin-4-yl]methoxy}phenyl)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid

Example 62

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{4-[(2-hydroxy ethoxy)methyl]phenyl}pyrimidin-4-yl)methoxy]phenyl}propanoic acid

Example 63

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{2--[2-(2-hydroxy ethoxy)ethoxy]phenyl}pyrimidin-4-yl)methoxy]phenyl}propanoic acid

Example 64

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-{2-[2-(2-hydroxyethoxy)ethoxy]ethoxy}phenyl)pyrimidin-4-yl]methoxy}phenyl)propanoic acid

Example 65

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[(phosphono oxy)methoxy]phenyl}pyrimidin-4-yl)methoxy]phenyl}propanoic acid

Example 66

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3-{[(phosphono oxy)methoxy]methyl}phenyl)pyrimidin-4-yl]methoxy}phenyl)propanoic acid

Example 67

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3-{[(phosphono oxy)carbonyl]oxy}phenyl)pyrimidin-4-yl]methoxy}phenyl)propanoic acid

Example 68

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[3-({[(phosphono oxy)carbonyl]oxy}methyl)phenyl]pyrimidin-4-yl}methoxy)phenyl]propanoic acid

Example 69: 1

1-[(ethoxycarbonyl)oxy]ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[(1,3-dimethoxypropan-2-yl)oxy]phenyl}pyrimidin-4-yl)methoxy]phenyl}propanoate

Step A: ethyl 1-chloroethyl Carbonate 1 eq. of ethanol and 1.2 eq. pyridine were dissolved in dichloromethane (1.2 mL/mmol). 1.05 eq. 1-chloroethyl chloroformate was slowly added at −78° C. under nitrogen and the reaction mixture was stirred at −78° C. for 3 hours. The cold mixture was filtered and the filtrate was concentrated under reduced pressure. The crude product was used without further purification.

Step B: Example 69

1 eq. of Example 13 was dissolved in DMF (20 ml/mmol) under nitrogen. 6.7 eq. Cs$_2$CO$_3$ and 8 eq. of ethyl 1-chloroethyl carbonate from Step A was added. The reaction mixture was stirred at room temperature until no further conversion was observed. The mixture was diluted with brine and it was extracted with DCM, dried with Na$_2$SO$_4$, filtered and concentrated under reduced pressure. The crude product was purified via preparative reverse phase chromatography using 5 mM aqueous NH$_4$HCO$_3$ solution and acetonitrile as eluents to obtain Example 69. HRMS calculated for C$_{56}$H$_{60}$ClFN$_6$O$_{11}$S: 1078.3713; found 1079.3796 and 1079.3786 (M+H)

Example 70

1-[(dimethylcarbamoyl)oxy]ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[(1,3-dimethoxypropan-2-yl)oxy]phenyl}pyrimidin-4-yl)methoxy]phenyl}propanoate

Example 71

(2R)-2-{[5-{2,6-dimethyl-4-[2-(4-methylpiperazin-

Example 72

(2R)-2-{[5-{3,5-dichloro-2,6-dimethyl-4-[2-(4-methylpiperazin-1-yl) ethoxy]phenyl}-6-(4-fluorophenyl)thieno[2,3-d]pyrimidin-4-yl]oxy}-3-[2-({2-[3-(hydroxymethyl)phenyl]pyrimidin-4-yl}methoxy)phenyl]propanoic acid

Example 73

(2R)-2-{[5-{2,6-dimethyl-4-[2-(4-methylpiperazin-1-yl)ethoxy]phenyl}-6-(4-fluorophenyl)thieno[2,3-d]pyrimidin-4-yl]oxy}-3-[2-({2-[4-(phosphonooxy)phenyl]pyrimidin-4-yl}methoxy)phenyl]propanoic acid

Example 74

(2R)-2-{[5-{3,5-dichloro-2,6-dimethyl-4-[2-(4-methylpiperazin-1-yl) ethoxy]phenyl}-6-(4-fluorophenyl)thieno[2,3-d]pyrimidin-4-yl]oxy}-3-[2-({2-[4-(phosphonooxy)phenyl]pyrimidin-4-yl}methoxy)phenyl]propanoic acid

Example 75

2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-hydroxy-3-[2-({2-[3-(hydroxymethyl)phenyl]pyrimidin-4-yl}methoxy)phenyl]propanoic acid

Example 76

2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-4-hydroxy-3-[2-({2-[3-(hydroxymethyl)phenyl]pyrimidin-4-yl}methoxy)phenyl]butanoic acid

Example 77

2-O-[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]-3,4-dideoxy-3-[2-({2-[3-(hydroxymethyl)phenyl]pyrimidin-4-yl}methoxy)phenyl]pentonic acid

Example 78

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[2-(hydroxy methyl)pyridin-4-yl]pyrimidin-4-yl}methoxy)phenyl]propanoic acid

Example 79

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[5-(hydroxy methyl)pyridin-3-yl]pyrimidin-4-yl}methoxy)phenyl]propanoic acid Starting from Preparation 1 and [5-(4,4,5,5-tetramethyl-1,3,2-dioxaborolan-2-yl)-3-pyridyl]methanol using General procedure I, Example 79 was obtained. HRMS calculated for $C_{46}H_{43}ClFN_7O_6S$: 875.2668; found 438.6428 $(M+2H)^{2+}$.

Example 80

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[6-(hydroxy methyl)pyridazin-4-yl]pyrimidin-4-yl}methoxy)phenyl]propanoic acid

Example 81

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[6-(hydroxy methyl)pyrazin-2-yl]pyrimidin-4-yl}methoxy)phenyl]propanoic acid

Example 82

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2'-(hydroxy methyl)-2,5'-bipyrimidin-4-yl]methoxy}phenyl)propanoic acid Starting from Preparation 1 and Preparation 4q using General procedure I, Example 82 was obtained. HRMS calculated for $C_{45}H_{42}ClFN_8O_6S$: 876.2621; found 439.1402 $(M+2H)^{2+}$.

PHARMACOLOGICAL STUDY

Example A

Inhibition of Mcl-1 by the Fluorescence Polarisation Technique

The relative binding potency of each compound was determined via Fluorescence Polarisation (FP). The method utilised a Fluorescein labelled ligand (Fluorescein-βAla-Ahx-A-REIGAQLRRMADDLNAQY-OH; mw 2,765) which binds to the Mcl-1 protein (such that Mcl-1 corresponds to the UniProtKB® primary accession number: Q07820) leading to an increased anisotropy measured in milli-polarisation (mP) units using a reader. The addition of a compound which binds competitively to the same site as the ligand will result in a greater proportion of unbound ligand in the system indicated by a decrease in mP units.

An 11 point serial dilution of each compound was prepared in DMSO and 2 µl transferred into flat bottomed, low binding, 384-well plate (final DMSO concentration 5%). 38

µl of buffer (10 mM 4-(2-hydroxyethyl)-1-piperazineethanesulfonic acid [HEPES], 150 mM NaCl, 0.05% Tween 20, pH 7.4), containing the Fluorescein labelled ligand (final concentration 1 nM) and Mcl-1 protein (final concentration 5 nM) was then added.

Assay plates were incubated ~2 hours at r.t. before FP was measured on a Biomek Synergy2 reader (Ex. 528 nm, Em. 640 nm, Cut off 510 nm) and mP units calculated. The binding of increasing doses of test compound was expressed as a percentage reduction in mP compared to a window established between '5% DMSO only' and '100% inhibition' controls. 11-point dose response curves were plotted with XL-Fit software using a 4-Parameter Logistic Model (Sigmoidal Dose-Response Model) and the inhibitory concentrations that gave a 50% reduction in mP ($IC_{50}$) were determined. Results obtained are presented in Table 1 below.

The results show that the compounds of the invention inhibit interaction between the Mcl-1 protein and the fluorescent peptide described hereinbefore.

Example B

In Vitro Cytotoxicity

The cytotoxicity studies were carried out on the H929 multiple myeloma tumour line.

The cells are distributed onto microplates and exposed to the test compounds for 48 hours.

The cell viability is then quantified by a colorimetric assay, the Microculture Tetrazolium Assay (Cancer Res., 1987, 47, 939-942).

The results are expressed in $IC_{50}$ (the concentration of compound that inhibits cell viability by 50%) and are presented in Table 1 below.

The results show that the compounds of the invention are cytotoxic.

TABLE 1

$IC_{50}$ of Mcl-1 inhibition (fluorescence polarisation test) and of cytotoxicity for H929 cells

|  | $IC_{50}$ (M) Mcl-1 FP | $IC_{50}$ (M) MTT H929 |
| --- | --- | --- |
| Example 1 | 8.4E−09 | 9.31E−09 |
| Example 2 | 1.32E−08 | 1.59E−08 |
| Example 3 | 4.05E−09 | 4.08E−09 |
| Example 4 | 4.9E−09 | 3.64E−09 |
| Example 5 | 3.7E−09 | 1.65E−09 |
| Example 6 | 1.57E−08 | 3.25E−09 |
| Example 7 | 3.75E−09 | 4.45E−09 |
| Example 8 | 7.35E−09 | 2.07E−09 |
| Example 9 | 8.15E−09 | 1.40E−09 |
| Example 10 | 1.09E−08 | 2.79E−09 |
| Example 11 | 4.05E−09 | 1.99E−09 |
| Example 12 | 4.25E−09 | 3.82E−09 |
| Example 13 | 5.1E−09 | 3.59E−09 |
| Example 14 | 6.15E−09 | 3.37E−09 |
| Example 15 | 2.75E−09 | 3.59E−09 |
| Example 16 | 7.2E−09 | 3.71E−08 |
| Example 17 | 4.8E−09 | 3.03E−09 |
| Example 18 | 4.1E−09 | 1.39E−08 |
| Example 19 | 4.95E−09 | 2.47E−09 |
| Example 20 | 4.35E−09 | 5.68E−08 |
| Example 21 | 4.85E−09 | >1.50E−07 |
| Example 22 | 5.5E−09 | 5.97E−09 |
| Example 23 | 2.7E−09 | 3.97E−08 |
| Example 24 | 3.15E−09 | 2.55E−09 |
| Example 25 | 3.45E−09 | 1.00E−08 |
| Example 26 | 3.45E−09 | 1.72E−09 |
| Example 27 | 2.2E−09 | 1.39E−08 |
| Example 28 | 4.15E−09 | 4.84E−08 |
| Example 29 | 4.6E−09 | 2.27E−08 |
| Example 30 | 4.5E−09 | 3.60E−09 |

TABLE 1-continued $IC_{50}$ of Mcl-1 inhibition (fluorescence polarisation test) and of cytotoxicity for H929 cells

|  | $IC_{50}$ (M) Mcl-1 FP | $IC_{50}$ (M) MTT H929 |
| --- | --- | --- |
| Example 31 | 3.85E−09 | 1.68E−09 |
| Example 32 | 1.53E−08 | 1.68E−09 |
| Example 33 | 2.24E−08 | 1.18E−09 |
| Example 34 | 7.1E−09 | 4.76E−09 |
| Example 35 | 5.15E−09 | 4.76E−09 |
| Example 36 | 4.65E−09 | 7.59E−08 |
| Example 37 | 6.3E−09 | 2.05E−08 |
| Example 38 | 2.8E−09 | 2.76E−09 |
| Example 39 | 3.05E−09 | 3.25E−09 |
| Example 40 | 3.75E−09 | 6.15E−09 |
| Example 41 | 3.45E−09 | 9.08E−08 |
| Example 42 | 4.45E−09 | 4.45E−08 |
| Example 43 | 4.55E−09 | 3.11E−08 |
| Example 44 | 3.7E−09 | 2.87E−08 |
| Example 45 | 3.2E−09 | 4.58E−09 |
| Example 46 | 2.55E−09 | 2.34E−08 |
| Example 47 | 4.05E−09 | 1.82E−08 |
| Example 48 | 3.85E−09 | ND |
| Example 49 | 4.65E−09 | ND |
| Example 50 | 6.6E−09 | ND |
| Example 51 | 4.15E−09 | ND |
| Example 52 | 3.7E−09 | ND |
| Example 53 | 4.65E-9 | ND |
| Example 54 | 4.6E−09 | ND |
| Example 55 | 6.35E−09 | ND |
| Example 56 | 4.75E−09 | ND |
| Example 57 | 4.6E−09 | 2.27E−08 |
| Example 58 | ND | ND |
| Example 59 | ND | ND |
| Example 60 | ND | ND |
| Example 61 | ND | ND |
| Example 62 | ND | ND |
| Example 63 | ND | ND |
| Example 64 | ND | ND |
| Example 65 | ND | ND |
| Example 66 | ND | ND |
| Example 67 | ND | ND |
| Example 68 | ND | ND |
| Example 69 | 7.6E−08 | ND |
| Example 70 | ND | ND |
| Example 71 | ND | ND |
| Example 72 | ND | ND |
| Example 73 | ND | ND |
| Example 74 | ND | ND |
| Example 75 | ND | ND |
| Example 76 | ND | ND |
| Example 77 | ND | ND |
| Example 78 | ND | ND |
| Example 79 | 7.6E−09 | ND |
| Example 80 | ND | ND |
| Example 81 | ND | ND |
| Example 82 | 7.7E−09 | ND |

ND: not determined

Example C

Quantification of the Cleaved Form of PARP In Vivo

The ability of the compounds of the invention to induce apoptosis, by measuring cleaved PARP levels, is evaluated in a xenograft model of AMO-1 multiple myeloma cells.

$1.10^7$ AMO-1 cells are grafted sub-cutaneously into immunosuppressed mice (SCID strain). 12 to 14 days after the graft, the animals are treated by intraveinous or oral routes with the various compounds. After treatment, the tumour masses are recovered and lysed, and the cleaved form of PARP is quantified in the tumour lysates.

The quantification is carried out using the "Meso Scale Discovery (MSD) ELISA platform" test, which specifically assays the cleaved form of PARP. It is expressed in the form of an activation factor corresponding to the ratio between the quantity of cleaved PARP in the treated mice divided by the quantity of cleaved PARP in the control mice.

The results show that the compounds of the invention are capable of inducing apoptosis in AMO-1 tumour cells in vivo.

Example D

Anti-Tumour Activity In Vivo

The anti-tumour activity of the compounds of the invention is evaluated in a xenograft model of AMO-1 multiple myeloma cells.

$1 \times 10^7$ AMO-1 cells are grafted sub-cutaneously into immunosuppressed mice (SCID strain).

6 to 8 days after the graft, when the tumour mass has reached about 150 mm$^3$, the mice are treated with the various compounds in a daily schedule (5-day treatment). The tumour mass is measured twice weekly from the start of treatment.

The results obtained using ΔT/C (i.e. qualification parameter of the activity of a product, which is defined as the ratio tumour volume of the treated group/tumour volume of the untreated control group) show that the compounds of the invention induce significant tumour regression during the treatment period.

Example F

Pharmaceutical Composition: Tablets

| | |
|---|---|
| 1000 tablets containing a dose of 5 mg of a compound selected from Examples 1 to 82 | 5 g |
| Wheat starch | 20 g |
| Maize starch | 20 g |
| Lactose | 30 g |
| Magnesium stearate | 2 g |
| Silica | 1 g |
| Hydroxypropylcellulose | 2 g |

The invention claimed is:
1. A compound of formula (I):

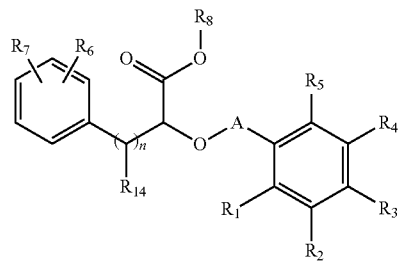

(I)

wherein:
A represents the group

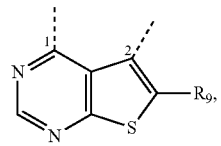

in which 1 is linked to the oxygen atom and 2 is linked to the phenyl ring, $R_1$ represents a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)alkoxy group, a —S—($C_1$-$C_6$)alkyl group, a linear or branched ($C_1$-$C_6$)polyhaloalkyl, a hydroxy group, a hydroxy($C_1$-$C_6$)alkyl group a cyano group, —NR$_{12}$R$_{12}$', -Cy$_5$, or a halogen atom, $R_2$, $R_3$, $R_4$ and $R_5$, independently of one another, represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a hydroxy($C_1$-$C_6$)alkyl group, a linear or branched ($C_1$-$C_6$)alkoxy group, —S—($C_1$-$C_6$)alkyl group, a cyano group, a nitro group, -alkyl($C_0$-$C_6$)—NR$_{10}$R$_{10}$', —O-alkyl($C_1$-$C_6$)—NR$_{10}$R$_{10}$', —O-alkyl($C_1$-$C_6$)—R$_{11}$, —C(O)—OR$_{10}$, —O—C(O)—R$_{10}$, —C(O)—NR$_{10}$R$_{10}$', —NR$_{10}$—C(O)—R$_{10}$', —NR$_{10}$—C(O)—OR$_{10}$', -alkyl($C_1$-$C_6$)—NR$_{10}$—C(O)—R$_{10}$', —SO$_2$—NR$_{10}$R$_{10}$', —SO$_2$-alkyl($C_1$-$C_6$),
or the substituents of one of the pairs ($R_2$, $R_3$), ($R_3$, $R_4$), ($R_4$, $R_5$), when grafted onto two adjacent carbon atoms, together with the carbon atoms carrying them, form an aromatic or non-aromatic ring having from 5 to 7 ring members, which ring may contain from 1 to 3 heteroatoms selected from the group consisting of oxygen, sulphur and nitrogen, wherein the resulting ring may be an substituted by a group selected from the group consisting of a linear or branched ($C_1$-$C_6$)alkyl group, —NR$_{12}$R$_{12}$', -alkyl($C_0$-$C_6$)-Cy$_1$, and oxo, $R_6$ represents —O-alkyl($C_1$-$C_6$)—R$_{11}$, $R_7$ represents a hydrogen atom, a halogen atom, a linear or branched ($C_1$-$C_6$)alkyl group, a linear or branched ($C_2$-$C_6$)alkenyl group, a linear or branched ($C_2$-$C_6$) alkynyl group, a linear or brandied ($C_1$-$C_6$)polyhaloalkyl, a hydroxy group, a linear or branched ($C_1$-$C_6$) alkoxy group, a —S—($C_1$-$C_6$)alkyl group, a cyano group, a nitro group, -alkyl($C_0$-$C_6$)—NR$_{10}$R$_{10}$', —O-alkyl($C_1$-$C_6$)—NR$_{10}$R$_{10}$', —O-Cy$_1$, -alkyl($C_0$-$C_6$)-Cy$_1$, -alkenyl($C_2$-$C_6$)-Cy$_1$, -alkynyl($C_2$-$C_6$)-Cy$_1$, —O-alkyl($C_1$-$C_6$)—R$_{11}$, —C(O)—OR$_{10}$, —O—C(O)—R$_{10}$, —C(O)—NR$_{10}$R$_{10}$', —R$_{10}$—C(O)—R$_{10}$', —NR$_{10}$—C(O)—OR$_{10}$', -alkyl($C_1$-$C_6$)—NR$_{10}$—C(O)—R$_{10}$', —SO$_2$—NR$_{10}$R$_{10}$', —SO$_2$-alkyl($C_1$-$C_6$), $R_8$ represents a hydrogen atom, a linear or branched ($C_1$-$C_8$)alkyl group, a —CHR$_a$R$_b$ group, an aryl group, a heteroaryl group, an arylalkyl($C_1$-$C_6$) group, or a heteroarylalkyl($C_1$-$C_6$) group, $R_9$ represents a linear or branched ($C_1$-$C_6$)alkyl group, a linear or branched ($C_2$-$C_6$)alkenyl group, a linear or branched ($C_2$-$C_6$)alkynyl group, -Cy$_3$, -alkyl($C_1$-$C_6$)-Cy$_3$, -alkenyl($C_2$-$C_6$)-Cy$_3$, -alkynyl($C_2$-$C_6$)-Cy$_3$, -Cy$_3$-Cy$_4$, -alkynyl($C_2$-$C_6$)—O-Cy$_3$, -Cy$_3$-alkyl($C_0$-$C_6$)—O-alkyl($C_0$-$C_6$)-Cy$_4$, a halogen atom, a cyano group, —C(O)—R$_{13}$, or —C(O)—NR$_{13}$R$_{13}$', $R_{10}$ and $R_{10}$', independently of one another, represent a hydrogen atom, a linear or branched ($C_1$-$C_6$)alkyl group, -alkyl($C_0$-$C_6$)-Cy$_1$,
or the substituents of the pair ($R_{10}$, $R_{10}$'), together with the nitrogen atom carrying them, from an aromatic or non-aromatic ring having from 5 to 7 ring members, which ring may contain, in addition to the nitrogen atom, from 1 to 3 heteroatoms selected from the group consisting of oxygen, sulphur and nitrogen, wherein the nitrogen may be substituted by from 1 to 2 groups selected from the group consisting of a hydrogen atom and a linear or branched ($C_1$-$C_6$)alkyl group, and wherein one or more of the carbon atoms of the possible substituents may be deuterated, $R_{11}$ represents -$Cy_5$-alkyl($C_0$-$C_6$)—O-alkyl($C_0$-$C_6$)-$Cy_6$, -$Cy_5$-alkyl($C_0$-$C_6$)-$Cy_6$, -$Cy_5$-alkyl($C_0$-$C_6$)—$NR_{12}$-alkyl($C_0$-$C_6$)-$Cy_6$, $R_{12}$, $R_{12}'$, $R_{13}$ and $R_{13}'$, independently of one another, represent a hydrogen atom or an optionally substituted linear or branched ($C_1$-$C_6$)alkyl group, $R_{14}$ represents a hydrogen atom, a hydroxy group, or a hydroxy($C_1$-$C_6$)alkyl group, $R_a$ represents a hydrogen atom or a linear or branched ($C_1$-$C_6$)alkyl group, $R_b$ represents a —O—C(O)—O—$R_c$ group, a —O—C(O)—$NR_cR_c'$ group, or a —O—P(O)(O$R_c$)$_2$ group, $R_c$ and $R_c'$, independently of one another, represent a hydrogen atom, a linear or branched ($C_1$-$C_8$)alkyl group, a cycloalkyl group, a ($C_1$-$C_6$)alkoxy($C_1$-$C_6$)alkyl group, a ($C_1$-$C_6$)alkoxycarbonyl($C_1$-$C_6$)alkyl group, or the substituents of the pair ($R_c$, $R_c'$), together with the nitrogen atom carrying them, format a non-aromatic ring having from 5 to 7 ring members, which ring may contain, in addition to the nitrogen atom, from 1 to 3 heteroatoms selected from the group consisting of oxygen and nitrogen, wherein the nitrogen may be substituted by a linear or branched ($C_1$-$C_6$)alkyl group, $Cy_1$, $Cy_2$, $Cy_3$, $Cy_4$ and $Cy_5$, independently of one another, represent a cycloalkyl group, a heterocycloalkyl group, an aryl group, or a heteroaryl group, $Cy_6$ represents

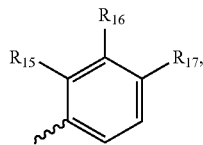

or $Cy_6$ represents a heteroaryl group which is substituted by a group selected from the group consisting of —O—P(O)(O$R_{20}$)$_2$; —O—P(O)(O$^-$)$_2$; —(CH$_2$)$_p$—O—(CHR$_{18}$—CHR$_{19}$—O)$_q$—R$_{20}$; hydroxy; hydroxy($C_1$-$C_6$)alkyl; —(CH$_2$)$_r$—(CH$_2$)$_s$-heterocycloalkyl; and —Y—(CH$_2$)$_q$—NR$_{21}$R$_{21}'$, $R_{15}$ represents a hydrogen atom; a —(CH$_2$)$_p$—O—(CHR$_{18}$—CHR$_{19}$—O)$_q$—R$_{20}$ group; a linear or branched ($C_1$-$C_6$)alkoxy($C_1$-$C_6$)alkyl group; a —Y—(CH$_2$)$_q$—NR$_{21}$R$_{21}'$ group; or a —(CH$_2$)$_r$—Y—(CH$_2$)$_s$-heterocycloalkyl group, $R_{16}$ represents a hydrogen atom; a hydroxy group; a hydroxy($C_1$-$C_6$)alkyl group; a —(CH$_2$)$_r$—Y—(CH$_2$)$_s$-heterocycloalkyl group; a (CH$_2$)$_r$—Y—X—O—(O)(OR$_{20}$)$_2$ group; a —O—P(O)(O$^-$)$_2$ group; a —(CH$_2$)$_p$—O—(CHR$_{18}$—CHR$_{19}$—O)$_q$—R$_{20}$ group; a —(CH$_2$)$_p$—O—C(O)—NR$_{22}$R$_{23}$ group; or a —Y—(CH$_2$)$_q$—NR$_{21}$R$_{21}'$ group, $R_{17}$ represents a hydrogen atom; a —(CH$_2$)$_p$—O—(CHR$_{18}$—CHR$_{19}$—O)$_q$—R$_{20}$ group; a —O—P(O)(OR$_{20}$)$_2$ group; a —O—P(O)(O$^-$)$_2$ group; a hydroxy group; a hydroxy($C_1$-$C_6$)alkyl group; a —(CH$_2$)$_r$—Y—(CH$_2$)$_s$-heterocycloalkyl group; a —Y—(CH$_2$)$_q$—NR$_{21}$R$_{21}'$ group; or an aldonic acid, X represents a —(CH$_2$)$_s$— group or a —C(O)— group, Y represents a bond or an oxygen atom, $R_{18}$ represents a hydrogen atom or a ($C_1$-$C_6$)alkoxy($C_1$-$C_6$)alkyl group, $R_{19}$ represents a hydrogen atom or a hydroxy($C_1$-$C_6$)alkyl group, $R_{20}$ represents a hydrogen atom or a linear or branched ($C_1$-$C_6$)alkyl group, $R_{21}$ and $R_{21}'$, independently of one another, represent a hydrogen atom, a linear or branched ($C_1$-$C_6$)alkyl group, or a hydroxy($C_1$-$C_6$)alkyl group, or the substituents of the pair ($R_{21}$, $R_{21}'$), together with the nitrogen atom carrying them, form an aromatic or non-aromatic ring having from 5 to 7 ring members, which ring may contain, in addition to the nitrogen atom, from 1 to 3 heteroatoms selected from the group consisting of oxygen, sulphur and nitrogen wherein the resulting ring may be substituted by a hydrogen atom or a linear or branched ($C_1$-$C_6$)alkyl group, $R_{22}$ represents a ($C_1$-$C_6$)alkoxy($C_1$-$C_6$)alkyl group, a —(CH$_2$)$_p$—NR$_{24}$R$_{24}'$ group, or a —(CH$_2$)$_p$—O—(CHR$_{18}$—CHR$_{19}$—O)$_q$—R$_{20}$ group, $R_{23}$ represents a hydrogen atom or a ($C_1$-$C_6$)alkoxy($C_1$-$C_6$)alkyl group, or the substituents of the pair ($R_{22}$, $R_{23}$), together with the nitrogen atom carrying them, form an aromatic or non-aromatic ring having from 5 to 18 ring members, which ring may contain, in addition to the nitrogen atom, from 1 to 5 heteroatoms selected from the group consisting of oxygen, sulphur and nitrogen, wherein the resulting ring may be substituted by a hydrogen atom, a linear or branched ($C_1$-$C_6$)alkyl group or a heterocycloalkyl group, $R_{24}$ and $R_{24}'$, independently of one another, represent a hydrogen atom or a linear or branched ($C_1$-$C_6$)alkyl group, or the substituents of the pair ($R_{24}$, $R_{24}'$), together with the nitrogen atom carrying them, form an aromatic or non-aromatic ring having from 5 to 7 ring members, which ring may contain, in addition to the nitrogen atom, from one to 3 heteroatoms selected from the group consisting of oxygen, sulphur and nitrogen, wherein the resulting ring may be substituted by a hydrogen atom or a linear or branched ($C_1$-$C_6$)alkyl group, n is an integer equal to 0 or 1, p is an integer equal to 0, 1 or 2, q is an integer equal to 1, 2, 3 or 4, r and s independently an integer equal to 0 or 1, with the proviso that $R_{15}$, $R_{16}$ and $R_{17}$ cannot represent together a hydrogen atom and, when $R_1$ represents a methyl group, $R_{15}$ cannot represent a methoxyethoxy group, wherein "aryl" means a phenyl, naphthyl, biphenyl, indanyl or indenyl group, "heteroaryl" means any mono- or bi-cyclic group composed of from 5 to 10 ring members, having at least one aromatic moiety and containing from 1 to 3 heteroatoms selected from the group consisting of oxygen, sulphur and nitrogen, "cycloalkyl" means any mono- or bi-cyclic non-aromatic carbocyclic group containing from 3 to 10 ring members, "heterocycloalkyl" means any mono- or bi-cyclic non-aromatic carbocyclic group containing from 3 to 10 ring members, and containing from 1 to 3 heteroatoms selected from the group consisting of oxygen, sulphur and nitrogen, which may include fused, bridged or spiro ring systems, wherein the aryl, heteroaryl, cycloalkyl and heterocycloalkyl groups so defined and the alkyl, alkenyl, alkynyl, alkoxy groups may be substituted by from 1 to 5 groups selected from the group consisting of optionally substituted linear or branched ($C_1$-$C_6$)alkyl, optionally substituted linear or branched ($C_2$-$C_6$)alkenyl group, optionally substituted linear or branched (C₂-C₆)alkynyl group, optionally substituted linear or branched (C₁-C₆)alkoxy, optionally substituted (C₁-C₆)alkyl-S—, hydroxy, oxo(or N-oxide where appropriate), nitro, cyano, —C(O)—OR', —O—C(O)—R', —C(O)—NR'R", —NR'R", —(C=NR')—OR", linear or branched (C₁-C₆)polyhaloalkyl, trifluoromethoxy, or halogen, wherein R' and R", independently of one another, represent a hydrogen atom or an optionally substituted linear or branched (C₁-C₆)alkyl group, and wherein one or more of the carbon atoms of the preceding possible substituents may be deuterated, its enantiomers, diastereoisomers and atropisomers, and addition salts thereof with a pharmaceutically acceptable acid or base.

2. The compound according to claim 1, wherein at least one of the groups selected from the group consisting of R₂, R₃, R₄ and R₅ does not represent a hydrogen atom.

3. The compound according to claim 1, wherein n is an integer equal to 1.

4. The compound according to claim 1, wherein R₁ represents a linear or branched (C₁-C₆)alkyl group or a halogen atom.

5. The compound according to claim 1, wherein R₁₄ represents a hydrogen atom, a hydroxy group, a hydroxymethyl group or a hydroxyethyl group.

6. The compound according to claim 1, wherein R₂ represents a halogen atom, a hydroxy group, a linear or branched (C₁-C₆)alkoxy group.

7. The compound according to claim 1, wherein R₃ represents a hydrogen atom, a hydroxy group, a linear or branched (C₁-C₆)alkoxy group or —O-alkyl(C₁-C₆)—NR₁₀R₁₀'.

8. The compound according to claim 1, wherein R₄ and R₅ represent a hydrogen atom.

9. The compound according to claim 1 wherein

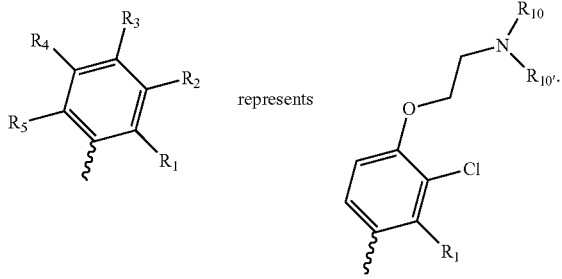

10. The compound according to claim 1, wherein

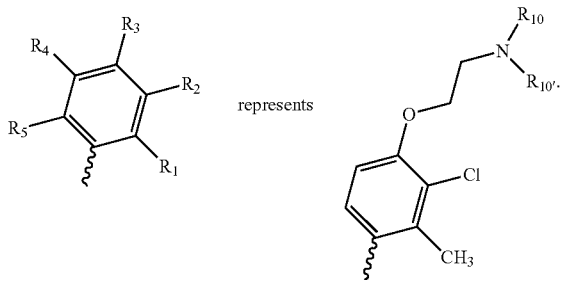

11. The compound according to claim 1, wherein the substituents of the pair (R₁, R₅) are identical and the substituents of the pair (R₂, R₄) are identical.

12. The compound according to claim 1, wherein

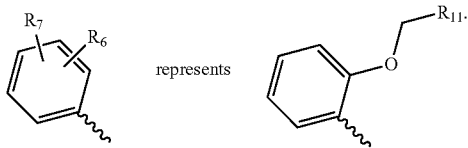

13. The compounds according to claim 1, wherein R₇ represents a hydrogen atom.

14. The compound according to claim 1, wherein R₈ represents a hydrogen atom, a —CHR$_a$R$_b$ group, an optionally substituted linear or branched (C₁-C₈)alkyl group, or a heteroarylalkyl(C₁-C₆) group.

15. The compound according to claim 1, wherein R₉ represents a linear or branched (C₁-C₆)alkyl group, a linear or branched (C₂-C₆)alkenyl group, a linear or branched (C₂-C₆)alkynyl group, an aryl group or a heteroaryl group.

16. The compound according to claim 1, wherein R₁₀ and R₁₀' independently of one another represent a linear or branched (C₁-C₆)alkyl group, or the substituents of the pair (R₁₀, R₁₀'), together with the nitrogen atom carrying them, form a non-aromatic ring having from 5 to 7 ring members, which ding may contain, in addition to the nitrogen atom, from 1 to 3 heteroatoms selected from the group consisting of oxygen, sulphur and nitrogen, wherein the nitrogen may be substituted by a hydrogen atom or a linear or branched (C₁-C₆)alkyl group.

17. The compound according to claim 1, wherein R₁₁ represents -Cy₅-alkyl(C₀-C₆)-Cy₆.

18. The compound according to claim 1, wherein Cy₅ represents a heteroaryl group, particularly, a pyrimidinyl group, a pyrazolyl group, a triazolyl group, a pyrazinyl group or a pyridinyl group.

19. The compound according to claim 1, wherein Cy₆ represents

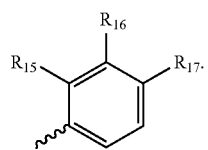

20. The compound according to claim 1, wherein R₁₆ and R₁₇ represent a hydrogen atom and R₁₅ represents a —(CH₂)$_p$—O—(CHR₁₈—CHR₁₉—O)$_q$—R₂₀ group; a linear or branched (C₁-C₆)alkoxy(C₁-C₆)alkyl group; a —Y—(CH₂)$_q$—NR₂₁R₂₁' group; or a —(CH₂)$_r$—Y—(CH₂)$_s$-heterocycloalkyl group.

21. The compounds according to claim 1, wherein R₁₅ and R₁₇ represent a hydrogen atom and R₁₆ represents a hydroxy group; a hydroxy(C₁-C₆)alkyl group;
a —(CH₂)$_r$—Y—(CH₂)$_s$-heterocycloalkyl group; a —O—P(O)(OR₂₀)₂ group; a —O—P(O)(O⁻)₂ group; a —(CH₂)$_p$—O—(CHR₁₈—CHR₁₉—O)$_q$—R₂₀ group; a —(CH₂)$_p$—O—C(O)—NR₂₂R₂₃ group; a (CH₂)$_r$—Y—X—O—P(O)(OR₂₀)₂ group or a —Y—(CH₂)$_q$—NR₂₁R₂₁' group.

22. The compound according to claim 1, wherein R₁₅ and R₁₆ represent a hydrogen atom and R₁₇ represents a —(CH₂)$_p$—O—(CHR₁₈—CHR₁₉—O)$_q$—R₂₀ group; a —O—P(O)(OR₂₀)₂ group; a —O—P(O)(O⁻)₂ group; a hydroxy group; a hydroxy($C_1$-$C_6$)alkyl group; a —$(CH_2)_r$—Y—$(CH_2)_s$-heterocycloalkyl group; a —Y—$(CH_2)_q$—$NR_{21}R_{21}'$ group; or an aldonic acid.

23. The compound according to claim 1, which is selected from the group consisting of:

(2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3-hydroxyphenyl)pyrimidin-4-yl]methoxy}phenyl)propanoic acid;

(2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(4-hydroxyphenyl)pyrimidin-4-yl]methoxy}phenyl)propanoic acid;

(2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[3-(hydroxymethyl)phenyl]pyrimidin-4-yl}methoxy)phenyl]propanoic acid;

(2R)-2-{[(5$S_a$)-5-{3-chloro-2-methyl-4-[3-(4-methylpiperazin-1-yl)ethoxy]phenyl}-6-(4-fluorophenyl)thieno[2,3-d]pyrimidin-4-yl]oxy}-3-[2-({2-[4-(hydroxymethyl)phenyl]pyrimidin-4-yl}methoxy)phenyl]propanoic acid;

(2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{2-[(2,2-dimethyl-1,3-dioxolan-4-yl)methoxy]phenyl}pyrimidin-4-yl)methoxy]phenyl}propanoic acid;

(2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{2-[2-(2-methoxyethoxy)ethoxy]phenyl}pyrimidin-4-yl)methoxy]phenyl}propanoic acid;

(2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-{2-[2-(2-methoxyethoxy)ethoxy]ethoxy}phenyl)pyrimidin-4-yl]methoxy}phenyl)propanoic acid;

(2R)-2-{[(5$S_a$-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[2-(methoxymethyl)phenyl]pyrimidin-4-yl}methoxy)phenyl]propanoic acid;

(2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{2-[(2-methoxyethoxy)methyl]phenyl}pyrimidin-4-yl)methoxy]phenyl}propanoic acid;

(2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{2-[(2-hydroxyethoxy)methyl]phenyl}pyrimidin-4-yl)methoxy]phenyl}propanoic acid;

(2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-{[(2,2-dimethyl-1,3-dioxolan-4-yl)methoxy]methyl}phenyl)pyrimidin-4-yl]methoxy}phenyl)propanoic acid;

(2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{2-3-[(2-hydroxyethoxy)methyl]phenyl}pyrimidin-4-yl)methoxy]phenyl}propanoic acid;

(2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[(1,3-dimethoxypropan-2-yl)oxy]phenyl}pyrimidin-4-yl)methoxy]phenyl}propanoic acid;

(2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{4-[(1,3-dimethoxypropan-2-yl)oxy]phenyl}pyrimidin-4-yl)methoxy]phenyl}propanoic acid;

(2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[4-(2,3-dihydroxypropoxy)phenyl]pyrimidin-4-yl}methoxy)phenyl]propanoic acid;

methyl 6-O-{3-[4-({2-[(2R)-2-carboxy-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}ethyl]phenoxy}methyl)pyrimidin-2-yl]phenyl}-α-D-mannopyranoside;

methyl 6-O-{3-[4-({2-[(2R)-2-carboxy-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}ethyl]phenoxy}methyl)pyrimidin-2-yl]phenyl}-2,3,4-tri-O-methyl-α-D-mannopyranoside;

methyl 6-O-{4-[4-({2-[(2R)-2-carboxy-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}ethyl]phenoxy}methyl)pyrimidin-2-yl]phenyl}-α-D-mannopyranoside;

methyl 6-O-{4-[4-({2-[(2R)-2-carboxy-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}ethyl]phenoxy}methyl)pyrimidin-2-yl]phenyl}-2,3,4-tri-O-methyl-α-D-mannopyranoside;

6-O-{4-[4-({2-[(2R)-2-carboxy-2-{[(5$S_a$)-5-{3-chloro-2-methyl-4-[2-(4-methylpiperazin-1-yl)propoxy]phenyl}-6-(4-fluorophenyl)thieno[2,3-d]pyrimidin-4-yl]oxy}ethyl]phenoxy}methyl)pyrimidin-2-yl]phenyl}-D-mannopyranose;

6-O-{2-[4-({2-[(2R)-2-carboxy-2-{[(5$S_a$)-5-{3-chloro-2-methyl-4-[3-(4-methylpiperazin-1-yl)ethoxy]phenyl}-6-(4-fluorophenyl)thieno[2,3-d]pyrimidin-4-yl]oxy}ethyl]phenoxy}methyl)pyrimidin-2-yl]phenyl}-D-mannonic acid;

1,2-O-[(1R)-1-({4-[4-({2-[(2R)-2-carboxy-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}ethyl]phenoxy}methyl)pyrimidin-2-yl]benzyl}oxy)ethylidene]-β-D-mannopyranose;

(2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{4-[(α-D-mannopyranosyloxy)methyl]phenyl}pyrimidin-4-yl)methoxy]phenyl}propanoic acid;

(2R)-2-{[(5$S_a$)-5-{3-chloro-2-methyl-4-[2-(4-methylpiperazin-1-yl)propoxy]ethoxy}-6-(4-fluorophenyl)thieno[2,3-d]pyrimidin-4-yl]oxy}-3-[2-({2-[4-(2-hydroxyethyl)phenyl]pyrimidin-4-yl}methoxy)phenyl]propanoic acid;

(2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[2-(2,3-dihydroxypropoxy)phenyl]pyrimidin-4-yl}methoxy)phenyl]propanoic acid;

(2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[2-(2-hydroxyethoxy)phenyl]pyrimidin-4-yl}methoxy)phenyl]propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{2-[(2-dihydroxypropoxy)methyl]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-({2-[3-(phosphonooxy)phenyl]pyrimidin-4-yl}methoxy)phenyl]propanoic acid;

4-[4-({2-[(2R)-2-carboxy-2-{[(5S$_a$)-5-{3-chloro-2-methyl-4-[2-(4-methyl piperazin-1-yl)ethoxy]phenyl}-6-(4-fluorophenyl)thieno[2,3-d]pyrimidin-4-yl]oxy}ethyl]phenoxy}methyl)pyrimidin-2-yl]phenyl phosphate;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[3-(2-hydroxyethoxy)phenyl]pyrimidin-4-yl}methoxy)phenyl]propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{4-[2-(2-methoxyethoxy)ethoxy]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{4-[2-(2-hydroxyethoxy)ethoxy]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{([2-(4-{2-[2-(2-methoxyethoxy)ethoxy]ethoxy}phenyl)pyrimidin-4-yl]methoxy}phenyl)propanoic acid;

(2R)-2-{[(5S$_a$)-5-{3-chloro-2-methyl-4-[2-(4-methylpiperazin-1-yl)propoxy]phenyl}-6-(4-fluorophenyl)thieno[2,3-d]pyrimidin-4-yl]oxy}-3-{2-[(2-{4-[2-(dimethylamino)ethoxy]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[(2,2-dimethyl-1,3-dioxolan-4-yl)methoxy]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[3-(15-hydroxy-3-oxo-2,7,10,13-tetraoxa-4-azapentadec-1-yl)phenyl]pyrimidin-4-yl}methoxy)phenyl]propanoic acid;

(2R)-3-(2-{[2-(3-{[(1,4'-bipiperidin-1'-ylcarbonyl)oxy]methyl}phenyl)pyrimidin-4-yl]methoxy}phenyl)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3-{2-[2-(2-hydroxyethoxy)ethoxy]ethoxy}phenyl)pyrimidin-4-yl]methoxy}phenyl)propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[2-(2-hydroxyethoxy)ethoxy]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[2-(2-methoxyethoxy)ethoxy]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[({[2-(4-methylpiperazin-1-yl)ethyl]carbamoyl}oxy)methyl]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[({[2-(morpholin-4-yl)ethyl]carbamoyl}oxy)methyl]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[({[2-(dimethylamino)ethyl]carbamoyl}oxy)methyl]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[({[2-(pyrrolidin-1-yl)ethyl]carbamoyl}oxy)methyl]phenyl}pyrimidin-4-yl)methoxy]phenyl}propanoic acid;

(2R)-3-[2-({2-[3-({[bis(2-methoxyethyl)carbamoyl]oxy}methyl)phenyl]pyrimidin-4-yl}methoxy)phenyl]-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3-{[(1,4,7,10,13-pentaoxa-16-azacyclooctadecan-16-ylcarbonyl)oxy]methyl}phenyl)pyrimidin-4-yl]methoxy}phenyl)propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[3-(2,3-dihydroxypropoxy)phenyl]pyrimidin-4-yl}methoxy)phenyl]propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-{2-[2-(2-methoxyethoxy)ethoxy]ethoxy}phenyl)pyrimidin-4-yl]methoxy}phenyl)propanoic acid;

(2R)-3-(2-{[2-(3-{2-[bis(2-hydroxyethyl)amino]ethoxy}phenyl)pyrimidin-4-yl]methoxy}phenyl)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid;

(2R)-2-{[(5S$_a$)-5-{2,3-dimethyl-4-[2-(4-methylpiperazin-1-yl)ethoxy]phenyl}-6-(4-fluorophenyl)thieno[2,3-d]pyrimidin-4-yl]oxy}-3-{2-[(2-{3-[({[2-(piperidin-1-yl)ethyl]carbamoyl}oxy)methyl]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[2-(morpholin-4-yl)ethoxy]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno

[2,3-d]pyrimidin-4-yl]oxy}-3-{2-[(2-{3-[2-(dimethylamino)ethoxy]phenyl}pyrimidin-4-yl)methoxy]phenyl}propanoic acid;

(2R)-3-(2-{[2-(4-{2-[bis(2-hydroxyethyl)amino]ethoxy}phenyl)pyrimidin-4-yl]methoxy}phenyl)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{[2-(4-{2-[2-(2-hydroxyethoxy)ethoxy]ethoxy}phenyl)pyrimidin-4-yl]methoxy}phenyl)propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{4-[(2,2-dimethyl-1,3-dioxolan-4-yl)methoxy]phenyl}pyrimidin-4-yl)methoxy]phenyl}propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{4-[2-(morpholin-4-yl)ethoxy]phenyl}pyrimidin-4-yl)methoxy]phenyl}propanoic acid;

4-[4-({2-[(2R)-2-carboxy-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}ethyl]phenoxy}methyl)pyrimidin-2-yl]phenyl phosphate disodium salt;

1-[(ethoxycarbonyl)oxy]ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{3-[(1,3-dimethoxypropan-2-yl)oxy]phenyl}pyrimidin-4-yl)methoxy]phenyl}propanoate;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[5-(hydroxymethyl)pyridin-3-yl]pyrimidin-4-yl}methoxy)phenyl]propanoic acid;

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2'-(hydroxymethyl)-2,5'-bipyrimidin-4-yl]methoxy}phenyl)propanoic acid.

24. A pharmaceutical composition comprising the compound according to claim 1, or an addition salt thereof with a pharmaceutically acceptable acid or base, in combination with one or more pharmaceutically acceptable excipients.

25. A method of treating a condition requiring a pro-apoptotic agent in a subject in need thereof, comprising administration of an effective amount of the compound according to claim 1, alone or in combination with one or more pharmaceutically acceptable excipients.

26. The method according to claim 25, wherein the condition is selected from the group consisting of cancer, auto-immune diseases, and immune system diseases.

27. The method according to claim 25, wherein the condition is selected from the group consisting of cancers of the bladder, brain, breast and uterus, chronic lymphoid leukaemias, cancer of the colon, aesophagus and liver, lymphoblastic leukaemias, acute myeloid leukaemias, lymphomas, melanomas, malignant haemopathies, myelomas, ovarian cancer, non-small-cell lung cancer, prostate cancer, pancreatic cancer and small-cell lung cancer.

28. A combination of the compound according to claim 1 with an anti-cancer agent selected from the group consisting of genotoxic agents, mitotic poisons, anti-metabolites, proteasome inhibitors, kinase inhibitors and antibodies.

29. A pharmaceutical composition comprising the combination according to claim 28, in combination with one or more pharmaceutically acceptable excipients.

30. A method of treating cancer in a subject in need thereof, comprising administration of the combination according to claim 28, alone or in combination with one or more pharmaceutically acceptable excipients.

31. A method of treating cancer requiring radiotherapy in a subject in need thereof, comprising administration of the compound according to claim 1, alone or in combination with one or more pharmaceutically acceptable excipients.

* * * * *

UNITED STATES PATENT AND TRADEMARK OFFICE
CERTIFICATE OF CORRECTION

PATENT NO. : 10,322,131 B2  
APPLICATION NO. : 15/738601  
DATED : June 18, 2019  
INVENTOR(S) : Zoltán Szlávik et al.

Page 1 of 1

It is certified that error appears in the above-identified patent and that said Letters Patent is hereby corrected as shown below:

Claim 1:
Column 56, Line 42: "-$R_{10}$-C(O)-$R_{10}$-" should read -- -$NR_{10}$-C(O)-$R_{10}$- --.
      Line 60: "from" should read -- form --.
Column 57, Line 20: "format" should read -- form --.
      Line 43: "-$(CH_2)_r$-$(CH_2)_s$" should read -- -$(CH_2)_r$-Y-$(CH_2)_s$ --.
      Line 52: Insert -- P -- before -- (O) --.

Claim 16:
Column 60, Line 26: "ding" should read -- ring --.

Claim 22:
Column 62, Line 34: "propoxy" should read -- ethoxy --.
      Line 39: "[3" should read -- [2 --.
      Line 55: "propoxy]ethoxy}" should read -- ethoxy}phenyl} --.
Column 63, Line 3: "2-dihy-" should read -- 2,3-dihy- --.
Column 65, Line 38: Insert -- and -- at the end of the line.

Signed and Sealed this  
Thirteenth Day of August, 2019

Andrei Iancu  
*Director of the United States Patent and Trademark Office*